(12) United States Patent
Noda et al.

(10) Patent No.: US 10,043,981 B2
(45) Date of Patent: Aug. 7, 2018

(54) LIGHT-EMITTING MATERIAL, ORGANIC LIGHT-EMITTING DEVICE, AND COMPOUND

(71) Applicant: KYULUX, INC., Fukuoka-shi, Fukuoka (JP)

(72) Inventors: Hiroki Noda, Fukuoka (JP);
Masatsugu Taneda, Fukuoka (JP);
Katsuyuki Shizu, Fukuoka (JP);
Hiroyuki Tanaka, Fukuoka (JP);
Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 15/671,617

(22) Filed: Aug. 8, 2017

(65) Prior Publication Data

US 2017/0338418 A1 Nov. 23, 2017

Related U.S. Application Data

(62) Division of application No. 15/124,119, filed as application No. PCT/JP2015/056286 on Mar. 4, 2015, now Pat. No. 9,773,982.

(30) Foreign Application Priority Data

Mar. 7, 2014 (JP) .................................. 2014-044863

(51) Int. Cl.
| | | |
|---|---|---|
| H01L 51/00 | (2006.01) | |
| H01L 51/50 | (2006.01) | |
| C07D 417/14 | (2006.01) | |
| C09K 11/06 | (2006.01) | |
| C07D 209/88 | (2006.01) | |
| C07D 417/10 | (2006.01) | |
| C07D 403/10 | (2006.01) | |
| C07D 403/14 | (2006.01) | |

(52) U.S. Cl.
CPC ........ *H01L 51/0061* (2013.01); *C07D 209/88* (2013.01); *C07D 403/10* (2013.01); *C07D 403/14* (2013.01); *C07D 417/10* (2013.01); *C07D 417/14* (2013.01); *C09K 11/06* (2013.01); *H01L 51/0067* (2013.01); *H01L 51/0071* (2013.01); *H01L 51/0072* (2013.01); *C09K 2211/1007* (2013.01); *C09K 2211/1022* (2013.01); *C09K 2211/1029* (2013.01); *C09K 2211/1037* (2013.01); *C09K 2211/1059* (2013.01); *H01L 51/5012* (2013.01); *H01L 51/5016* (2013.01)

(58) Field of Classification Search
CPC .... C07D 403/14; C09K 11/06; C09K 11/025; H01L 51/0072; H01L 51/0067; H01L 51/0085

See application file for complete search history.

(56) References Cited

U.S. PATENT DOCUMENTS

| | | |
|---|---|---|
| 2003/0129448 A1 | 7/2003 | Lin et al. |
| 2007/0231503 A1 | 10/2007 | Hwang et al. |
| 2008/0169755 A1 | 7/2008 | Kim et al. |
| 2013/0168656 A1 | 7/2013 | Tasi et al. |

FOREIGN PATENT DOCUMENTS

| | | |
|---|---|---|
| CN | 102216269 A | 10/2011 |
| CN | 102738413 A | 10/2012 |
| CN | 103119125 A | 6/2013 |
| CN | 105073737 A | 11/2015 |
| JP | H9-134020 A | 5/1997 |
| JP | 2004-288380 A | 10/2004 |
| JP | 2005089543 | * 4/2005 |
| JP | 2006-028176 A | 2/2006 |
| JP | 2007-091722 A | 4/2007 |
| JP | 2013-251480 A | 12/2013 |
| JP | 2014-101275 A | 6/2014 |
| KR | 20110041727 A | 4/2011 |
| KR | 10-20110102055 A | 9/2011 |
| KR | 20110111095 A | 10/2011 |
| KR | 20120113880 A | 10/2012 |
| KR | 20130024521 A | 3/2013 |
| KR | 20130102673 A | 9/2013 |
| KR | 20140000640 A | 1/2014 |
| WO | 2012005360 A1 | 1/2012 |
| WO | 2012011756 A1 | 1/2012 |

(Continued)

OTHER PUBLICATIONS

Office Action for corresponding Chinese Patent Application No. 201580012014.8, dated Jun. 22, 2017, with English translation.
International Preliminary Report on Patentability for corresponding PCT International Application No. PCT/JP2015/056286, dated Sep. 13, 2016, with English translation.
International Search Report and Search Opinion for corresponding PCT International Application No. PCT/JP2015/056286.

(Continued)

*Primary Examiner* — Erich A Leeser
(74) *Attorney, Agent, or Firm* — Browdy and Neimark, PLLC

(57) ABSTRACT

A compound represented by the general formula (1) is useful as a light-emitting material. In the general formula (1), $Ar^1$ to $Ar^3$ each represent a substituted or unsubstituted aryl group, provided that at least one of $Ar^1$ to $Ar^3$ each represent a carbazolyl group having an N-position substituted with a group containing an electron withdrawing group.

General Formula (1)

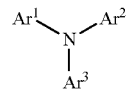

10 Claims, 15 Drawing Sheets

(56) References Cited

FOREIGN PATENT DOCUMENTS

| WO | 2012086576 A1 | 6/2012 |
| WO | 2012121561 A1 | 9/2012 |
| WO | 2012165844 A1 | 12/2012 |
| WO | 2013012298 A1 | 1/2013 |
| WO | 2013062043 A1 | 5/2013 |
| WO | 2013122402 A1 | 8/2013 |
| WO | 2013165192 A1 | 11/2013 |
| WO | WO2014014310 A1 | 1/2014 |
| WO | 2014027814 A1 | 2/2014 |
| WO | 2013081088 A1 | 4/2015 |

OTHER PUBLICATIONS

Office Action for corresponding Chinese Patent Application No. 201580012014.8, dated Mar. 12, 2018, with English translation.

\* cited by examiner

LIGHT-EMITTING MATERIAL, ORGANIC LIGHT-EMITTING DEVICE, AND COMPOUND

TECHNICAL FIELD

The present invention relates to a compound that is useful as a light-emitting material, and an organic light-emitting device using the same.

BACKGROUND ART

An organic light-emitting device, such as an organic electroluminescence device (organic EL device), has been actively studied for enhancing the light emission efficiency thereof. In particular, various studies for enhancing the light-emitting efficiency have been made by newly developing and combining an electron transporting material, a hole transporting material, a light-emitting material and the like constituting an organic electroluminescence device. Among the studies, there are studies relating to an organic electroluminescence device utilizing a tertiary amine substituted with a carbazolyl group.

Patent Document 1 describes an example using a tertiary amine substituted with one carbazolyl group having an N-position substituted with an ethyl group and two substituted phenyl groups, as a light-emitting material in a light-emitting layer present between a pair of electrodes constituting an organic electroluminescence device. However, Patent Document 1 does not describe the compound, in which an N-position of the carbazolyl group substituted on the tertiary amine is substituted by a substituent other than an ethyl group.

Patent Document 2 describes the use of a compound represented by the following formula as a material of a hole injection layer or a hole transporting layer of an organic electroluminescence device. Herein, $R_4$ and $R_5$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted polycondensed ring having from 5 to 30 carbon atoms, a hydroxy group, a cyano group, or a substituted or unsubstituted amino group, and $Ar_2$ represents a substituted or unsubstituted aryl group having from 6 to 30 carbon atoms or a substituted or unsubstituted aromatic heterocyclic group having from 2 to 30 carbon atoms. However, Patent Document 2 does not describe usefulness of the compound represented by the general formula as a light-emitting material. Furthermore, the literature does not describe a specific example of a compound, in which a phenyl group of an N-phenylcarbazolyl group substituted on a tertiary amine is substituted with a substituent.

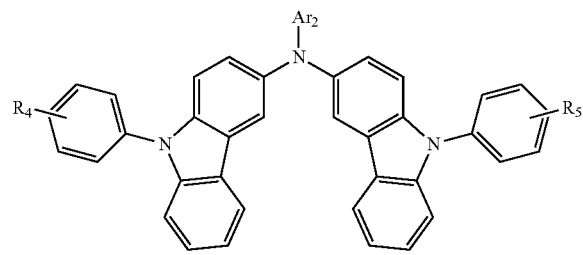

Patent Document 3 describes an example using a compound represented by the following formula as a phosphorescent host material. However, Patent Document 3 does not describe usefulness of the compound as a light-emitting material. Furthermore, the literature does not describe a specific example of a compound, in which a phenyl group of an N-phenylcarbazolyl group substituted on a tertiary amine is substituted with a substituent.

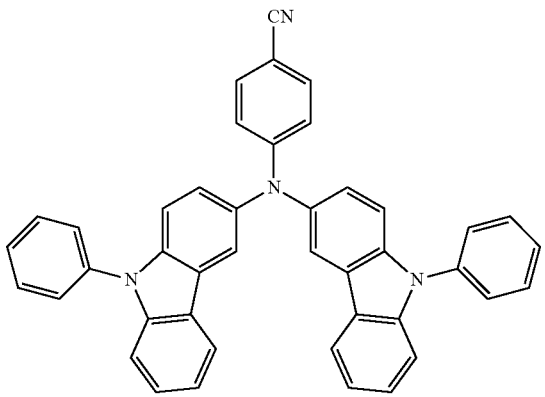 [SMILES: N#Cc1ccc(N(c2ccc3c(c2)c2ccccc2n3-c2ccccc2)c2ccc3c(c2)c2ccccc2n3-c2ccccc2)cc1]

CITATION LIST

Patent Literatures

Patent Document 1: US-A 2003/0129448
Patent Document 2: US-A 2007/0231503
Patent Document 3: JP-A-2006-28176

SUMMARY OF INVENTION

Technical Problem

As described above, Patent Document 1 describes the use of a tertiary amine substituted with one carbazolyl group having an N-position substituted with an ethyl group and two substituted phenyl groups, as a light-emitting material. However, as a result of the actual evaluation of the light emission characteristics of the compound by the present inventors, it has been found that the light emission characteristics are not sufficiently satisfactory, and it is necessary to provide a light-emitting material having better light emission characteristics.

Thus, the inventors have started to investigate variously a tertiary amine substituted with a carbazolyl group, have firstly found that among many analogous structures, a tertiary amine group having a carbazolyl group having an N-position substituted with a group containing an electron withdrawing group has usefulness as a light-emitting material, and have decided to continue the investigations. As described above, Patent Documents 2 and 3 describe that a tertiary amine substituted with an N-phenylcarbazolyl group is useful as a hole transporting material of a hole injection layer or a hole transporting layer or an organic electroluminescence device, and a host material. However, there is no investigation as to whether or not the compounds described in Patent Documents 2 and 3 are capable of functioning as a light-emitting material. A light-emitting material has demanded properties and functions that are different from a hole transporting material and a host material, and therefore the usefulness of the compounds described in Patent Documents 2 and 3 as a light-emitting material is unknown. Patent Document 1 relates to a light-emitting material, but the literature does not describe a compound, in which an N-position of a carbazolyl group substituted on a tertiary amine is substituted with a group containing an electron withdrawing group. Accordingly, the usefulness as a light-emitting material of a tertiary amine having a carbazolyl group having an N-position substituted with a group containing an electron withdrawing group cannot be expected.

Under the circumstances, the inventors have further made investigations on the usefulness as a light-emitting material of a tertiary amine having a carbazolyl group having an N-position substituted with a group containing an electron withdrawing group, and have made accumulated studies for finding a compound having excellent light emission characteristics. Furthermore, the inventors have made earnest investigations for providing a general formula of the compounds useful as a light-emitting material and generalizing the structure of an organic light-emitting material having a high light emission efficiency.

Solution to Problem

As a result of the earnest investigations performed, the inventors have found that a tertiary amine having a carbazolyl group having an N-position substituted with a group containing an electron withdrawing group has excellent properties as a light-emitting material. The inventors also have found that the group of compounds includes compounds that are useful as a delayed fluorescent emitter, and have clarified that an organic light-emitting device having a high light emission efficiency can be provided inexpensively. Based on the knowledge, the inventors have provided the following inventions as measures for solving the problems.

[1] A light-emitting material containing a compound represented by the following general formula (1):

General Formula (1)

wherein in the general formula (1), $Ar^1$ to $Ar^3$ each independently represent a substituted or unsubstituted aryl group, provided that at least one of $Ar^1$ to $Ar^3$ each independently represent a carbazolyl group having an N-position substituted with a group containing an electron withdrawing group.

[2] The light-emitting material according to the item [1], wherein the carbazolyl group having an N-position substituted with a group containing an electron withdrawing group is an N-substituted carbazol-3-yl group.

[3] The light-emitting material according to the item [1] or [2], wherein the electron withdrawing group is a phenyl group substituted with at least one electron withdrawing group.

[4] The light-emitting material according to the item [3], wherein the substitution position of the electron withdrawing group is the 4-position of the phenyl group.

[5] The light-emitting material according to the item [3] or [4], wherein the electron withdrawing group is a heterocyclic group having a nitrogen atom as a constitutional atom of the ring, or a cyano group.

[6] The light-emitting material according to the item [5], wherein the heterocyclic group having a nitrogen atom as a constitutional atom of the ring is a heterocyclic group represented by any one of the following formulae:

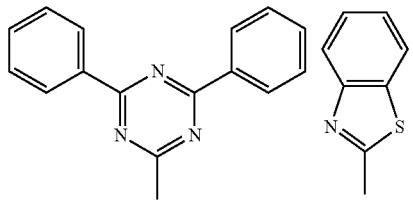

[7] The light-emitting material according to any one of the items [1] to [6], wherein 2 or 3 of $Ar^1$ to $Ar^3$ each represent the carbazolyl group having an N-position substituted with a group containing an electron withdrawing group.

[8] The light-emitting material according to the item [7], wherein the carbazolyl groups having an N-position substituted with a group containing an electron withdrawing group have the same structure.

[9] The light-emitting material according to any one of the items [1] to [6], wherein 1 or 2 of $Ar^1$ to $Ar^3$ each represent the carbazolyl group having an N-position substituted with a group containing an electron withdrawing group, and the other one thereof represents a substituted or unsubstituted phenyl group.

[10] The light-emitting material according to any one of the items [1] to [9], wherein the carbazolyl group having an N-position substituted with a group containing an electron withdrawing group is a group represented by the following general formula (2):

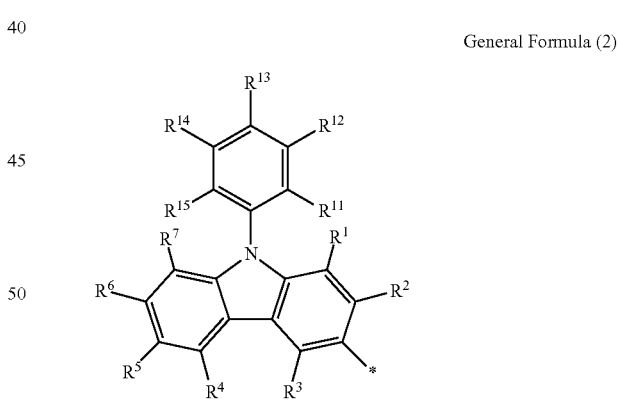

General Formula (2)

wherein in the general formula (2), * represents a position bonded to the nitrogen atom in the general formula (1); and $R^1$ to $R^7$ and $R^{11}$ to $R^{15}$ each independently represent a hydrogen atom or a substituent, provided that at least one of $R^{11}$ to $R^{15}$ each independently represent a substituent, $R^{11}$ to $R^{15}$ may be bonded to each other to form a cyclic structure, and $R^1$ and $R^2$, $R^4$ and $R^5$, $R^5$ and $R^6$, and $R^6$ and $R^7$ each may be bonded to each other to form a cyclic structure.

[11] A delayed fluorescent emitter containing a compound represented by the following general formula (1):

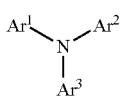

General Formula (1)

wherein in the general formula (1), $Ar^1$ to $Ar^3$ each independently represent a substituted or unsubstituted aryl group, provided that at least one of $Ar^1$ to $Ar^3$ each independently represent a carbazolyl group having an N-position substituted with a group containing an electron withdrawing group.

[12] An organic light-emitting device containing the light-emitting material according to any one of the items [1] to [10].

[13] The organic light-emitting device according to the item [12], wherein the organic light-emitting device emits delayed fluorescent light.

[14] The organic light-emitting device according to the item [12] or [13], wherein the organic light-emitting device is an organic electroluminescence device.

[15] A compound represented by the following general formula (1'):

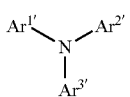

General Formula (1')

wherein in the general formula (1'), $Ar^{1'}$ to $Ar^{3'}$ each independently represent a substituted or unsubstituted aryl group, provided that at least one of $Ar^{1'}$ to $Ar^{3'}$ each independently represent a carbazolyl group having an N-position substituted with a group containing an electron withdrawing group.

Advantageous Effects of Invention

The compound of the invention is useful as a light-emitting material. The compound of the invention includes one that emits delayed fluorescent light. The organic light-emitting device using the compound of the invention as a light-emitting material is capable of achieving a high light emission efficiency.

DESCRIPTION OF EMBODIMENTS

Figure 1:
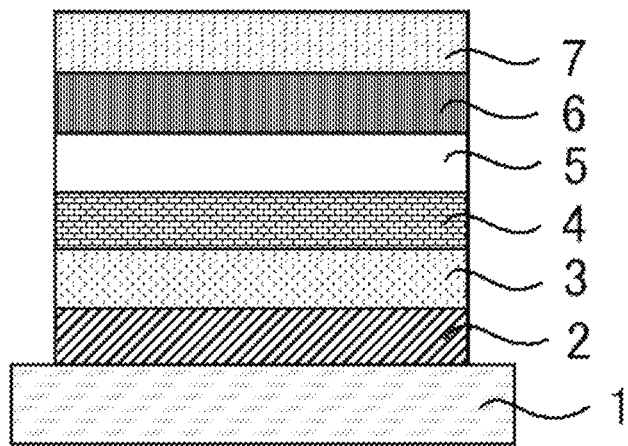
FIG. 1 shows a schematic cross sectional view showing an example of a layer structure of an organic electroluminescence device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1$H, and all or a part of them may be $^2$H (deuterium (D)).

Compound Represented by General Formula (1)

The light-emitting material of the invention contains a compound represented by the following general formula (1).

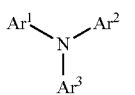

General Formula (1)

In the general formula (1), $Ar^1$ to $Ar^3$ each independently represent a substituted or unsubstituted aryl group, provided that at least one of $Ar^1$ to $Ar^3$ each independently represent a carbazolyl group having an N-position substituted with a group containing an electron withdrawing group. The carbazolyl group having an N-position substituted with a group containing an electron withdrawing group is present as from 1 to 3 of $Ar^1$ to $Ar^3$, and preferably 2 or 3 thereof. In the case where 2 or 3 of $Ar^1$ to $Ar^3$ each represent the carbazolyl group having an N-position substituted with a group containing an electron withdrawing group, the carbazolyl groups having an N-position substituted with a group containing an electron withdrawing group may be the same as or different from each other, and are preferably the same as each other.

In the carbazolyl group having an N-position substituted with a group containing an electron withdrawing group, the electron withdrawing group may be bonded directly to the N-position of the carbazolyl group, or the electron withdrawing group may be bonded to the N-position of the carbazolyl group through a linking group, such as a phenyl group. Examples of the preferred case include the case where the electron withdrawing group is bonded through a phenyl group, and the case where the electron withdrawing group is bonded directly to the N-position.

In the case where the electron withdrawing group is bonded through a phenyl group, the bonding position to the nitrogen atom in the carbazolyl group is not particularly limited, and is preferably the 2-position or the 3-position of the phenyl group, and more preferably the 3-position thereof. Specifically, an N-substituted phenylcarbazol-2-yl group and an N-substituted phenylcarbazol-3-yl group are preferred, and an N-substituted phenylcarbazol-3-yl group is more preferred. In the case where 2 or 3 of $Ar^1$ to $Ar^3$ each represent an N-substituted phenylcarbazolyl group, the bonding positions to the nitrogen atom in the N-substituted phenylcarbazolyl groups may be the same as or different from each other, and are preferably the same as each other.

An N-substituted carbazol-3-yl group can be represented by the following general formula (2).

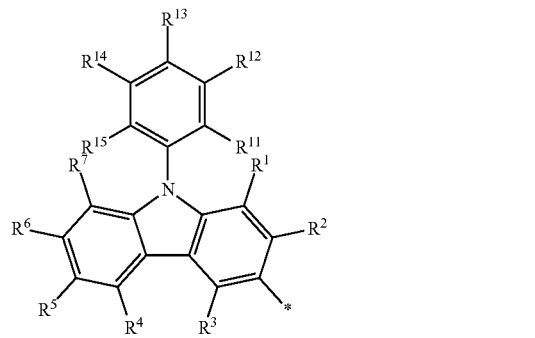

General Formula (2)

In the general formula (2), * represents a position bonded to the nitrogen atom in the general formula (1); and $R^1$ to $R^7$ and $R^{11}$ to $R^{15}$ each independently represent a hydrogen atom or a substituent, provided that at least one of $R^{11}$ to $R^{15}$ each independently represent a substituent. The number of the substituent in $R^{11}$ to $R^{15}$ may be only 1 or may be 2 or more.

In the case where only 1 of $R^{11}$ to $R^{15}$ represents a substituent, any one of $R^{12}$ to $R^{14}$ preferably represents a substituent, and $R^{13}$ more preferably represents a substituent.

In the case where 2 or more of $R^{11}$ to $R^{15}$ each represent a substituent, it is preferred that at least $R^{12}$ and $R^{13}$ each represent a substituent, or at least $R^{13}$ and $R^{14}$ each represent a substituent. Specifically, in the case where 4 of $R^{11}$ to $R^{15}$ each represent a substituent, it is preferred that $R^{11}$ to $R^{14}$ each represent a substituent, or $R^{12}$ to $R^{15}$ each represent a substituent; in the case where 3 of $R^{11}$ to $R^{15}$ each represent a substituent, it is preferred that $R^{12}$ to $R^{14}$ each represent a substituent; and in the case where 2 of $R^{11}$ to $R^{15}$ each represent a substituent, it is preferred that $R^{12}$ and $R^{13}$ each represent a substituent, or $R^{13}$ and $R^{14}$ each represent a substituent.

Among the substituents represented by $R^{11}$ to $R^{15}$, at least one thereof is preferably an electron withdrawing group, and at least $R^{13}$ (i.e., the 4-position of the phenyl group) is preferably an electron withdrawing group. The compound represented by the general formula (1) has a tendency by at least one of $R^{11}$ to $R^{15}$ representing a substituent that the energy difference $\Delta E_{ST}$ between the singlet excited state and the triplet excited state is small while ensuring a sufficient value for the radiative rate constant $k_r$ from the singlet excited state $S_1$ to the ground state $S_0$, and thus is advantageous for the enhancement of the light emission efficiency. It is estimated that this is because the introduction of the phenyl group having an electron withdrawing group appropriately separates HOMO and LUMO while suppressing the structural twist of the molecule small.

The number of an electron withdrawing group in $R^{11}$ to $R^{15}$ may be 1 or may be 2 or more, and is preferably one. In the case where 2 or more of $R^{11}$ to $R^{15}$ each are an electron withdrawing group, the plural electron withdrawing groups may be the same as or different from each other, and are preferably the same as each other. Examples of the electron withdrawing group include a heterocyclic group containing a nitrogen atom, a cyano group, a carboxyl group, a group bonded through ester (for example, an alkoxycarbonyl group, an aryloxycarbonyl group, and an acyloxy group), and a group bonded through carbonyl (for example, an acyl group and a carbamoyl group), and a heterocyclic group containing a nitrogen atom, and a cyano group are preferred. Examples of the heterocyclic group containing a nitrogen atom include heterocyclic groups represented by the following formulae. However, the heterocyclic group containing a nitrogen atom capable of being used in the invention is not limited to the following formulae.

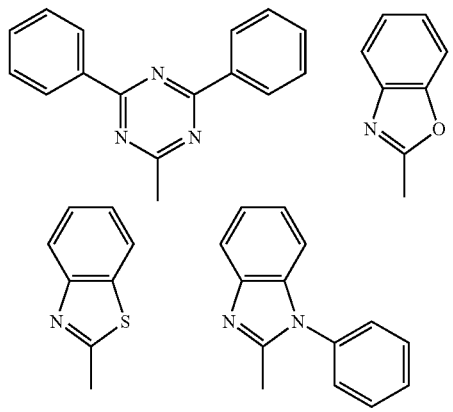

In the case where at least one of $R^{11}$ to $R^{15}$ represents an electron withdrawing group, the substituents among $R^{11}$ to $R^{15}$ may be only electron withdrawing groups or may include a substituent other than an electron withdrawing group. In the case where the substituents among $R^{11}$ to $R^{15}$ include a substituent other than an electron withdrawing group, the number of a substituent other than an electron withdrawing group is not particularly limited, and may be only 1 or may be 2 or more. In the case where the number of a substituent other than an electron withdrawing group in $R^{11}$ to $R^{15}$ is 2 or more, the substituents may be the same as or different from each other, and are preferably the same as each other. The substituent other than an electron withdrawing group is not particularly limited, and examples thereof include an alkyl group.

The number of substituents in $R^1$ to $R^7$ is not particularly limited, and all $R^1$ to $R^7$ may be unsubstituted (i.e., a hydrogen atom). In the case where 2 or more of $R^1$ to $R^7$ each are a substituent, the plural substituents may be the same as or different from each other. In the case where any of $R^1$ to $R^7$ is a substituent, the substituent is preferably any of $R^4$ to $R^6$.

Examples of the substituent that may be represented by $R^1$ to $R^7$ include a hydroxy group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

$R^1$ and $R^2$, $R^4$ and $R^5$, $R^5$ and $R^6$, and $R^6$ and $R^7$ each may be bonded to each other to form a cyclic structure. The cyclic structure may be an aromatic ring or an aliphatic ring, and may be a structure containing a hetero atom, and the cyclic structure may be a condensed ring containing two or more rings. The hetero atom referred herein is preferably selected from the group consisting of a nitrogen atom, an oxygen atom, and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, and a cycloheptaene ring.

In the case where any of $Ar^1$ to $Ar^3$ in the general formula (1) is an N-substituted phenylcarbazolyl group having a bonding position to the nitrogen atom that is other than the 3-position, for the descriptions and the preferred ranges of the substituent capable of being substituted on the N-substituted phenylcarbazolyl group and a preferred example of the cyclic structure formed by substituents bonded to each other, reference may be made to the corresponding descriptions in the general formula (2), provided that the descriptions for the substituents that may be represented by $R^1$ to $R^3$ in the general formula (2) should be read as the descriptions for the substituents that is substituted on the position other than the position bonded to the nitrogen atom of the benzene ring corresponding to the benzene ring bonded to $R^1$ to $R^3$.

The carbazolyl group having an N-position substituted with a group containing an electron withdrawing group contained in the general formula (1) may be a carbazolyl group having an N-position that is substituted directly with an electron withdrawing group. The electron withdrawing group that is bonded directly to the N-position may be selected from electron withdrawing groups capable of being bonded to the N-position of the carbazolyl group, and examples thereof include an electron withdrawing group having a cyclic structure and an electron withdrawing group having a benzene ring or a heterocyclic aromatic ring. Specific examples thereof include the following electron withdrawing group.

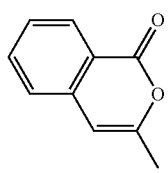

In the case where 1 or 2 of Ar$^1$ to Ar$^3$ each represent the carbazolyl group having an N-position substituted with a group containing an electron withdrawing group, Ar$^1$ to Ar$^3$ that is other than the carbazolyl group having an N-position substituted with a group containing an electron withdrawing group is preferably a substituted or unsubstituted aryl group having from 6 to 14 carbon atoms, and more preferably a substituted or unsubstituted phenyl group. For the descriptions and the preferred ranges of the substituent capable of being substituted on the aryl group, reference may be made to the descriptions and the preferred ranges for the substituents that may be represented by R$^1$ to R$^7$.

Preferred examples of the compound represented by the general formula (1) include a compound, in which 2 of Ar$^1$ to Ar$^3$ each represent a group represented by the general formula (2), and the other one thereof represents a substituted or unsubstituted phenyl group.

Specific examples of the compound represented by the general formula (1) are shown below. However, the compound represented by the general formula (1) capable of being used in the invention is not construed as being limited to the specific examples.

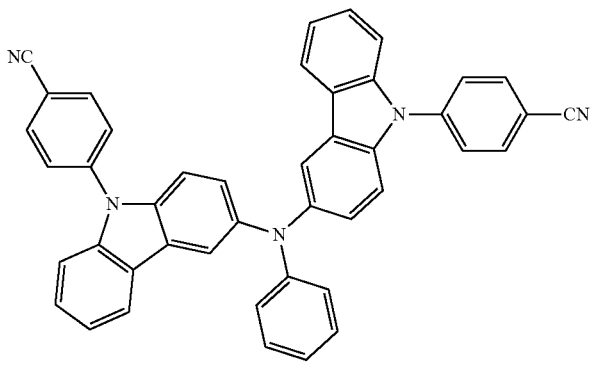

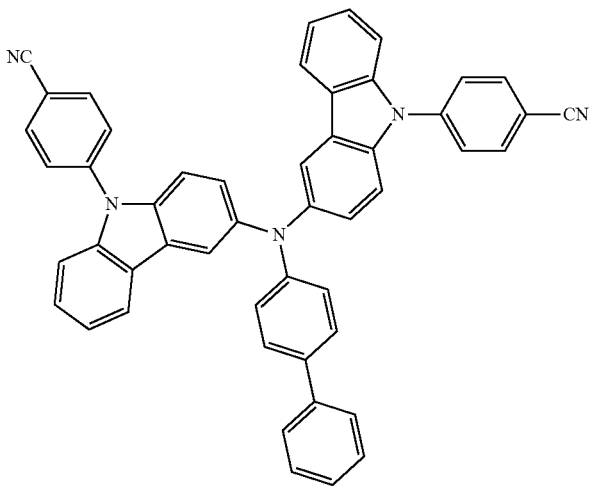

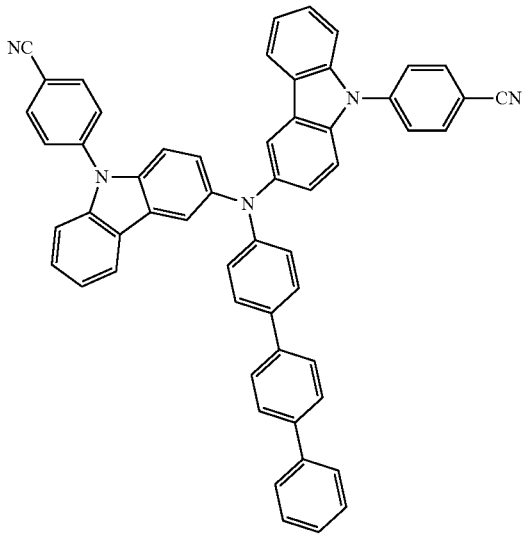

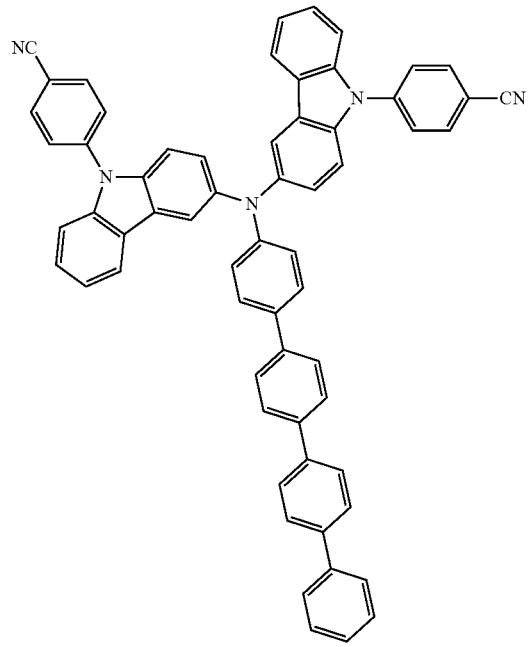

-continued
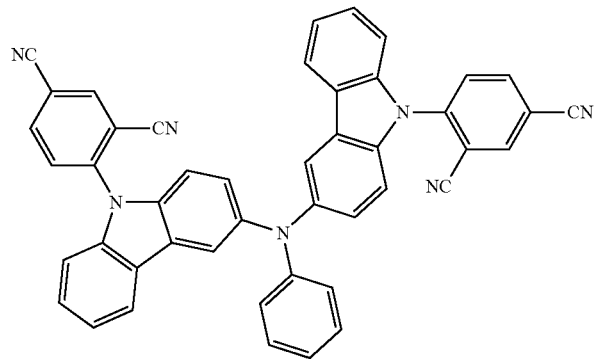
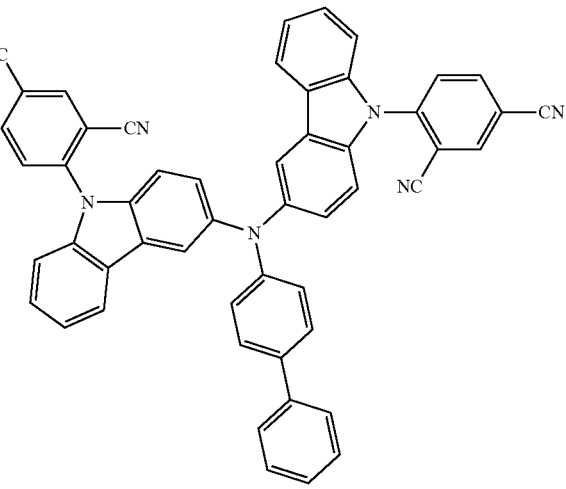
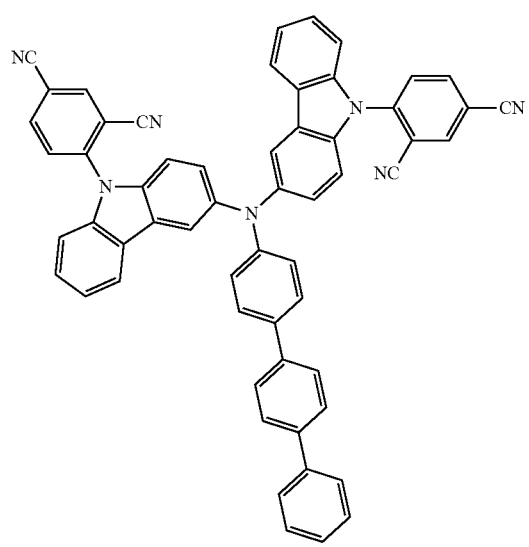
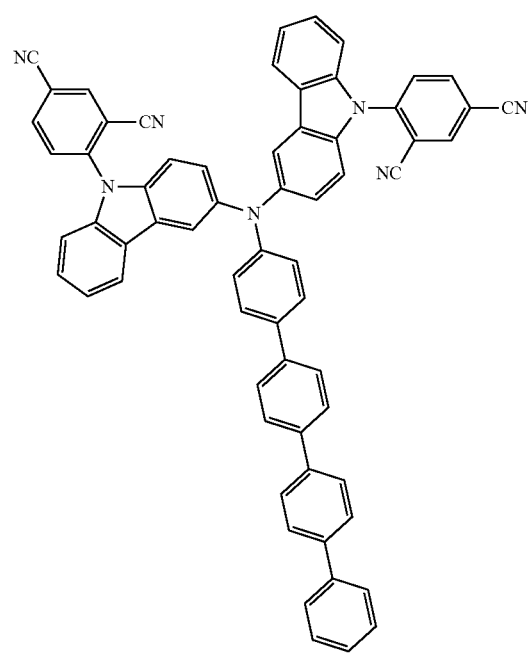
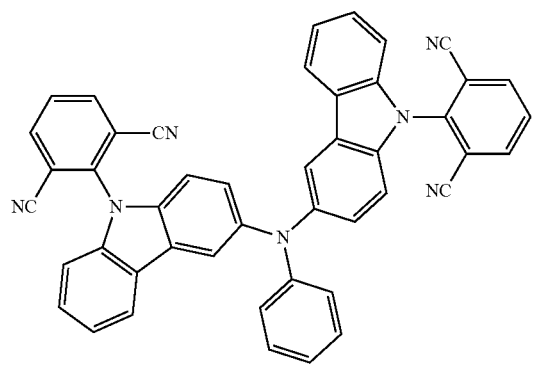
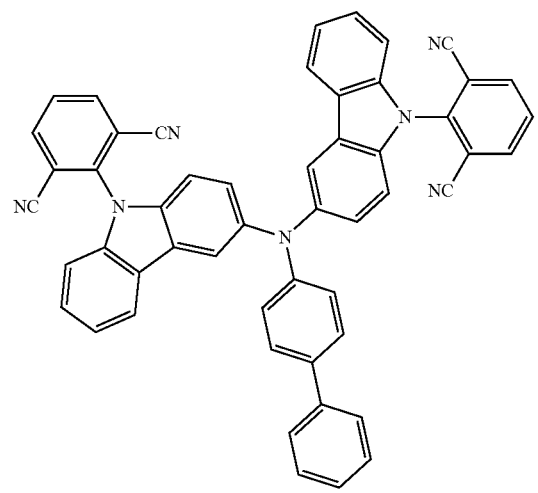

-continued
15
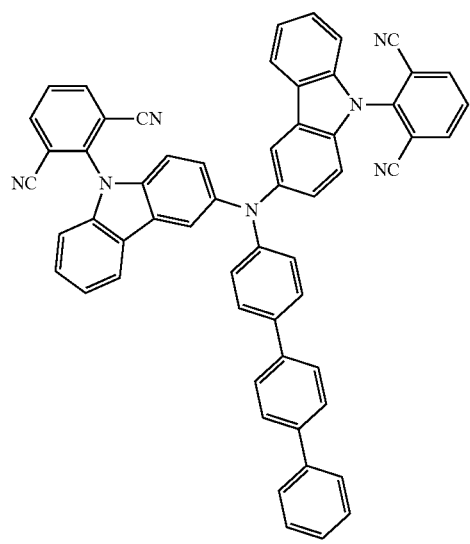
16
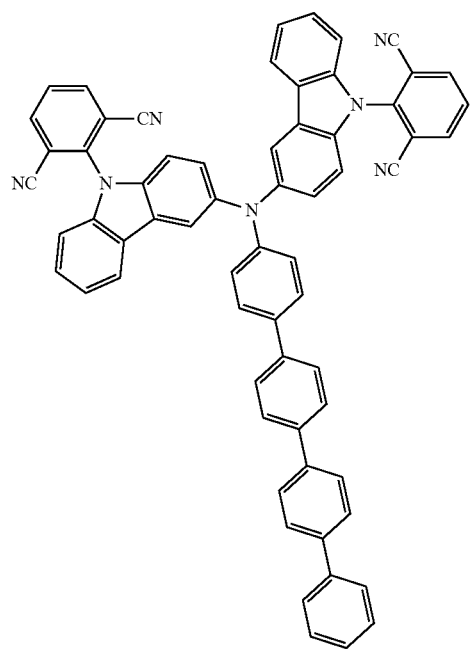
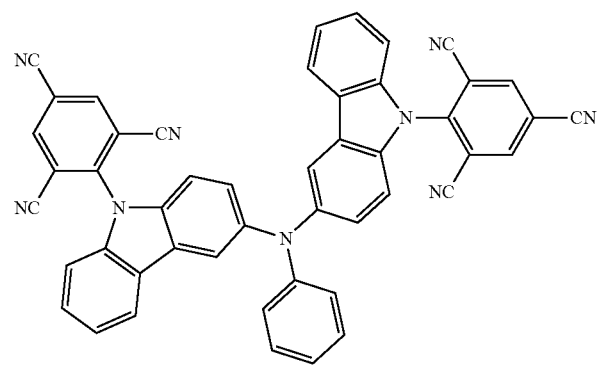
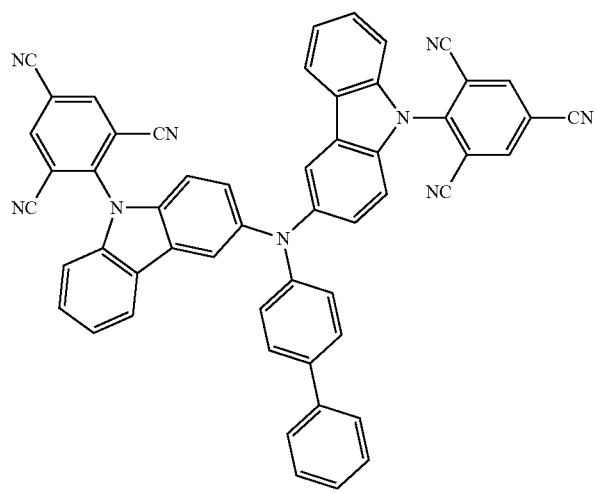

-continued
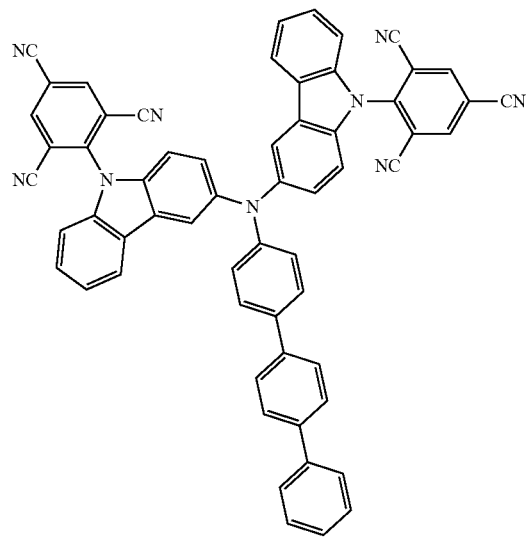
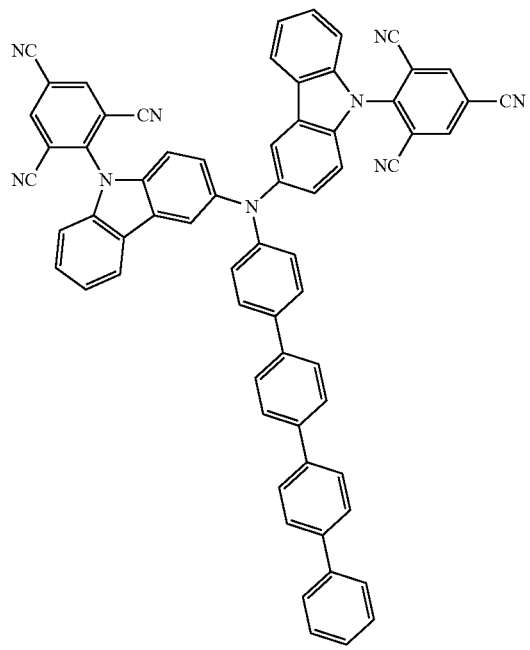
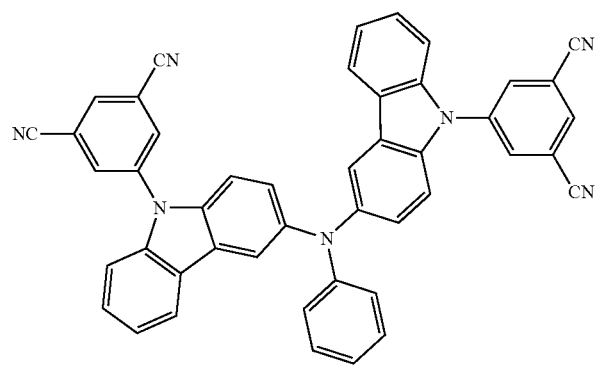
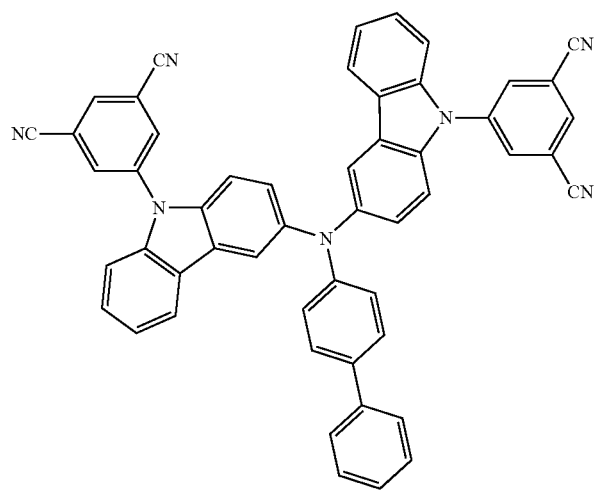

19
20
-continued
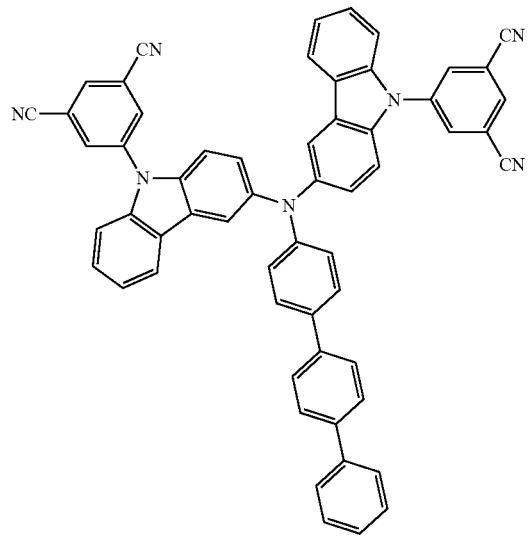
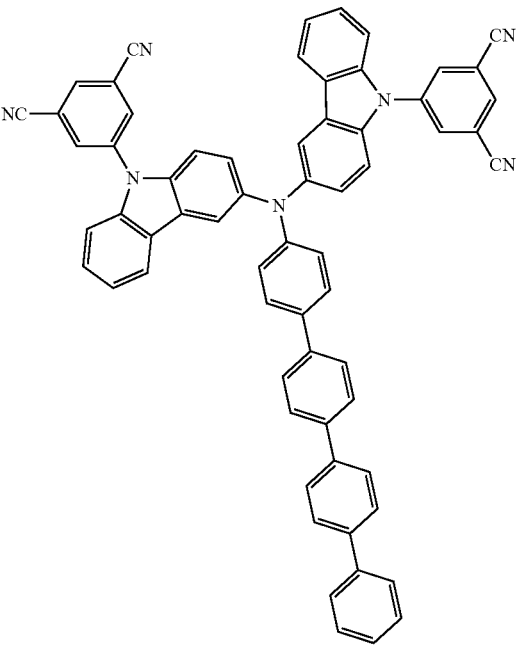
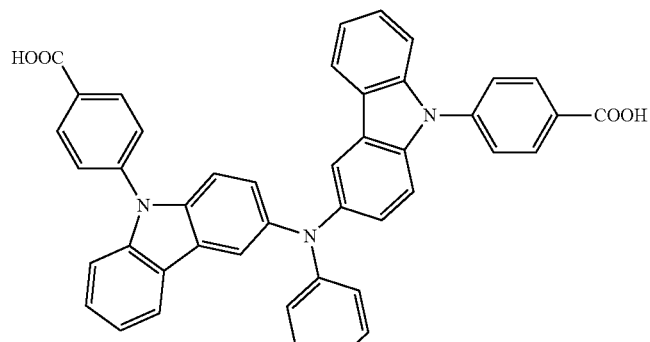
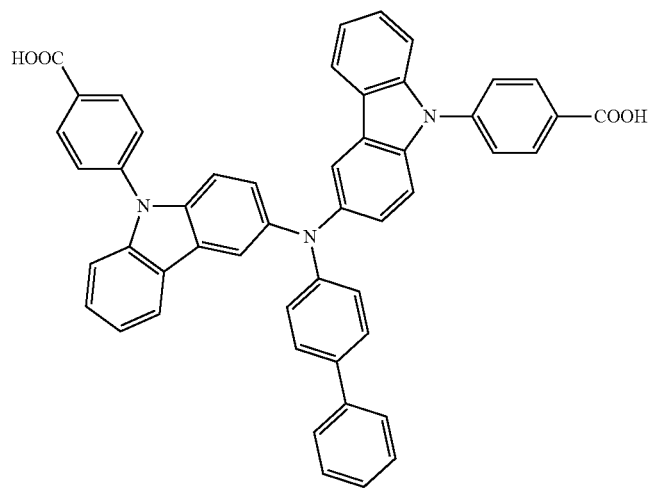

-continued
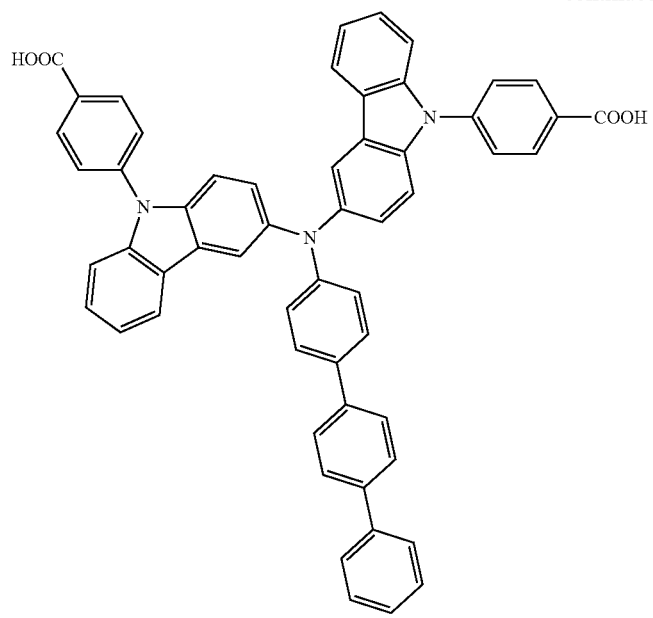
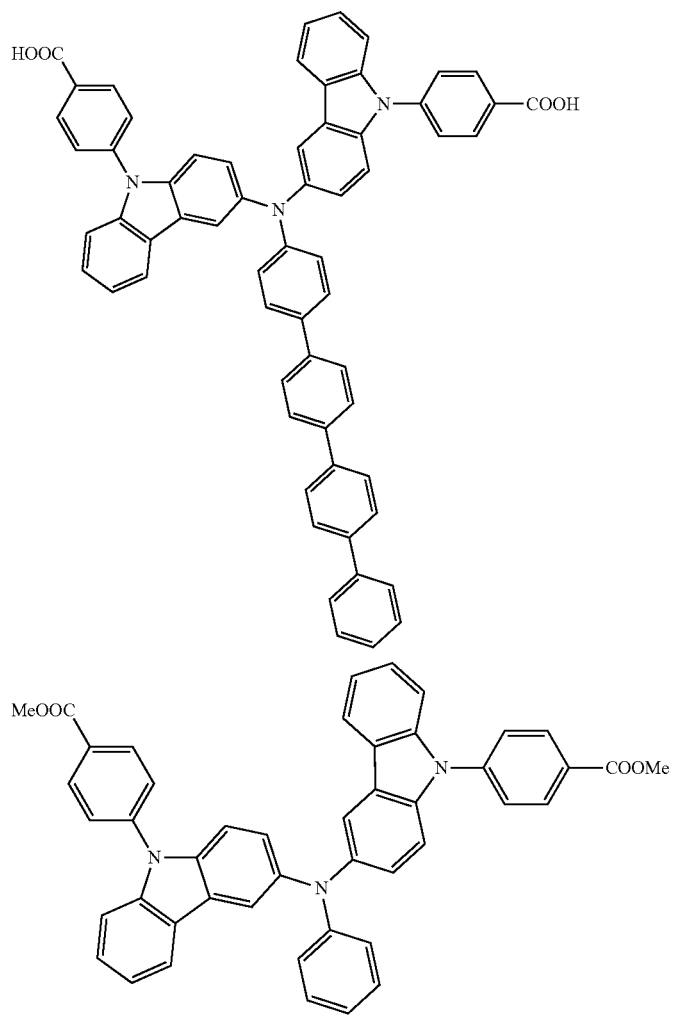

-continued
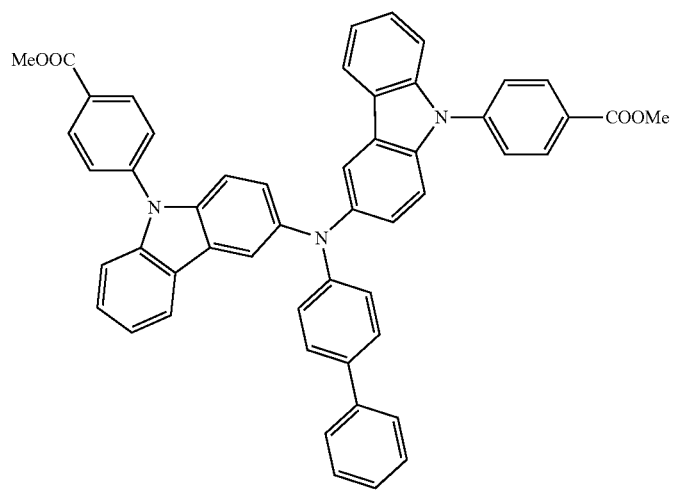
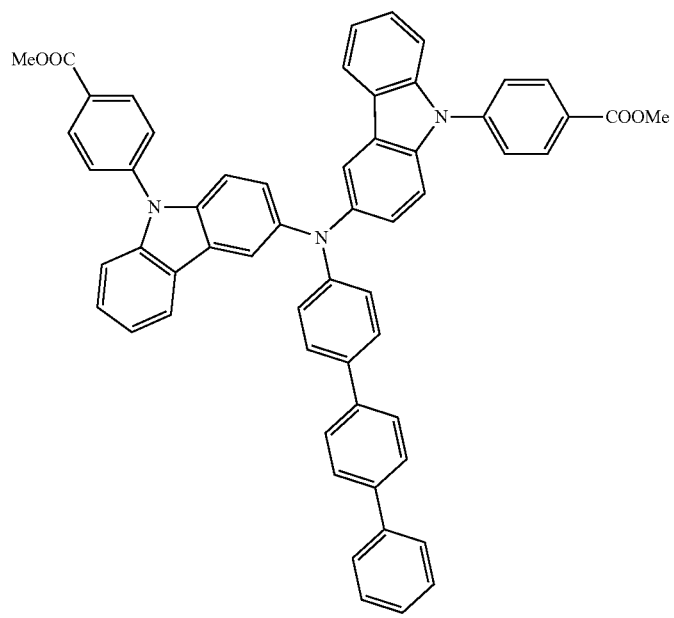

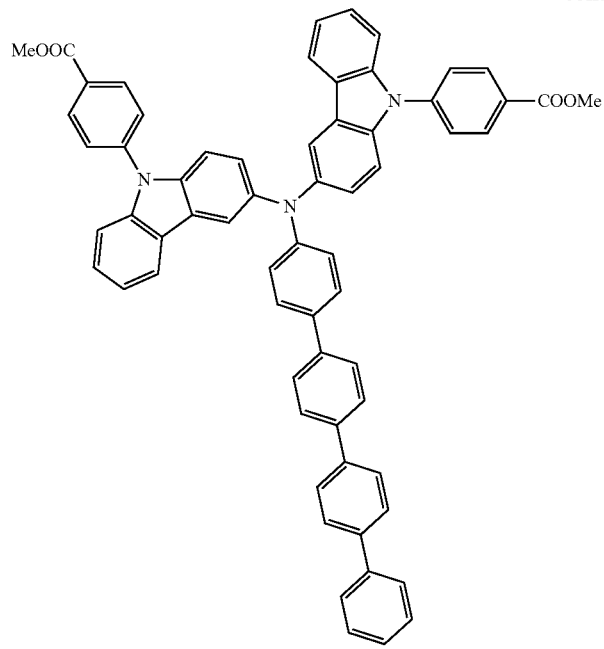
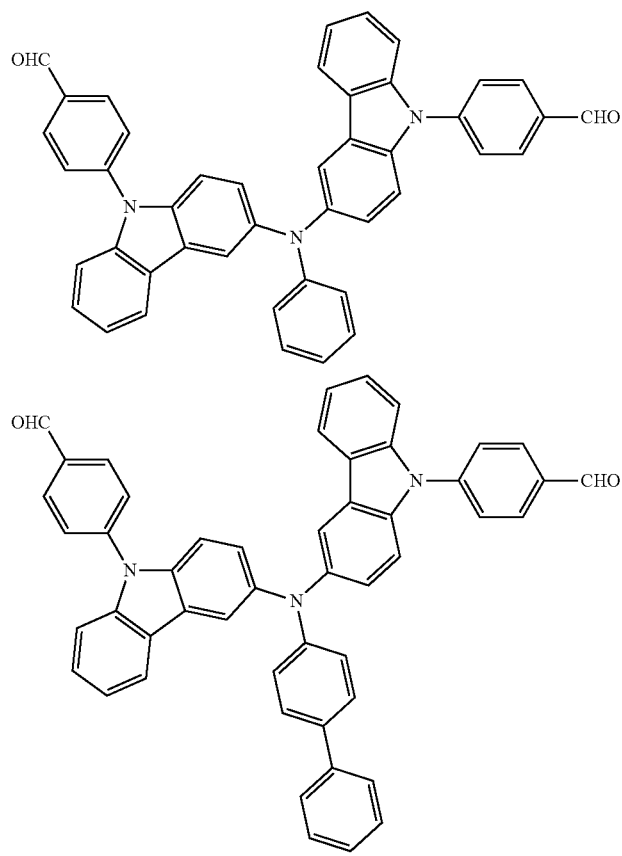

-continued
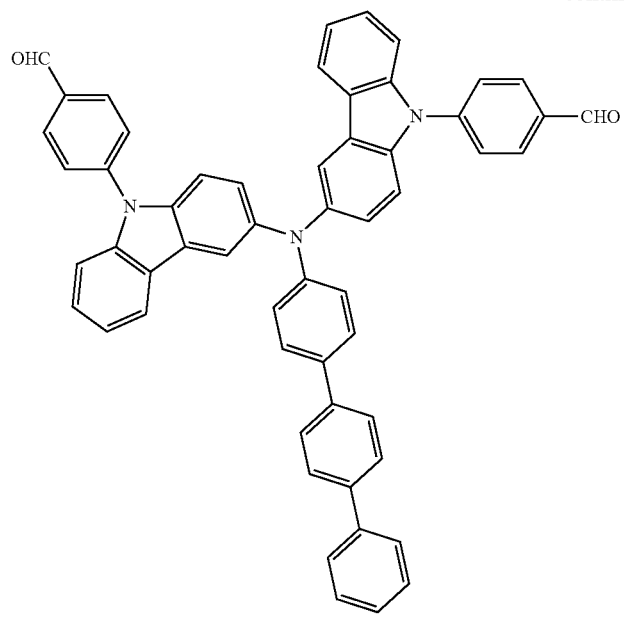
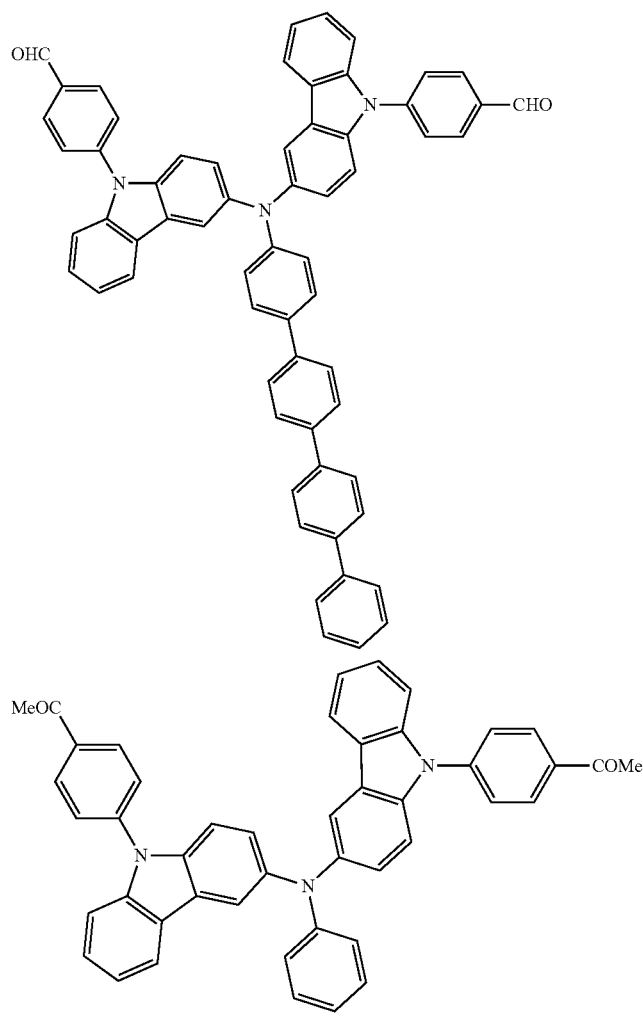

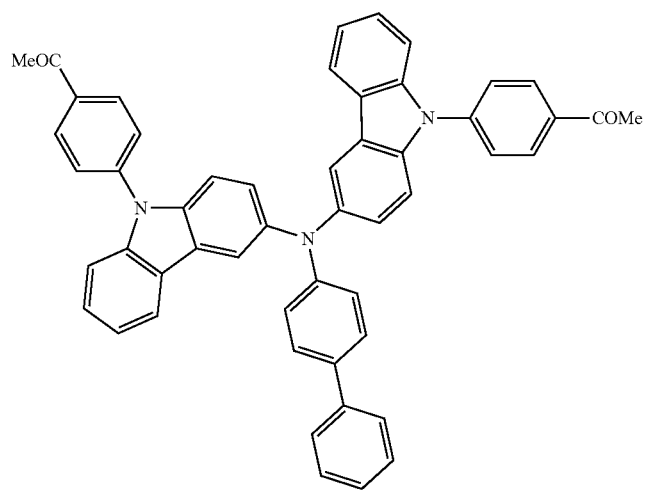
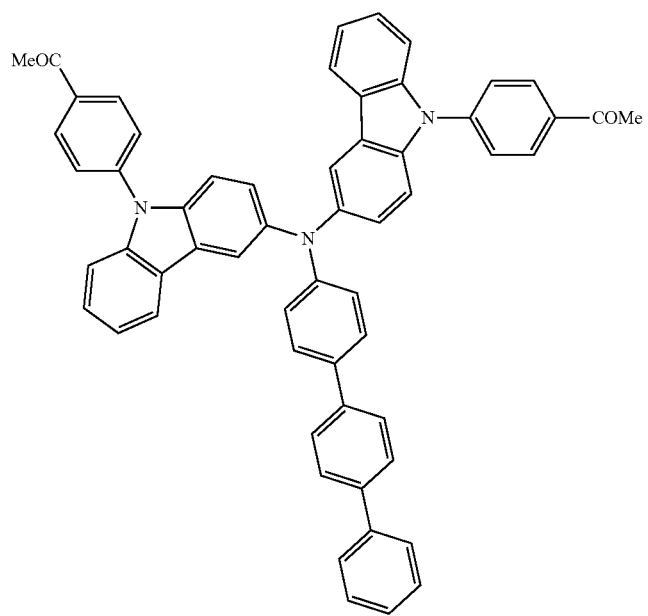

-continued
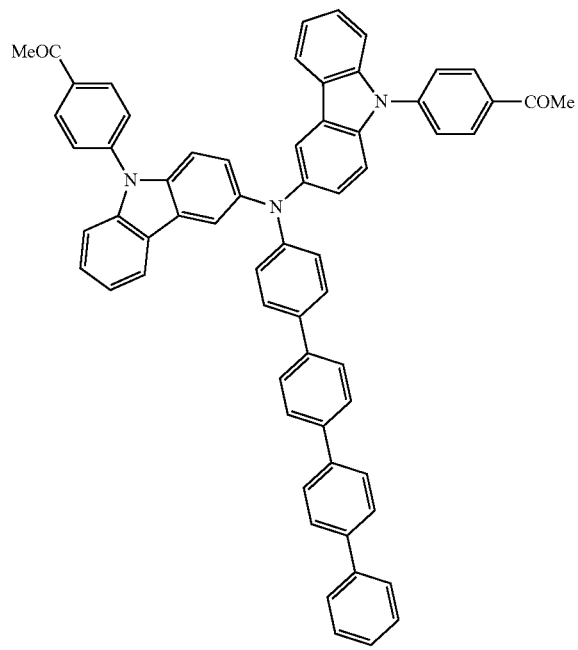
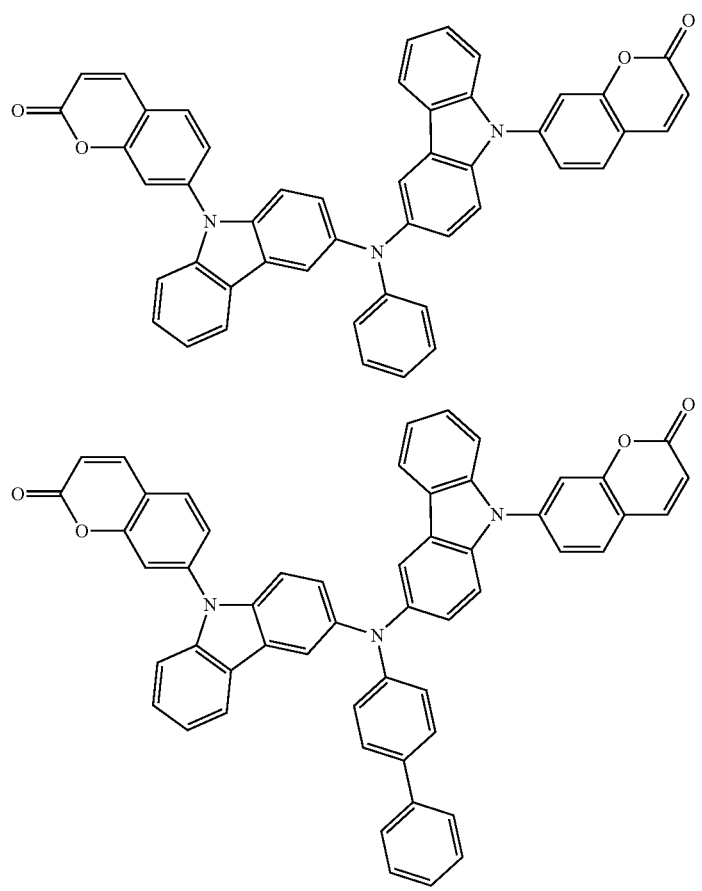

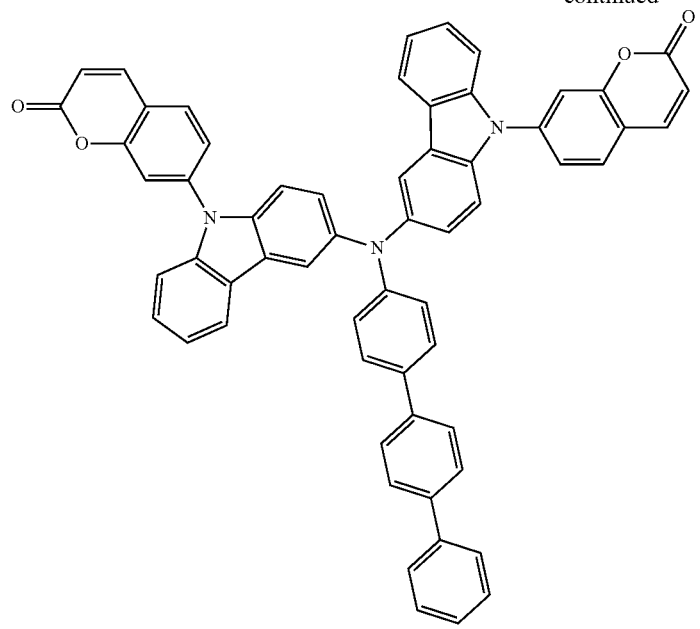
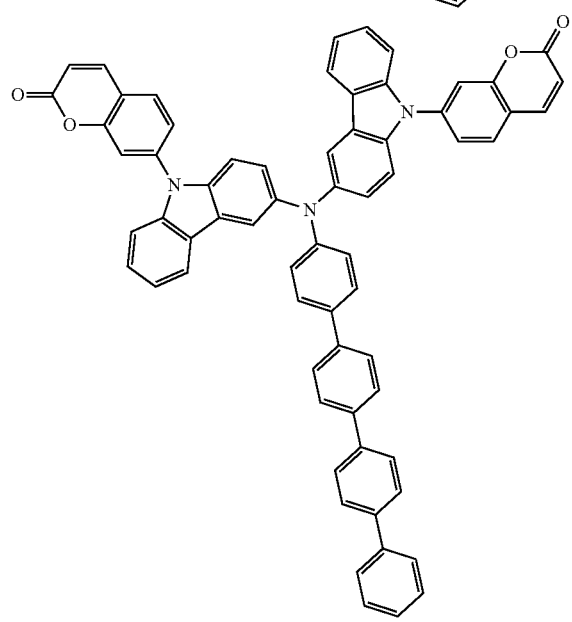
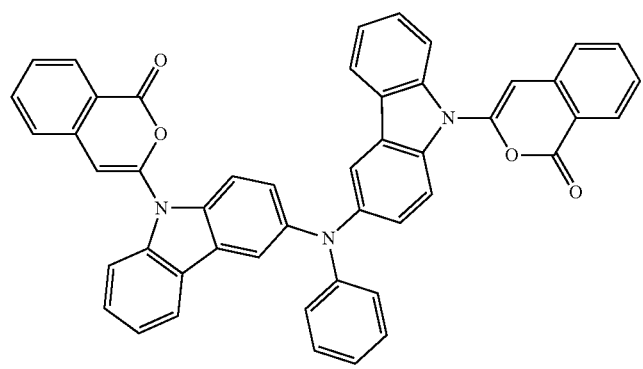

-continued
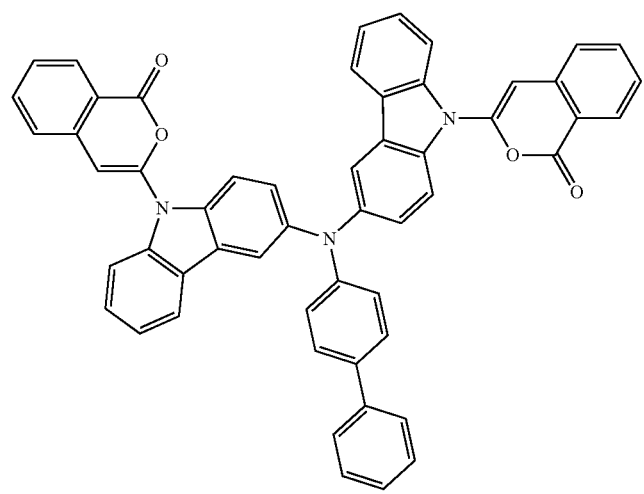
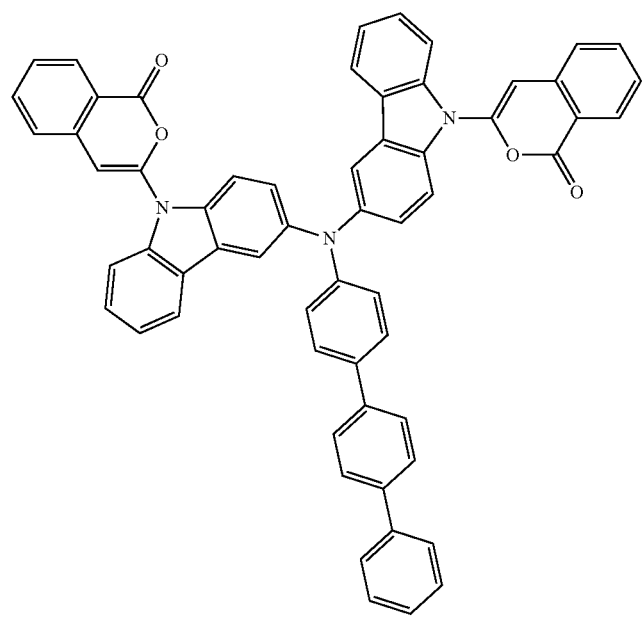
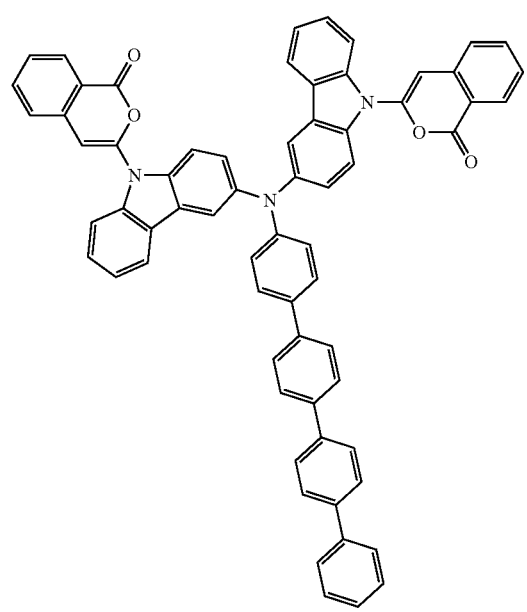
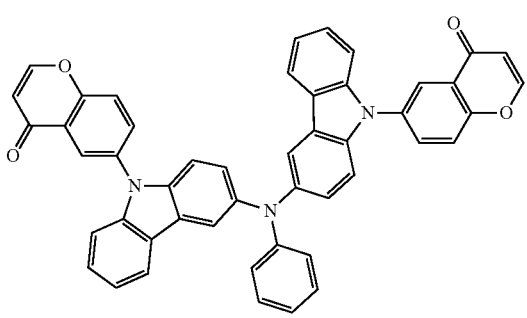

-continued
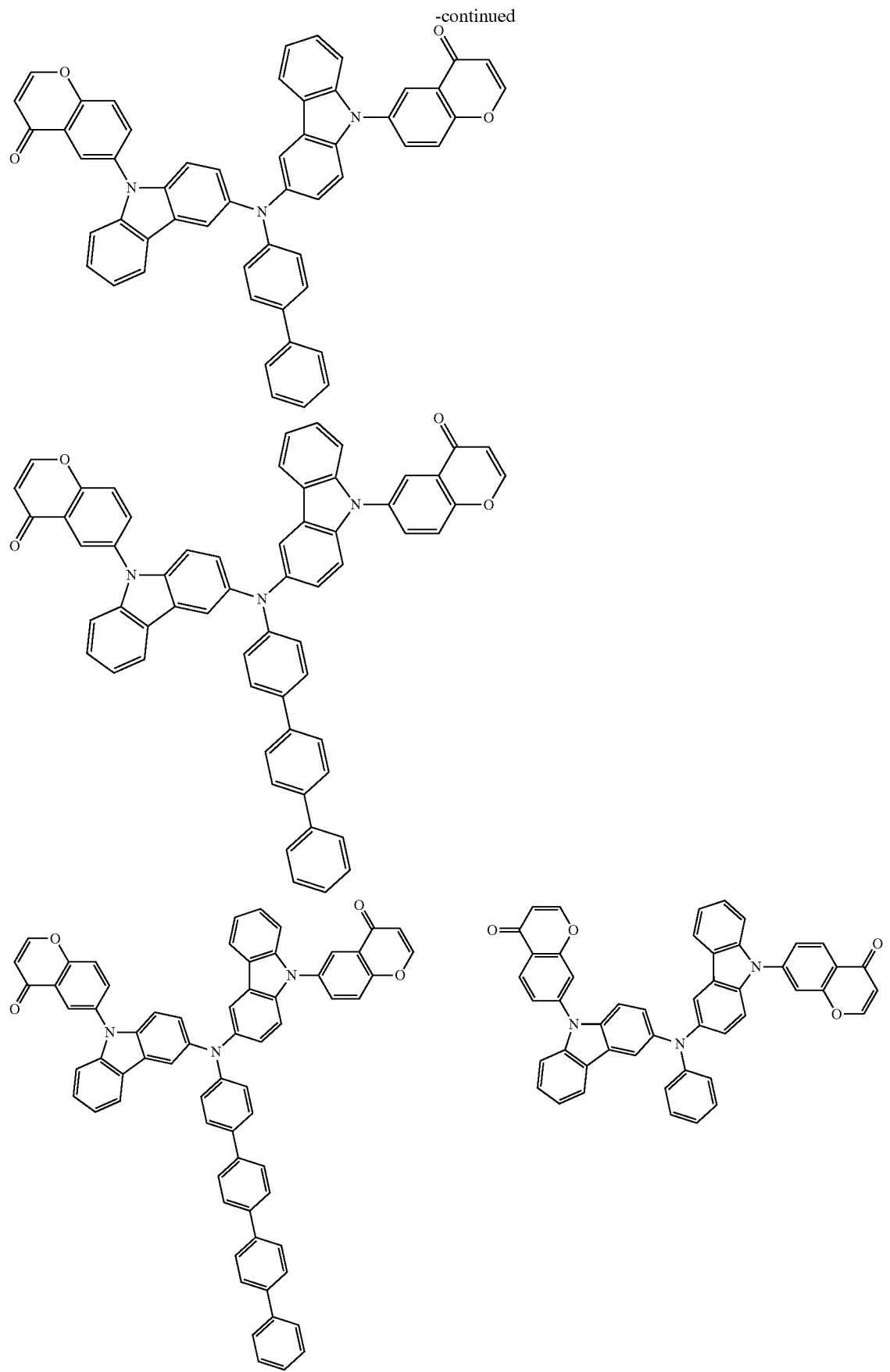

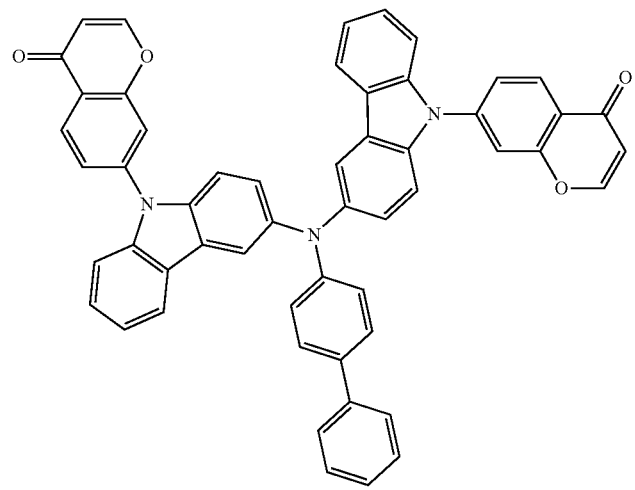
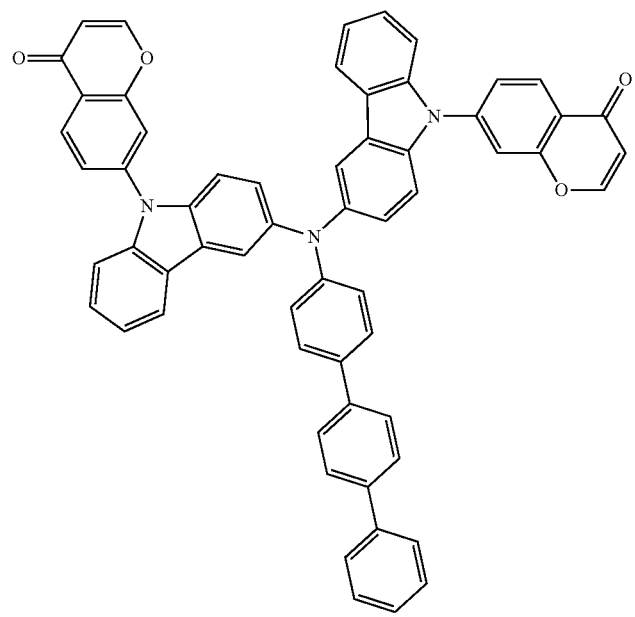

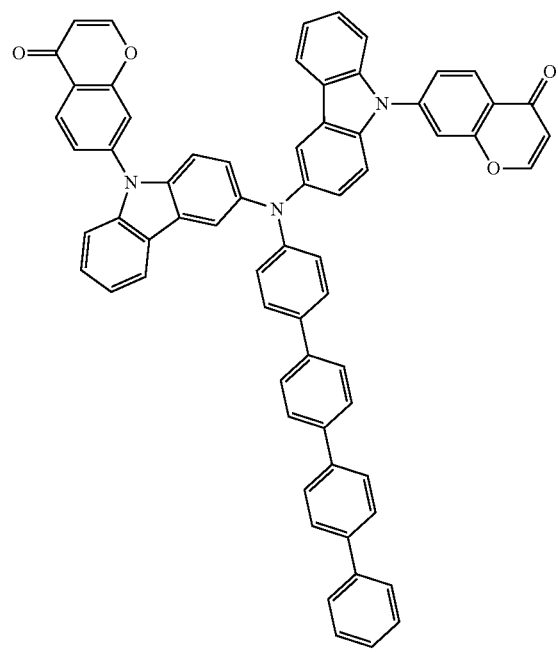
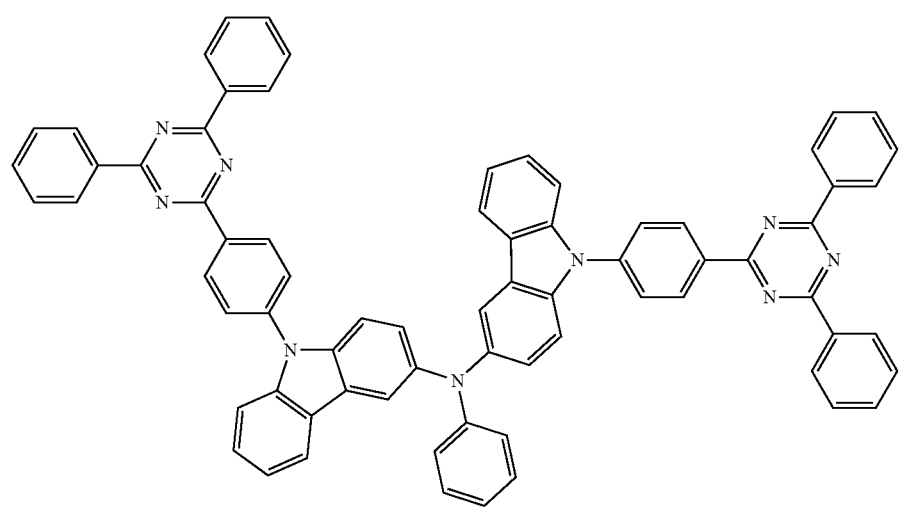

-continued
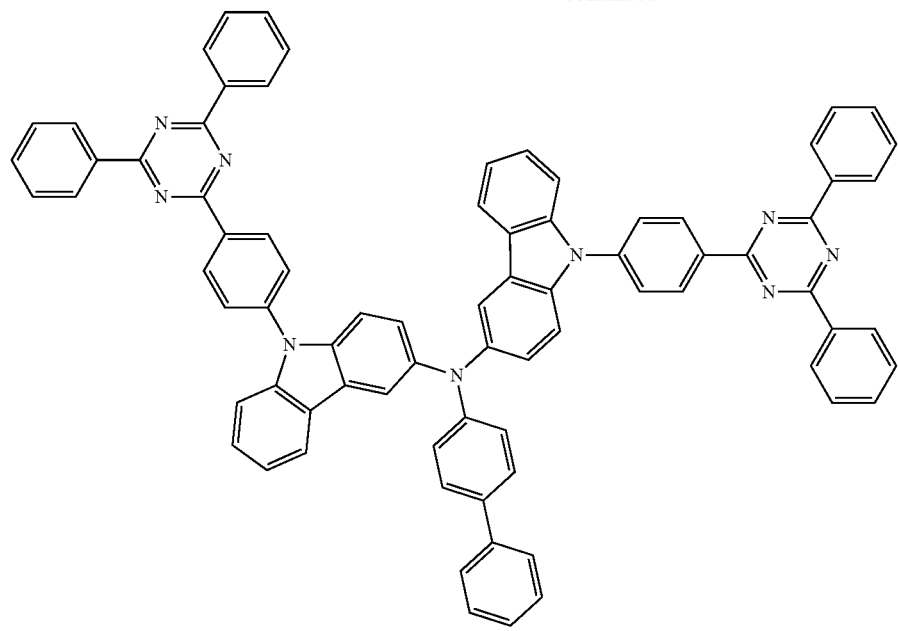
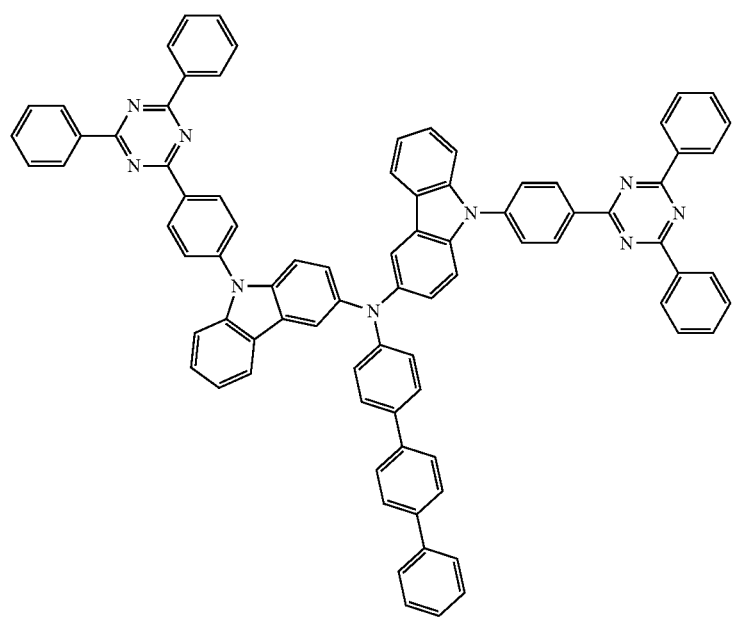

-continued
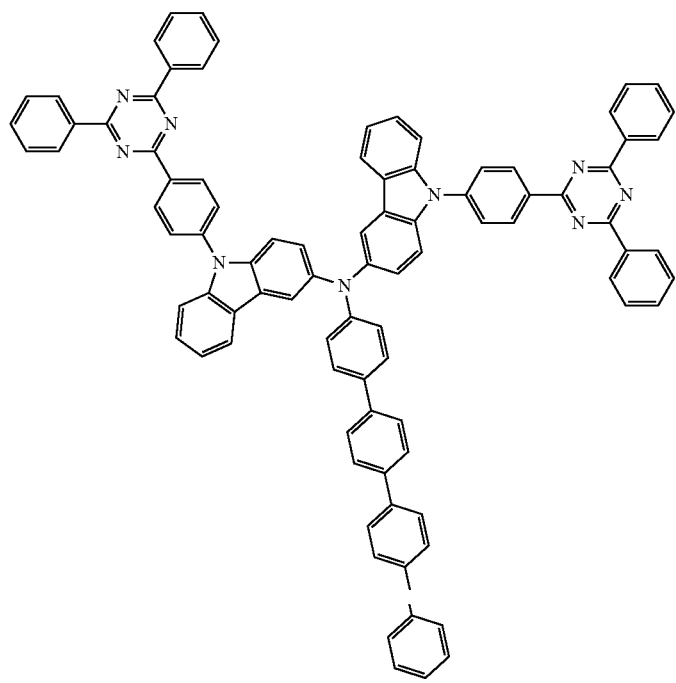
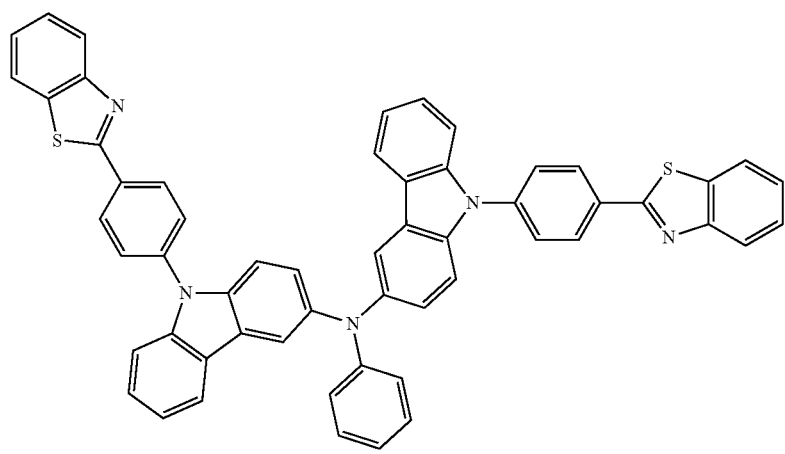
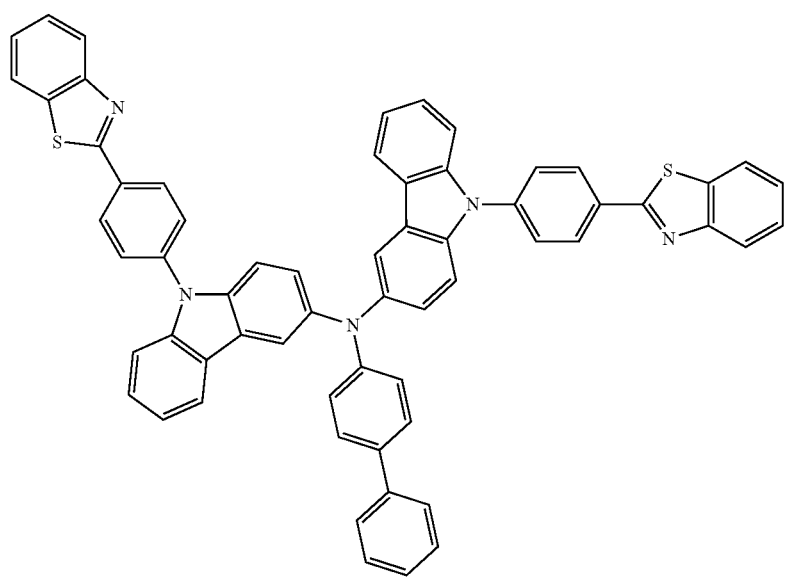

-continued
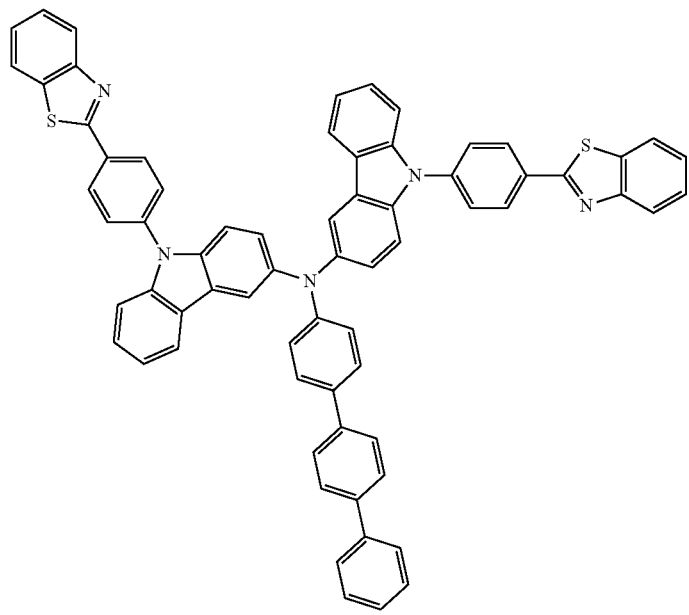
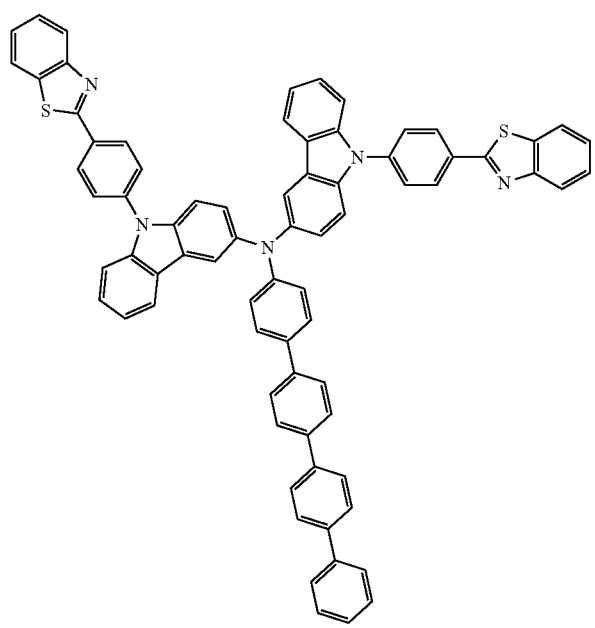
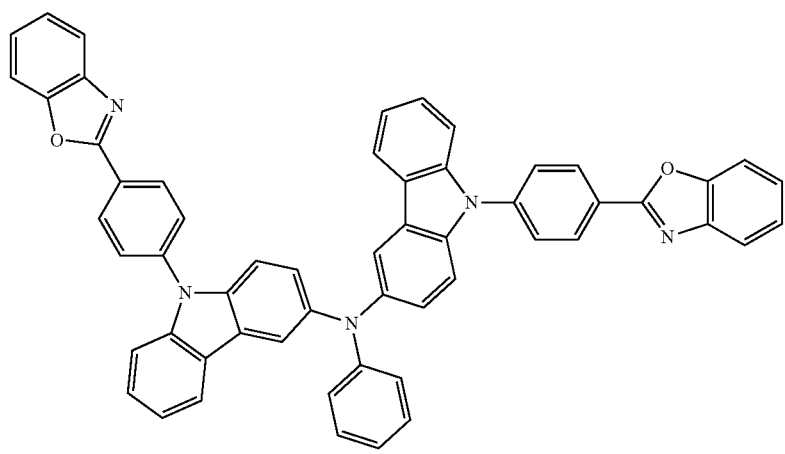

-continued
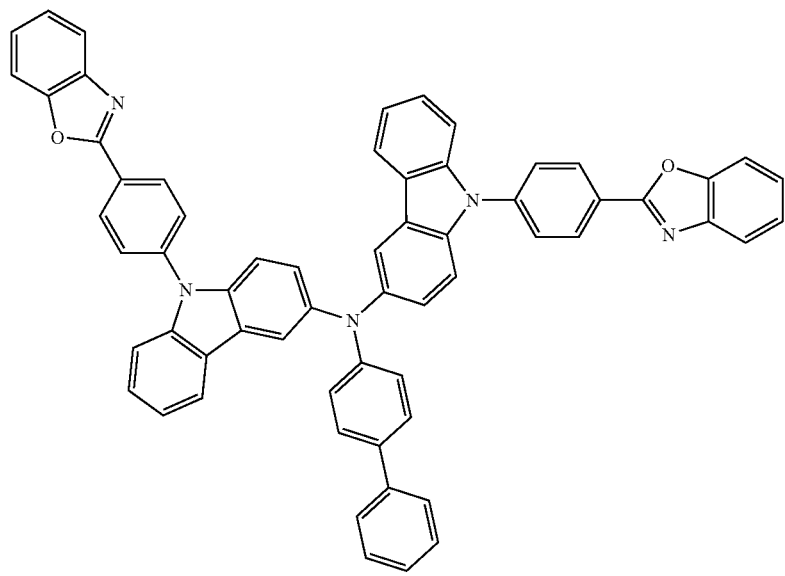
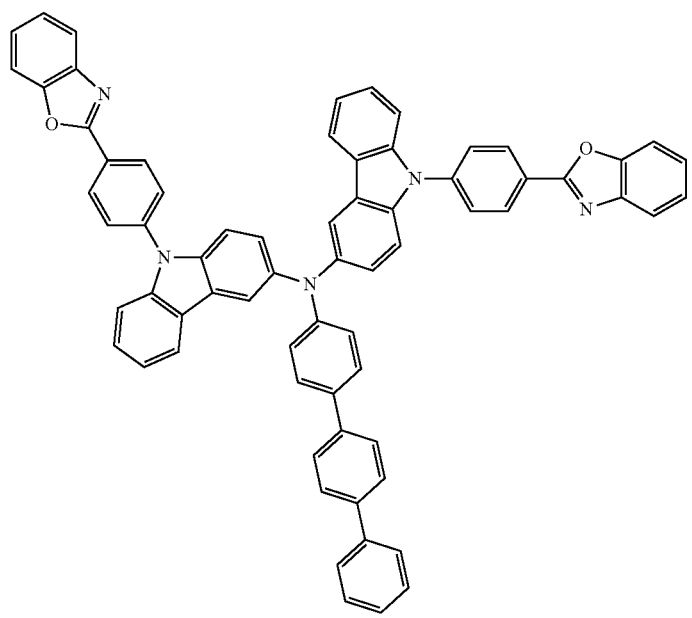

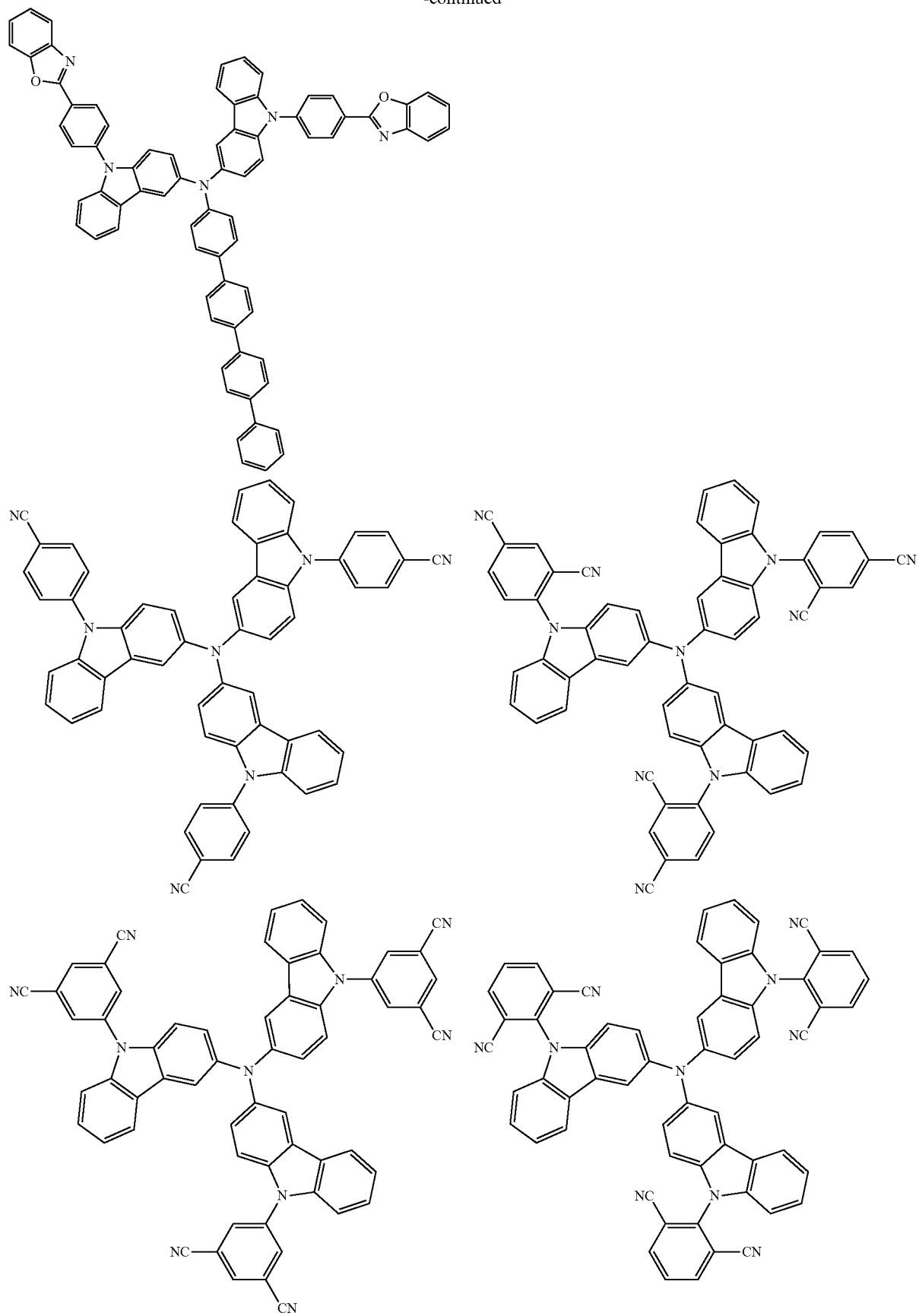

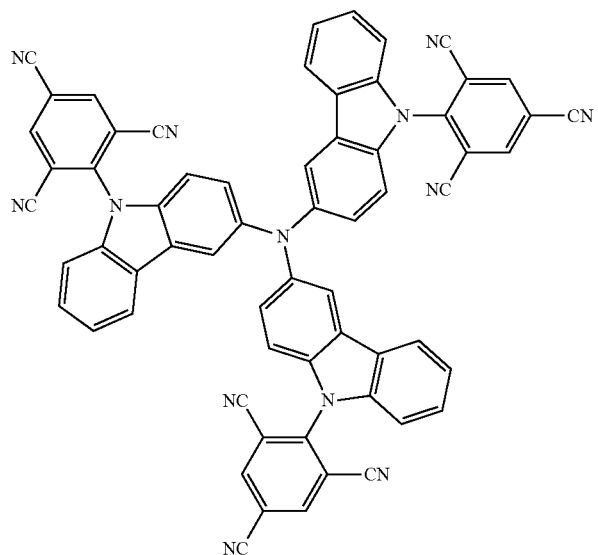
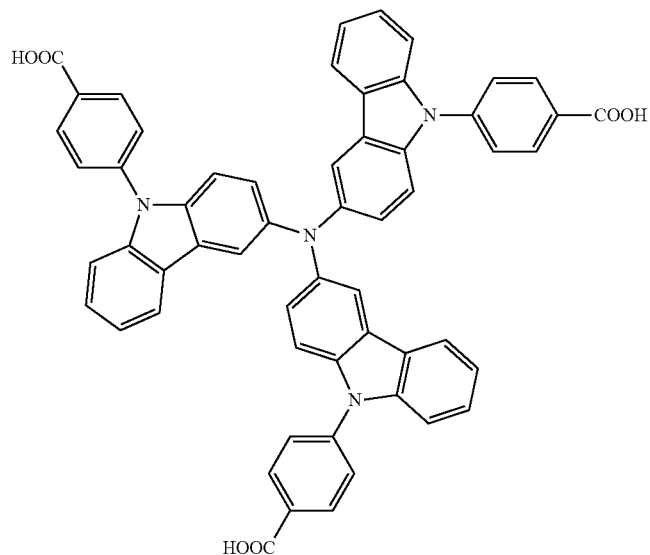
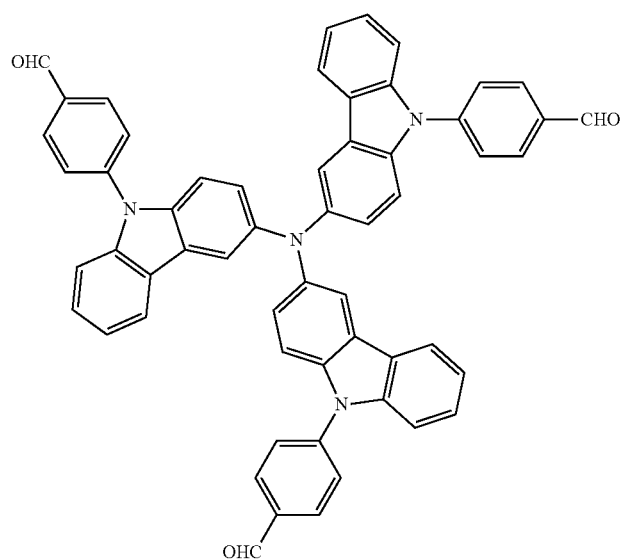

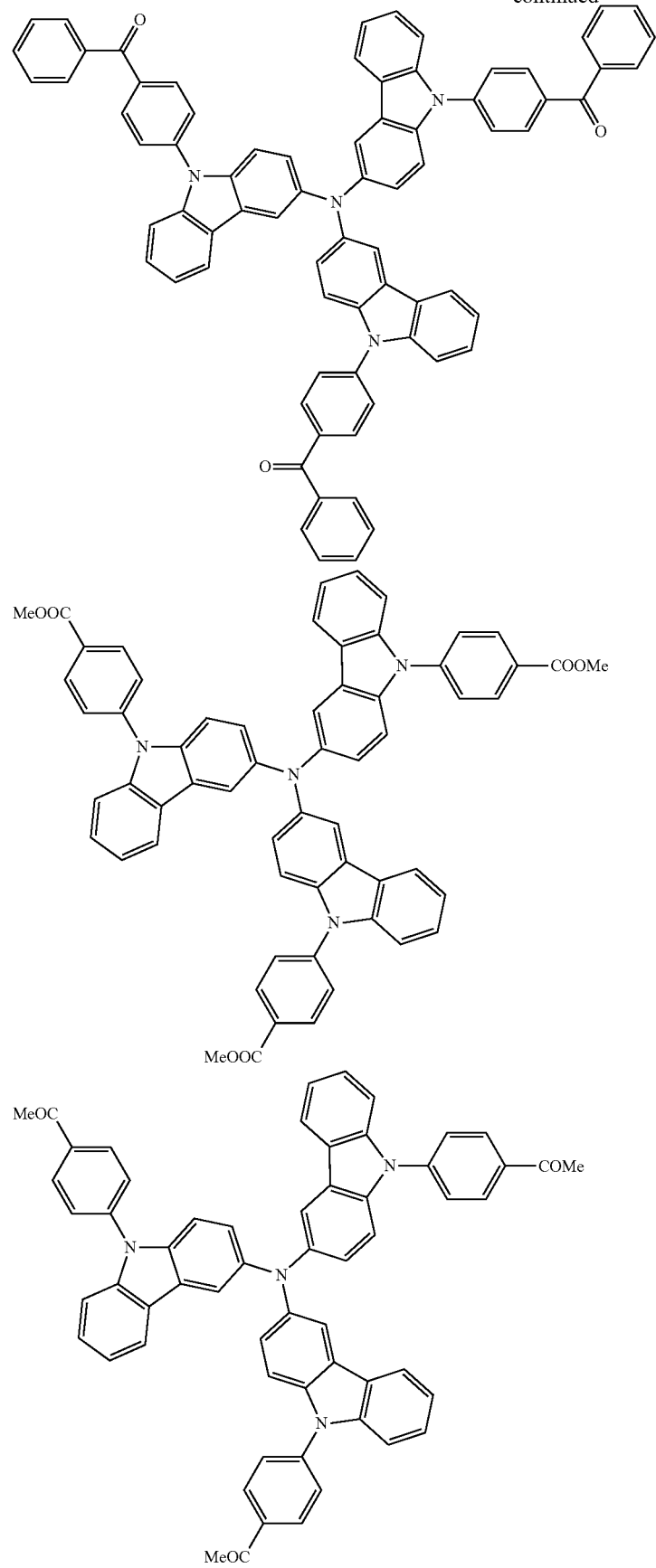

-continued
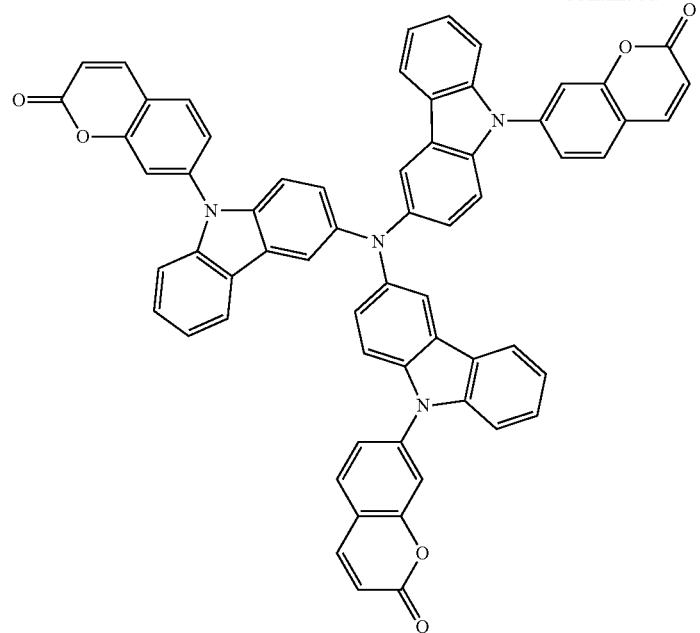
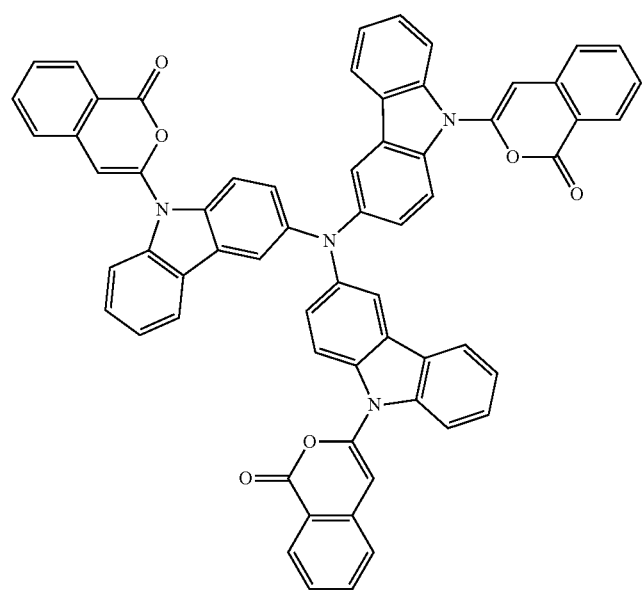

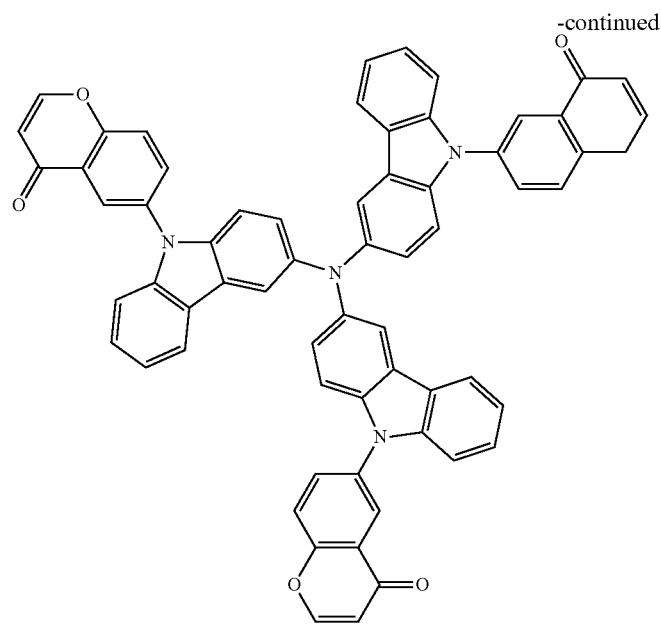
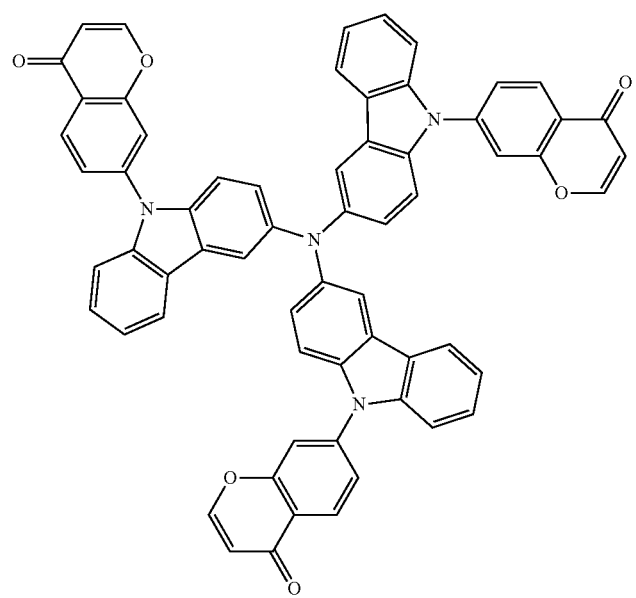

-continued
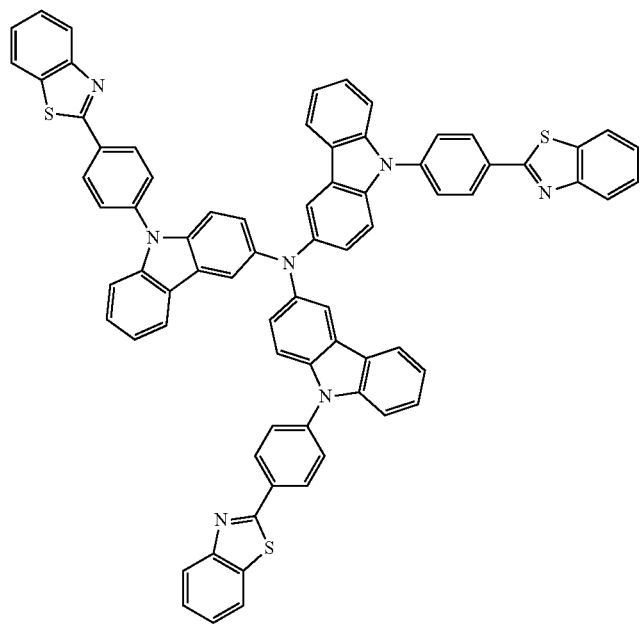
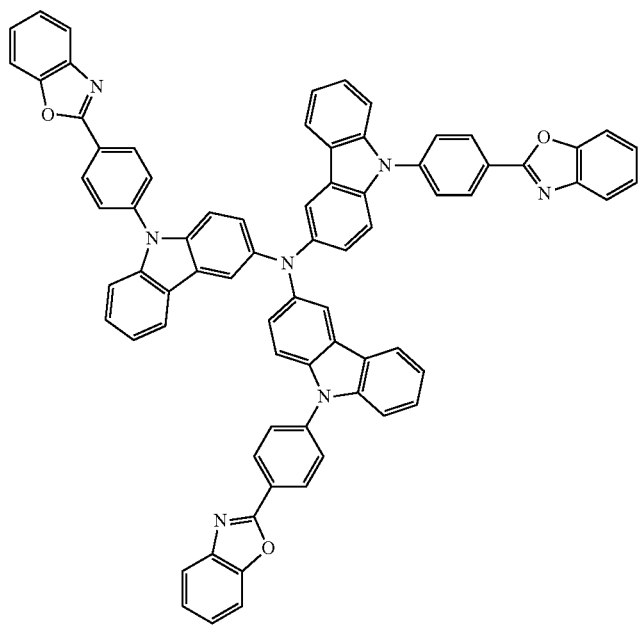

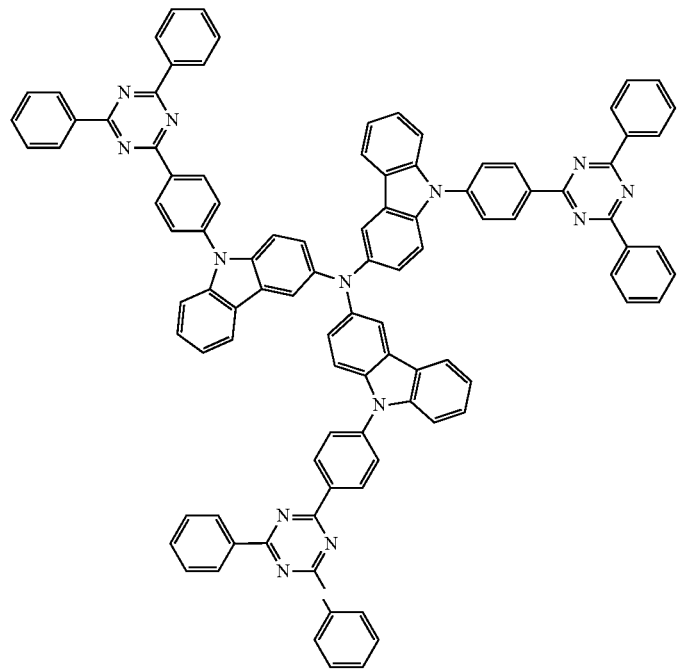
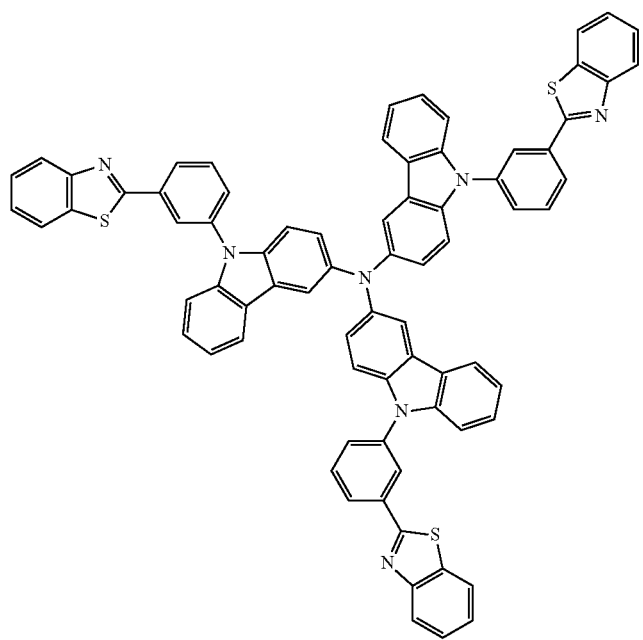

-continued
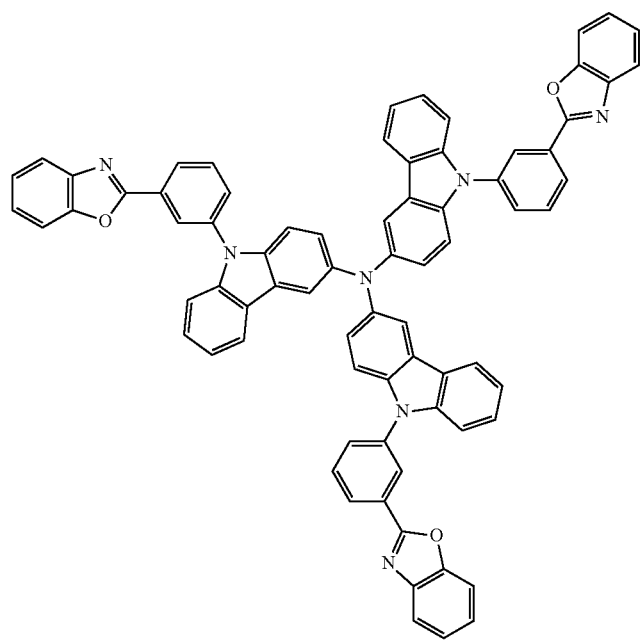
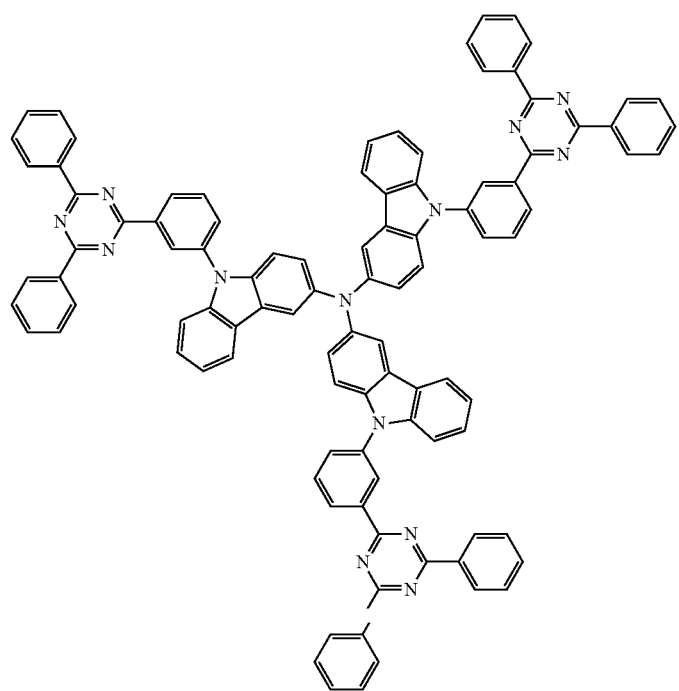

-continued
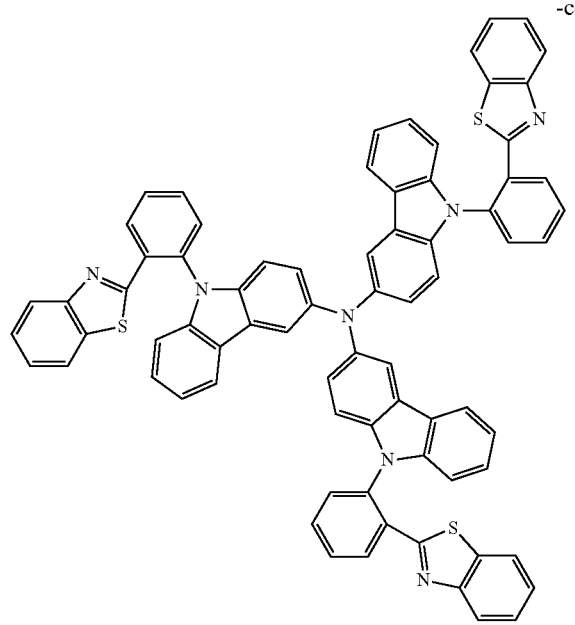
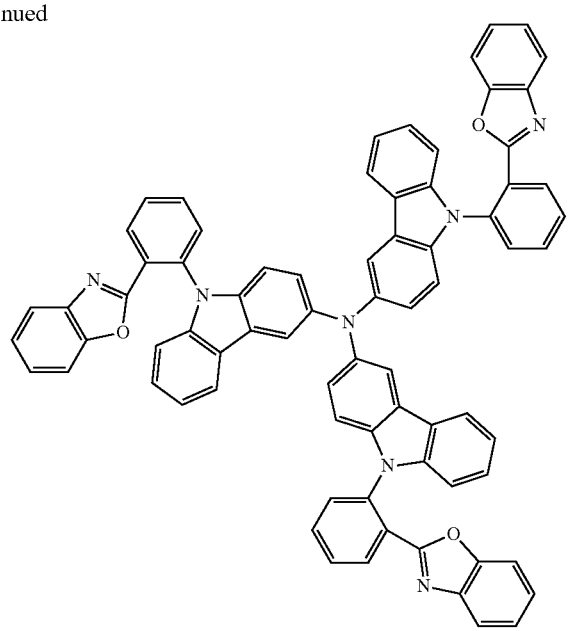
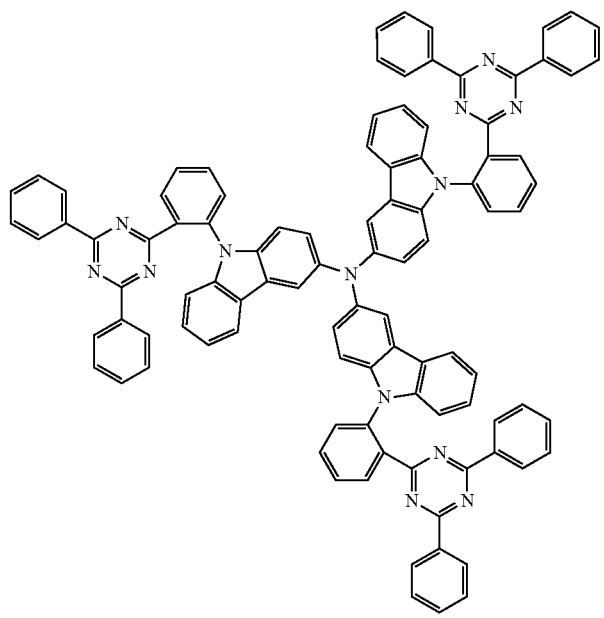

-continued
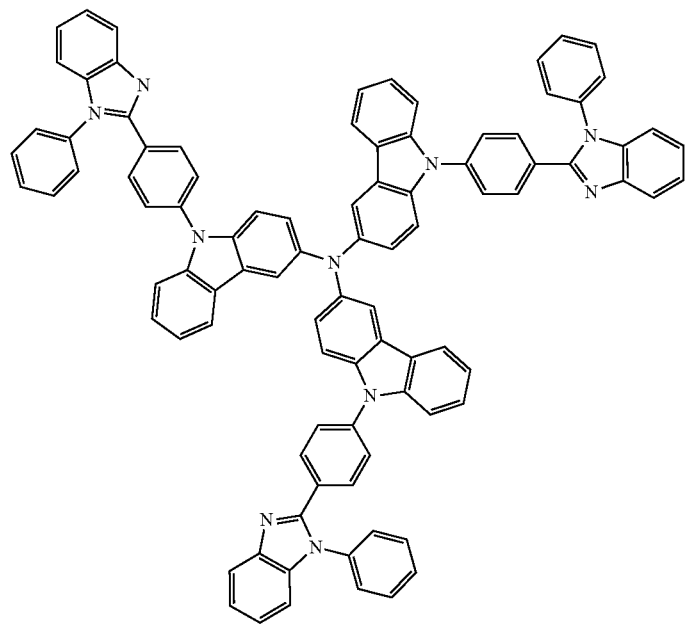
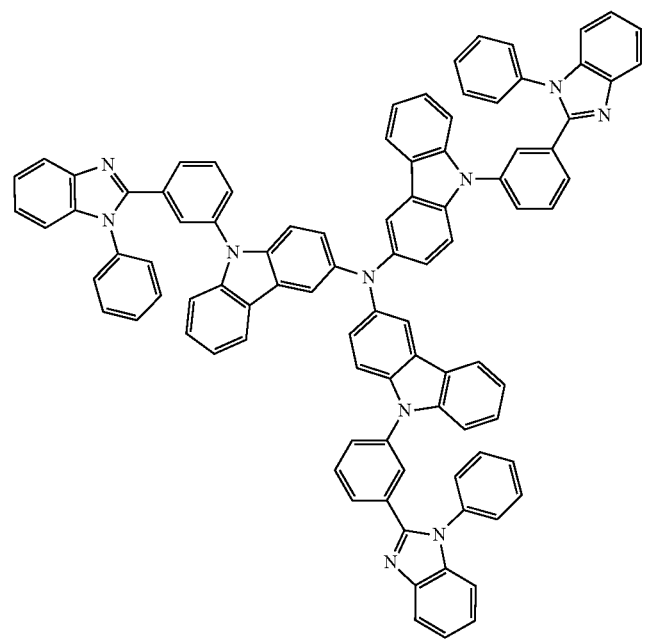

-continued

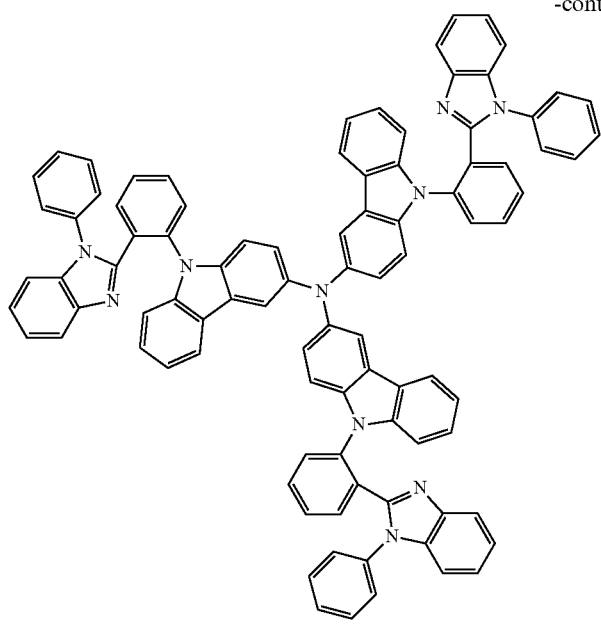

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light-emitting material.

For example, it may be considered that a polymerizable group is introduced in advance to the structure represented by the general formula (1), and a polymer obtained by polymerizing the polymerizable group is used as a light-emitting material. Specifically, it may be considered that a monomer that has a polymerizable functional group at any of $Ar^1$ to $Ar^4$ in the general formula (1) is prepared, and is homopolymerized or copolymerized with another monomer to prepare a polymer containing repeating units, and the polymer is used as a light-emitting material. In alternative, it may be considered that the compounds represented by the general formula (1) are reacted to form a dimer or a trimer, and the dimer or the trimer is used as a light-emitting material.

Examples of the polymer having the repeating unit containing the structure represented by the general formula (1) include a polymer containing a structure represented by the following general formula (3) or (4).

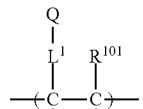
General Formula (3)

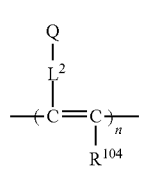
General Formula (4)

In the general formulae (3) and (4), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $—X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (3) and (4), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $Ar^1$ to $Ar^3$ in the structure of the general formula (1) or any of $R^1$ to $R^7$ and $R^{11}$ to $R^{15}$ in the structure represented by the general formula (2) constituting Q. Two or more of the linking groups may be bonded to one group represented by Q to form a crosslinked structure or a network structure.

Specific examples of the structure of the repeating unit include structures represented by the following formulae (5) to (8).

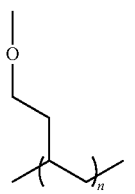

Gereral Formula (5)

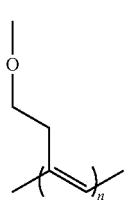

Gereral Formula (6)

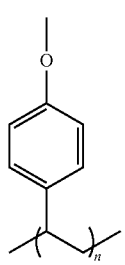

Gereral Formula (7)

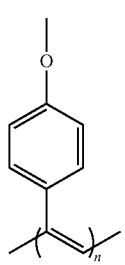

Gereral Formula (8)

The polymer having the repeating unit containing the structure represented by any of the formulae (5) to (8) may be synthesized in such a manner that a hydroxy group is introduced to any of $Ar^1$ to $Ar^3$ in the structure represented by the general formula (1), and the hydroxy group as a linker is reacted with the following compound to introduce a polymerizable group thereto, followed by polymerizing the polymerizable group.

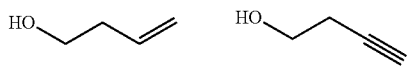

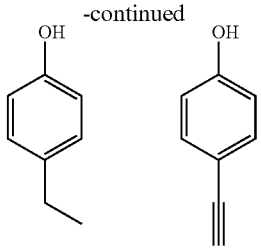

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound represented by General Formula (1')

The compound represented by the general formula (1') is a novel compound.

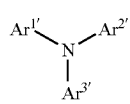

General Formula (1')

In the general formula (1'), $Ar^{1'}$ to $Ar^{3'}$ each independently represent a substituted or unsubstituted aryl group, provided that at least one of $Ar^{1'}$ to $Ar^{3'}$ each independently represent a carbazolyl group having an N-position substituted with a group containing an electron withdrawing group.

For the descriptions and the preferred ranges of $Ar^{1'}$ to $Ar^{3'}$ in the general formula (1'), reference may be made to the descriptions for the compound represented by the general formula (1).

Synthesis Method of Compound Represented by General Formula (1')

The compound represented by the general formula (1') may be synthesized by combining the known reactions. For example, a compound represented by the general formula (1'), in which $Ar^{1'}$ and $Ar^{2'}$ each represent a group represented by the general formula (2), and $R^{13}$ represents an electron withdrawing group, can be synthesized by reacting the following two compounds.

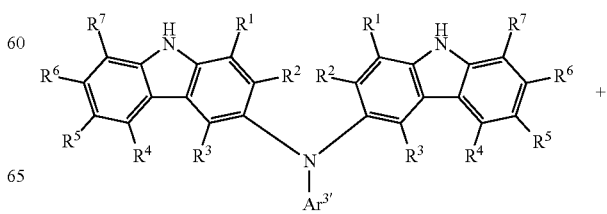

-continued

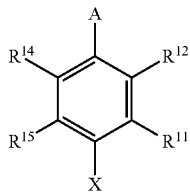

For the description of Ar$^{3\dagger}$, R$^1$ to R$^7$, R$^{11}$, R$^{12}$, R$^{14}$, and R$^{15}$ in the reaction scheme, reference may be made to the corresponding description in the general formula (1'). A represents an electron withdrawing group. For the preferred examples of the electron withdrawing group, reference may be made to the preferred examples of the electron withdrawing group that may be represented by R$^{11}$ to R$^{15}$. X represents a halogen atom, examples of which include a fluorine atom, a chlorine atom, a bromine atom, and an iodine atom, and a chlorine atom, a bromine atom, and an iodine atom are preferred.

The reactions in the aforementioned scheme each are an application of the known reactions, and the known reaction conditions may be appropriately selected and used. For the details of the reactions, reference may be made to the synthesis examples described later. The compound represented by the general formula (1') may also be synthesized by combining the other known synthesis reactions.

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) includes a delayed fluorescent emitter emitting delayed fluorescent light. Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescence device as an example.

In an organic electroluminescence device, carriers are injected from an anode and a cathode to a light-emitting material to form an excited state for the light-emitting material, with which light is emitted. In the case of a carrier injection type organic electroluminescence device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent emitter emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent emitter emitting light through absorption of thermal energy is particularly useful for an organic electroluminescence device. In the case where a delayed fluorescent emitter is used in an organic electroluminescence device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescence device (organic PL device) and an organic electroluminescence device (organic EL device). At this time, the compound represented by the general formula (1) of the invention may have a function of assisting light emission of another light-emitting material contained in the light-emitting layer, i.e., as a so-called assist dopant. Specifically, the compound represented by the general formula (1) of the invention contained in the light-emitting layer may have a lowest excited singlet energy level that is between the lowest excited singlet energy level of the host material contained in the light-emitting layer and the lowest excited singlet energy level of the another light-emitting material contained in the light-emitting layer.

The organic photoluminescent device has a structure containing a substrate having formed thereon at least a light-emitting layer. The organic electroluminescence device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescence device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescence device will be described below. The descriptions for the substrate and the light-emitting layer may also be applied to the substrate and the light-emitting layer of the organic photoluminescent device.

Substrate

The organic electroluminescence device of the invention is preferably supported by a substrate. The substrate is not particularly limited and may be those that have been commonly used in an organic electroluminescence device, and examples thereof used include those formed of glass, transparent plastics, quartz and silicon.

Anode

The anode of the organic electroluminescence device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescence device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescence device and the organic photoluminescence device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescence device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescence device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescence device are shown below, but the materials that may be used in the invention are not construed as being limited to the example compounds. The compound that is shown as a material having a particular function may also be used as a material having another function. In the structural formulae of the example compounds, R and $R_1$ to $R_{10}$ each independently represent a hydrogen atom or a substituent, and n represents an integer of from 3 to 5.

Preferred examples of a compound that may also be used as the host material of the light-emitting layer are shown below.

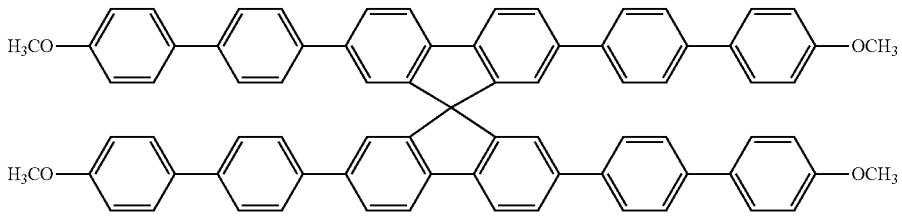

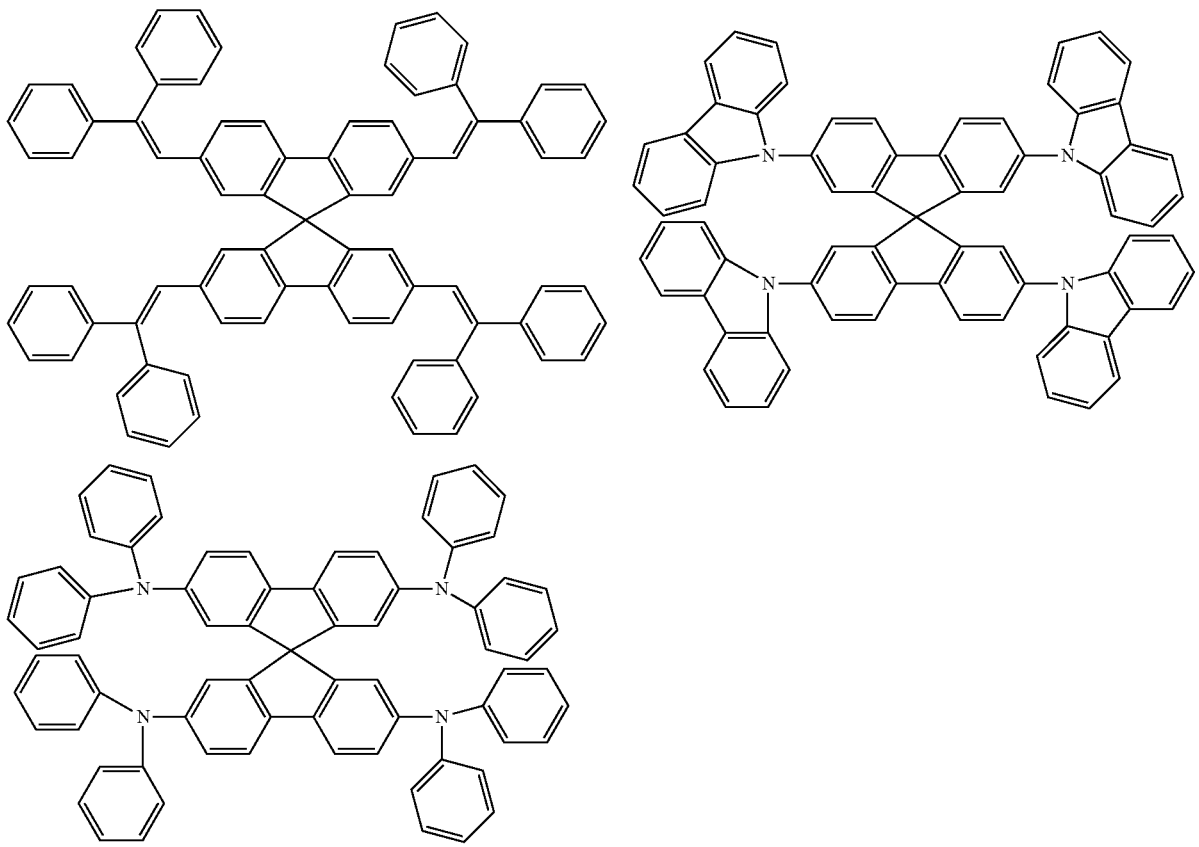

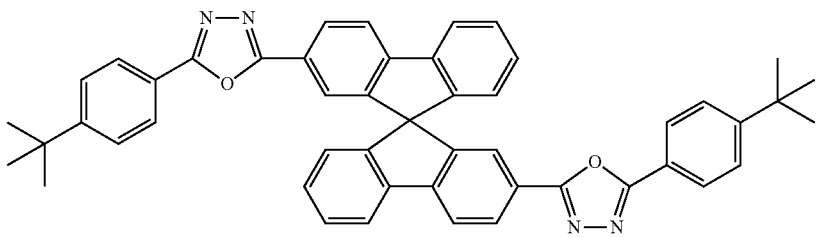

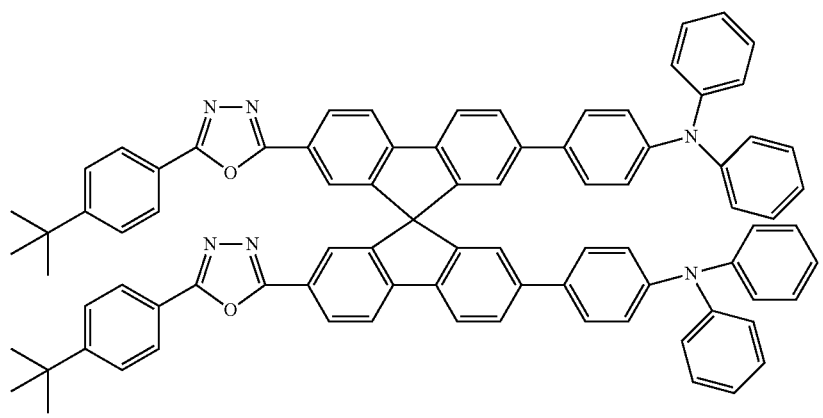
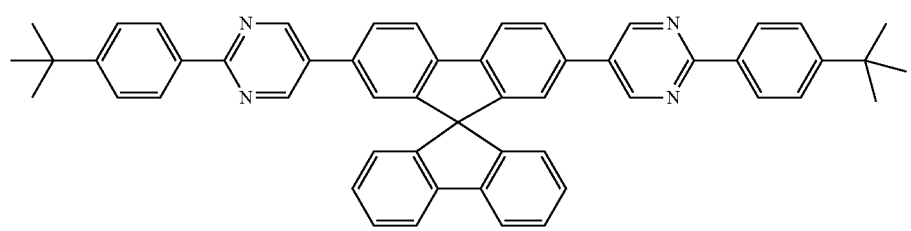
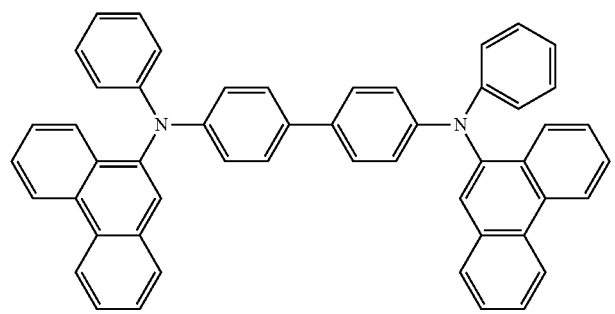
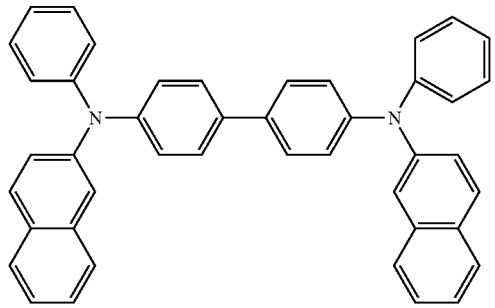
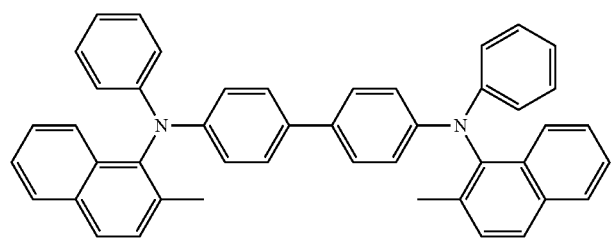
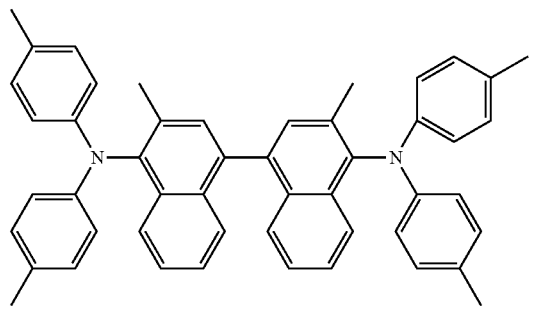

-continued
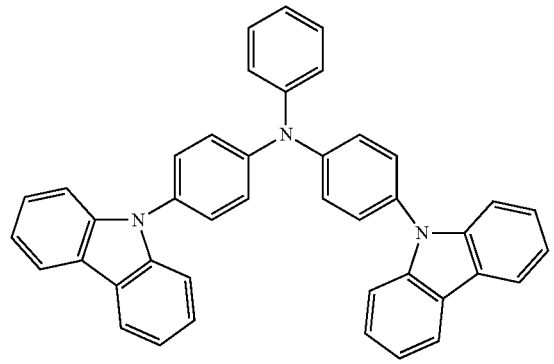
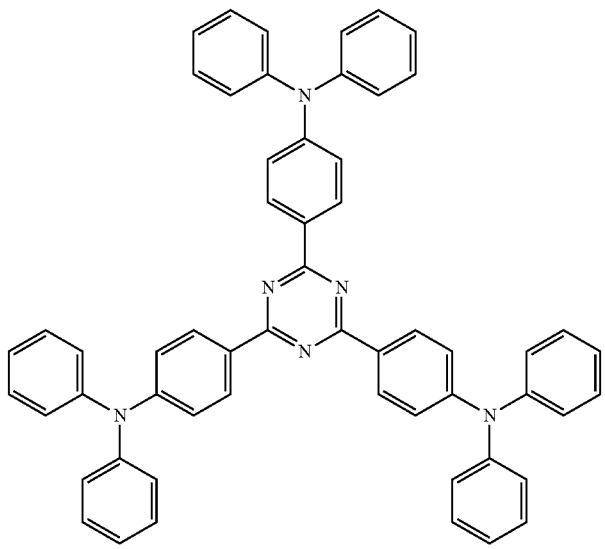
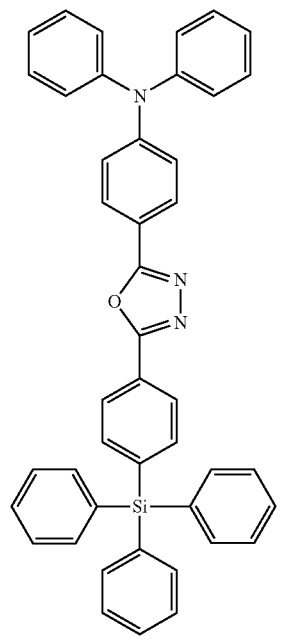
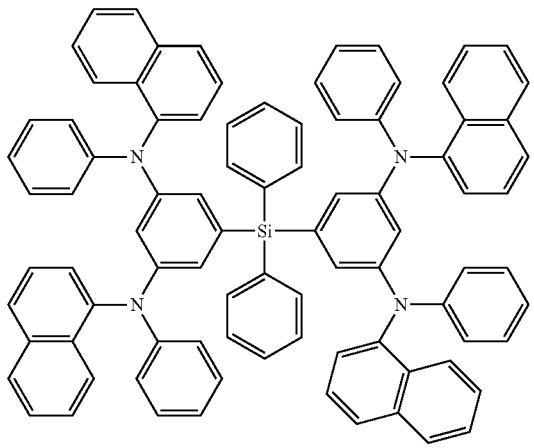
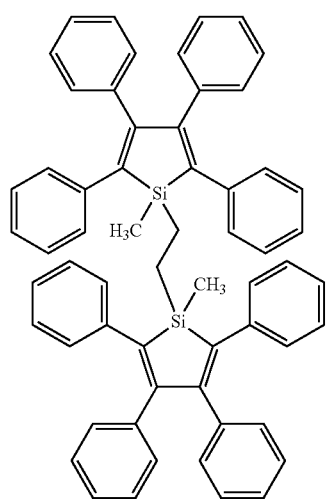
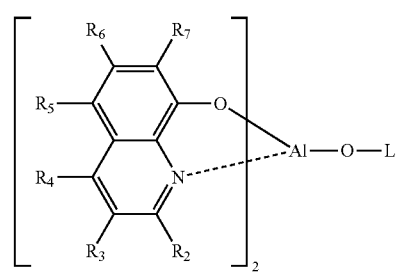

87
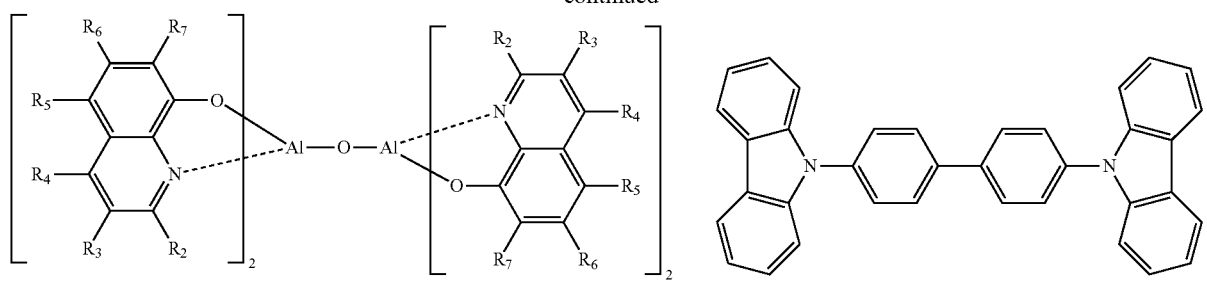
-continued
88
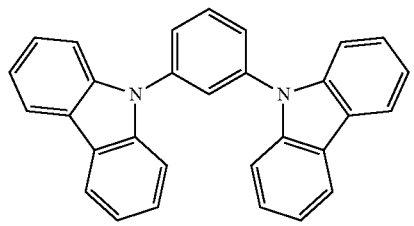
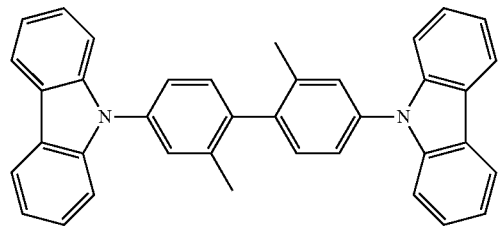
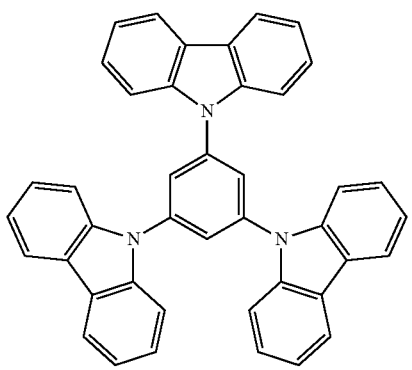
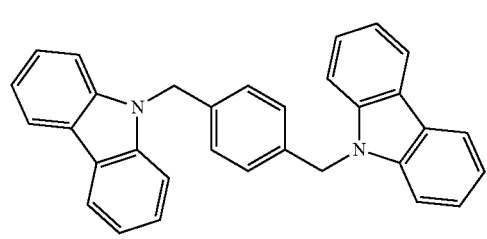
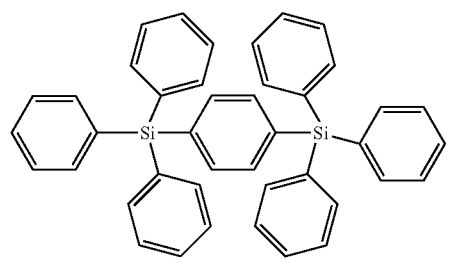
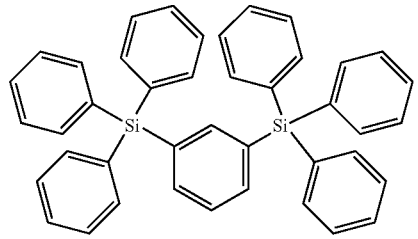
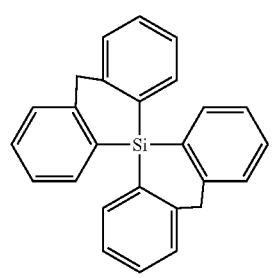
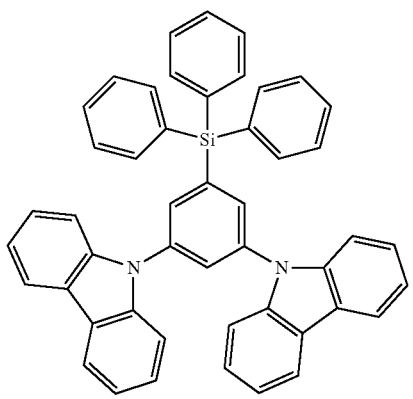

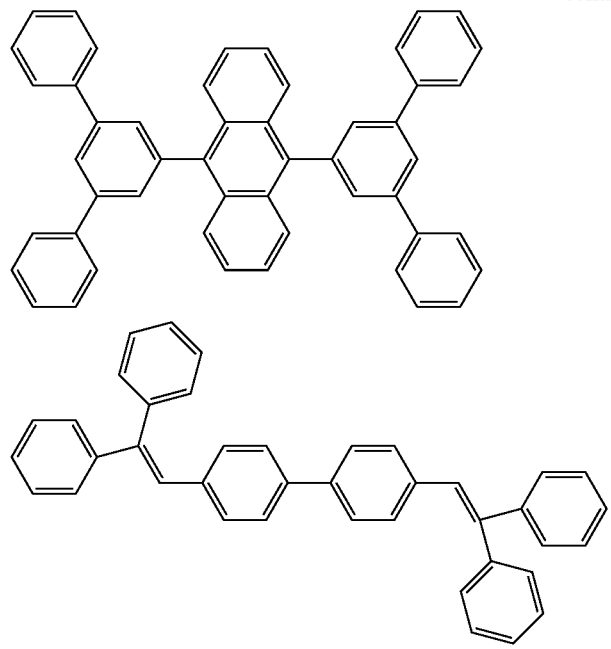
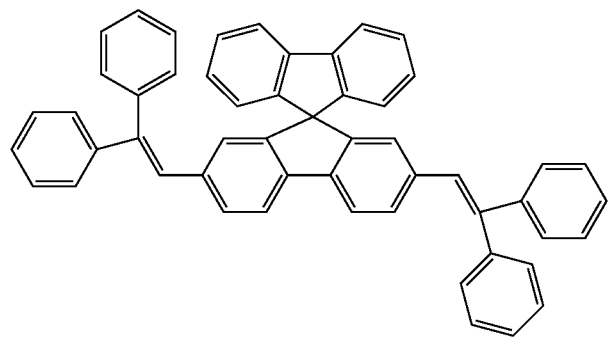
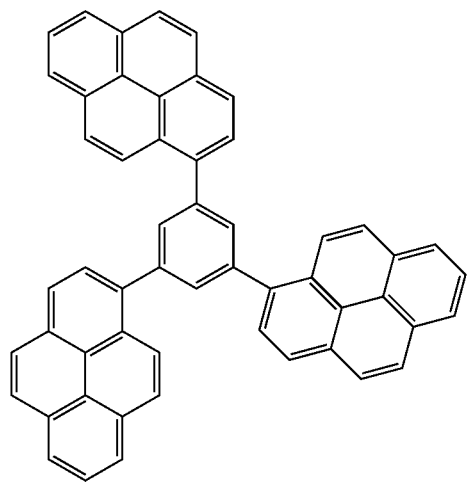
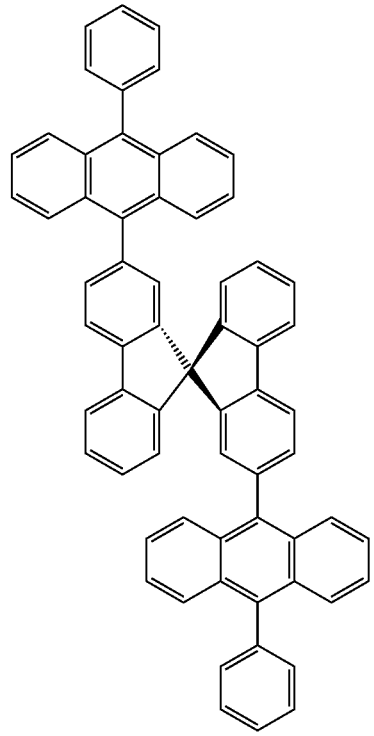

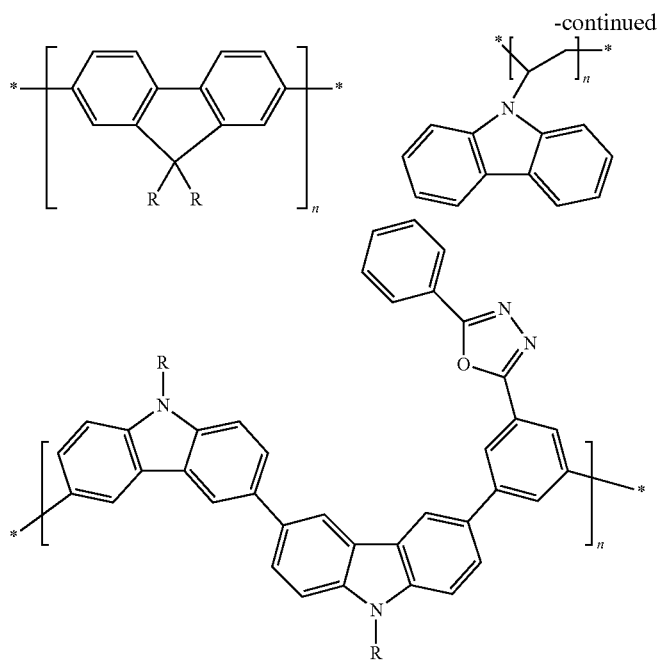
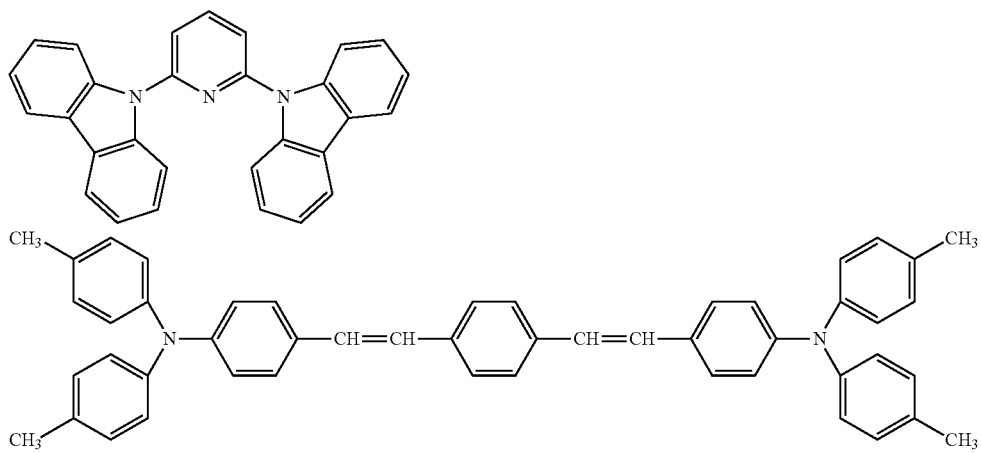
Preferred examples of a compound that may be used as the hole injection material are shown below.
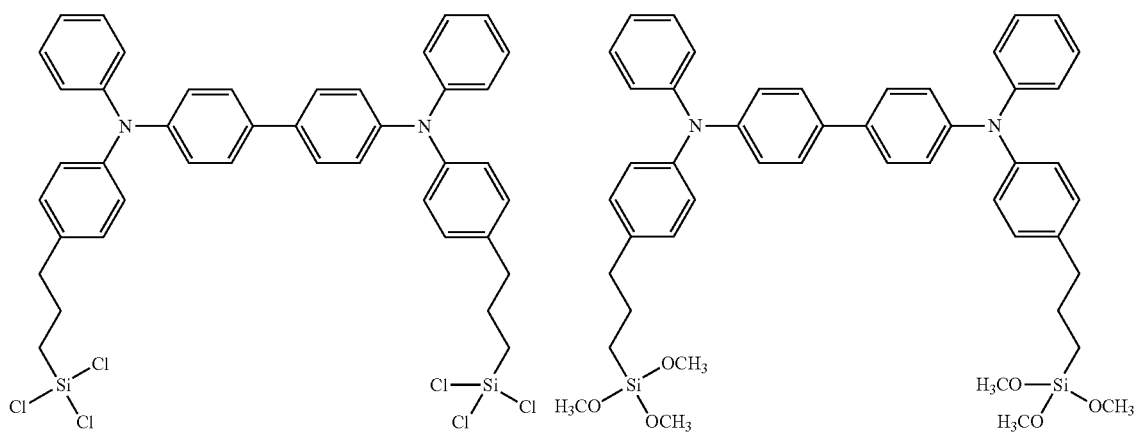

-continued
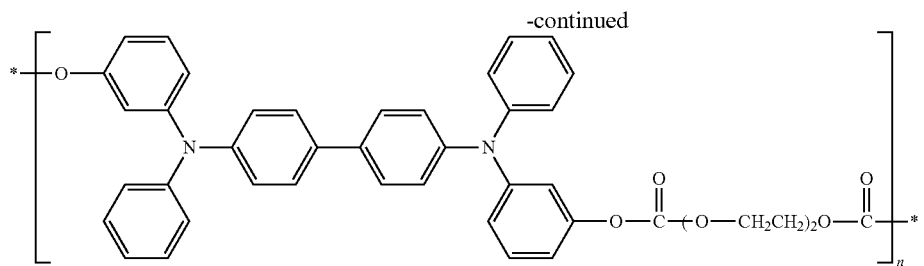
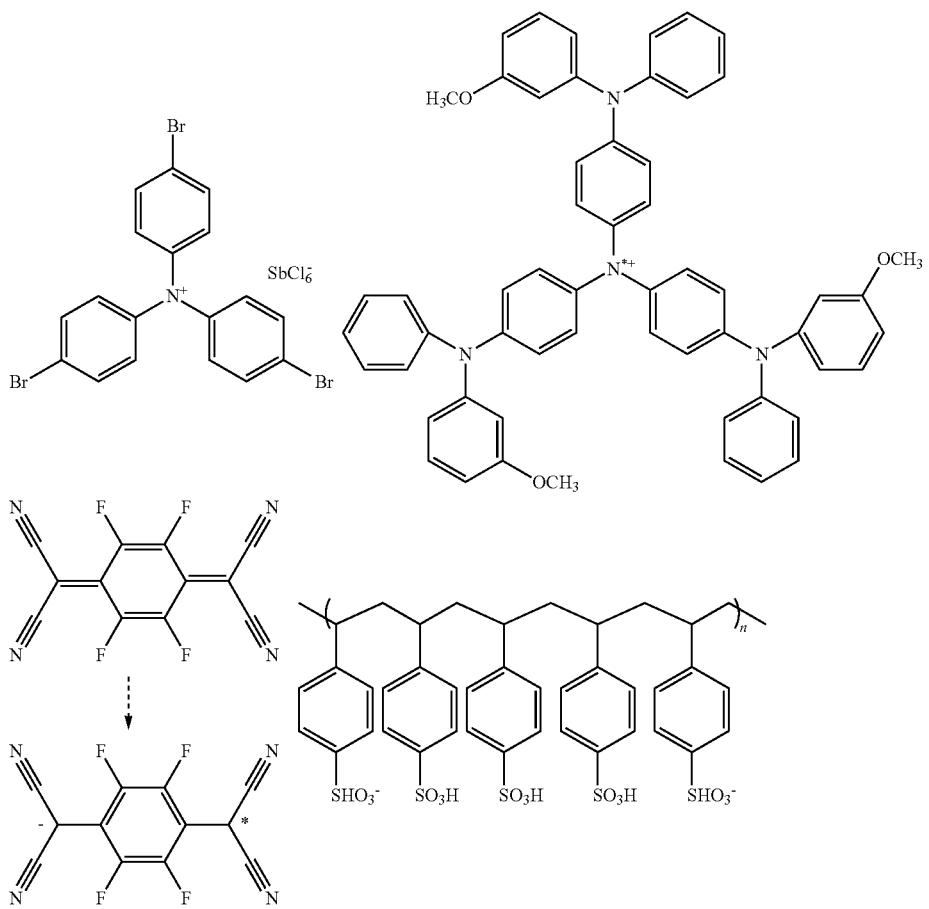
Preferred examples of a compound that may be used as the hole transporting material are shown below.
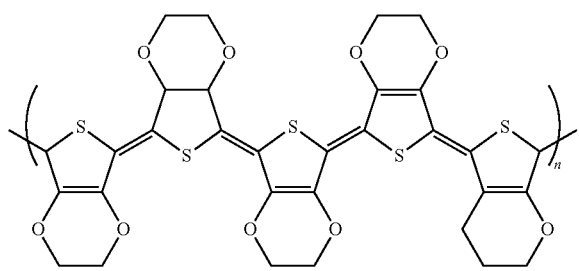

95
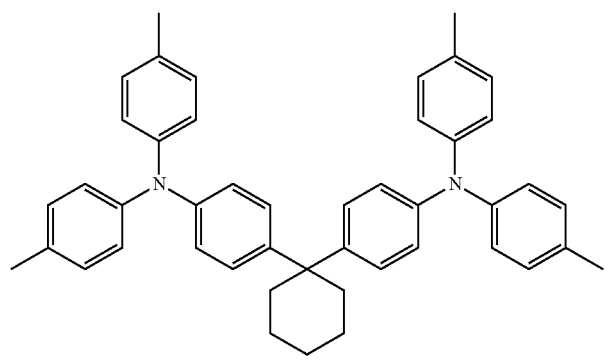
96
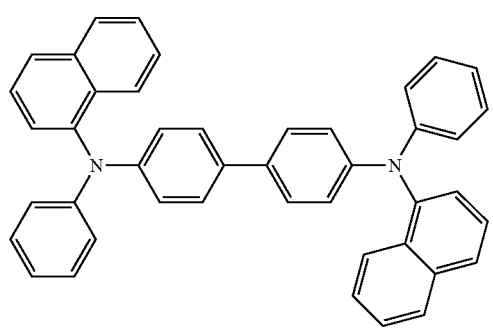
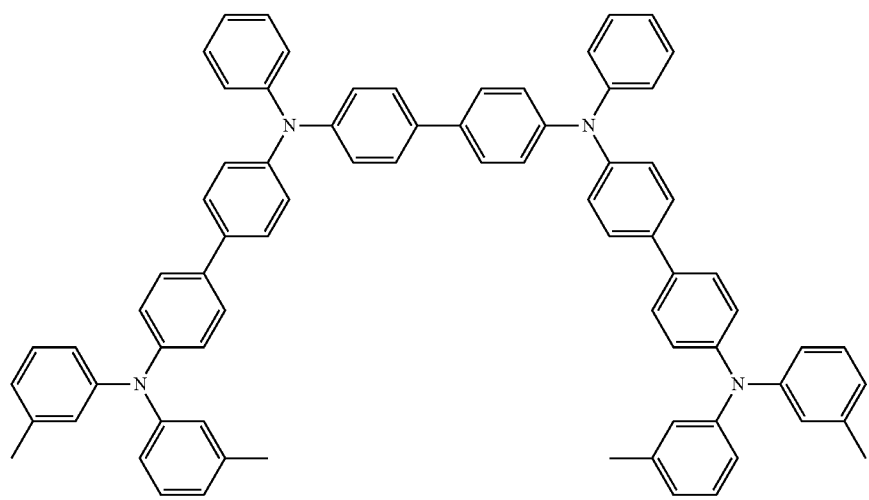
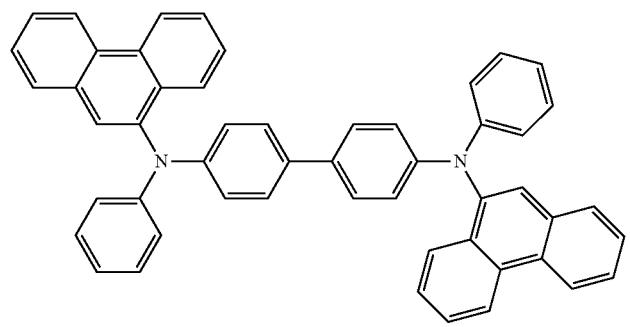
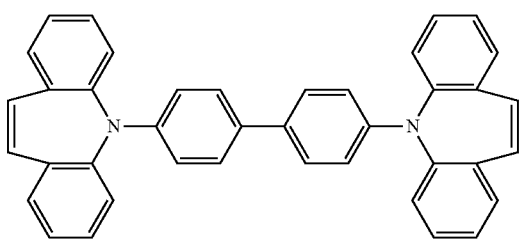

97
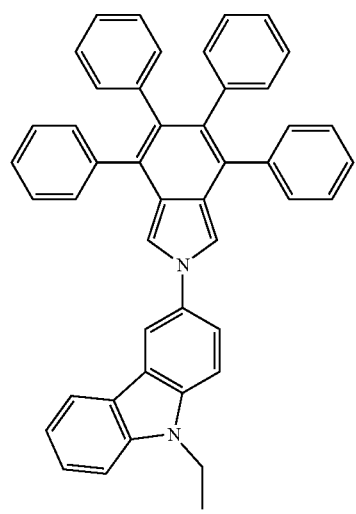
98
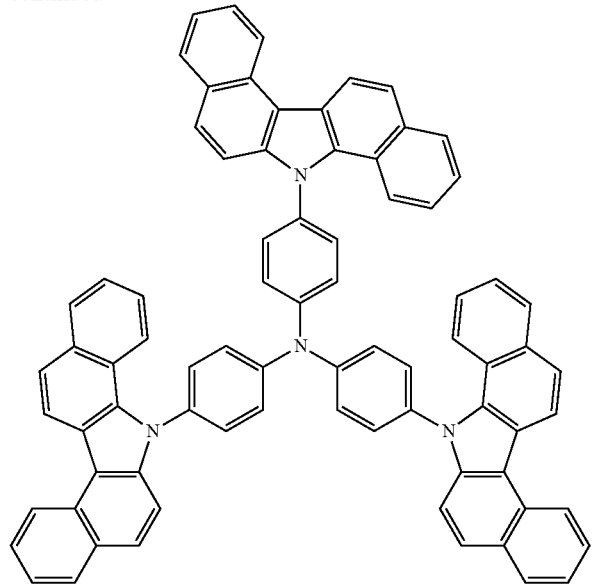
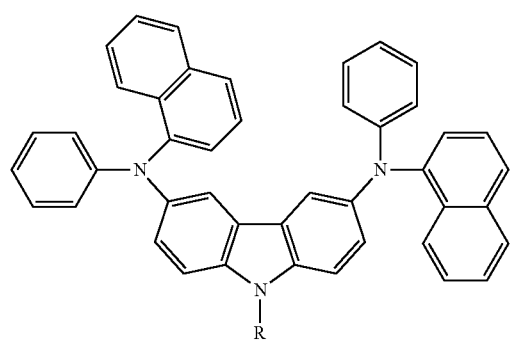
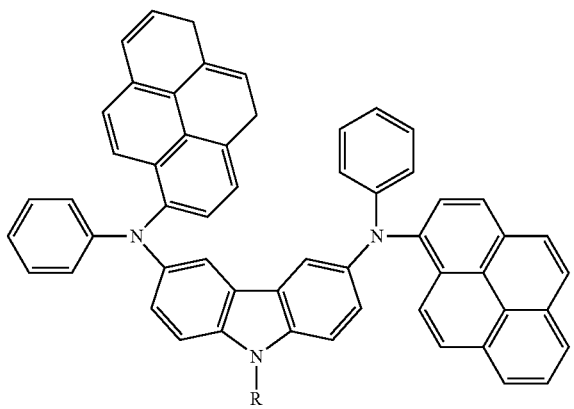
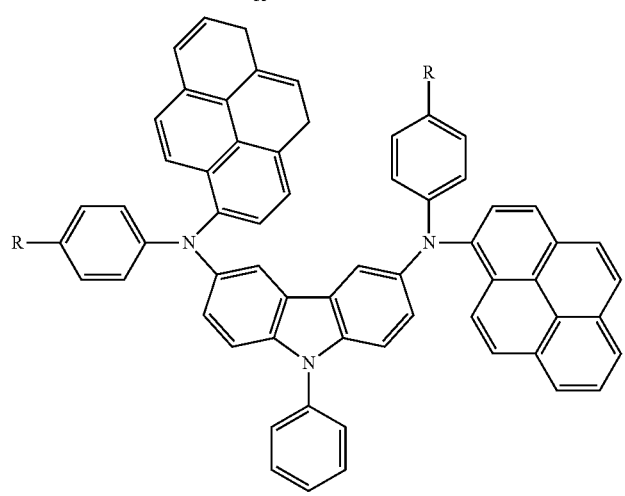

-continued
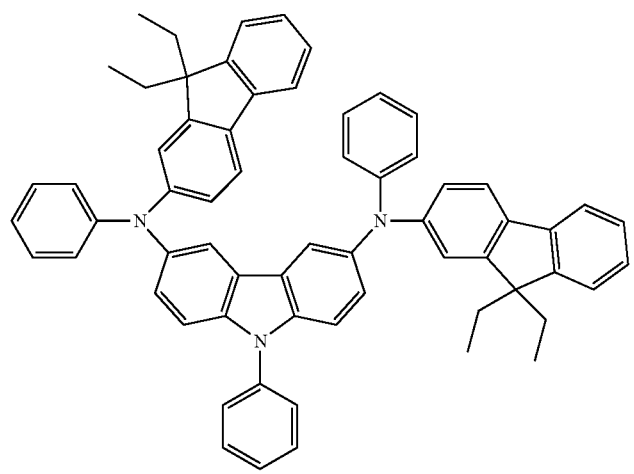
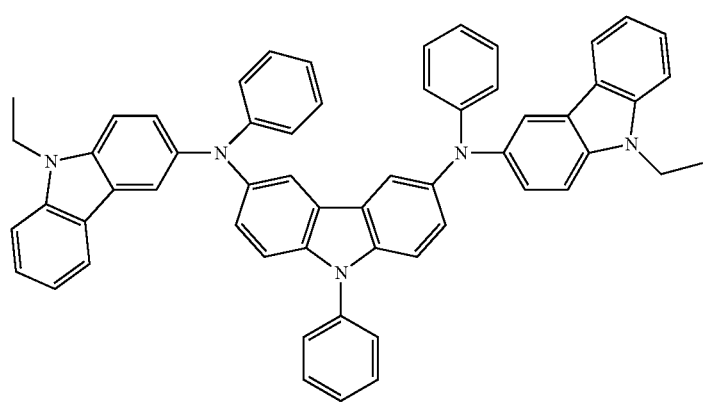
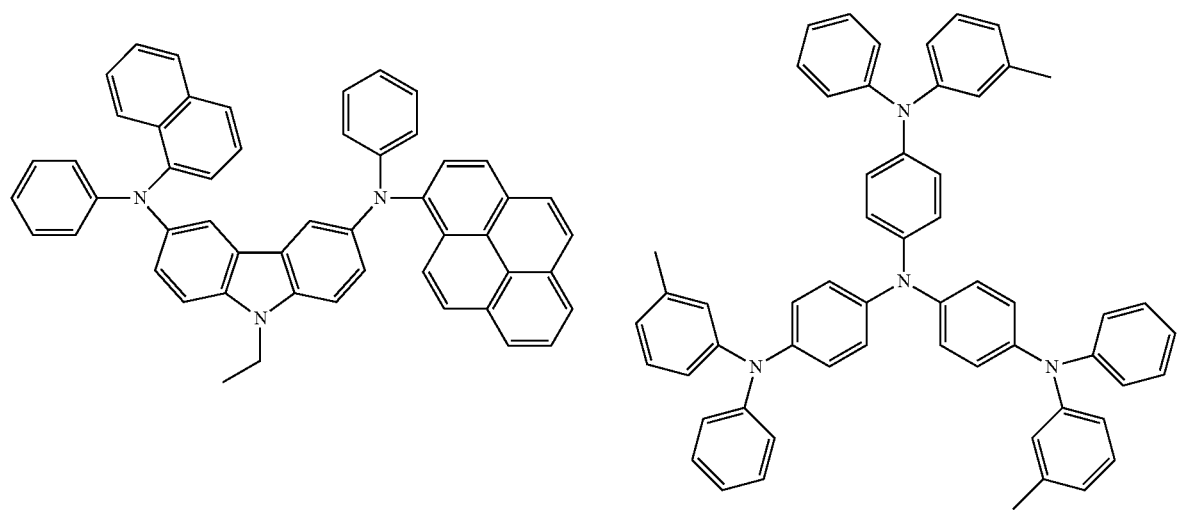

-continued
101
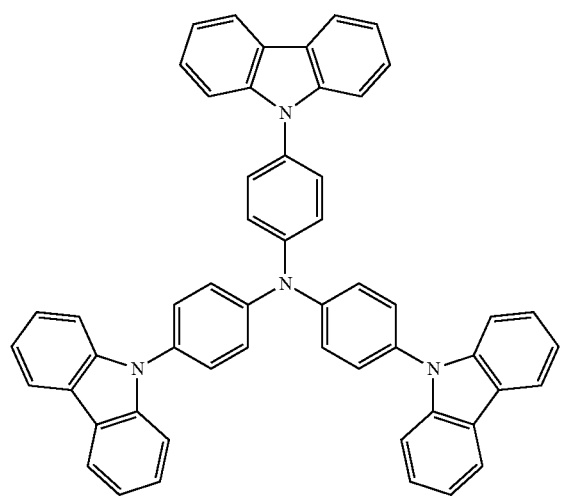
102
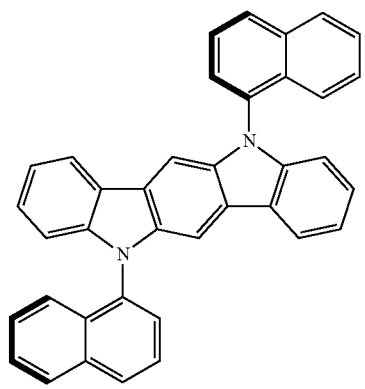
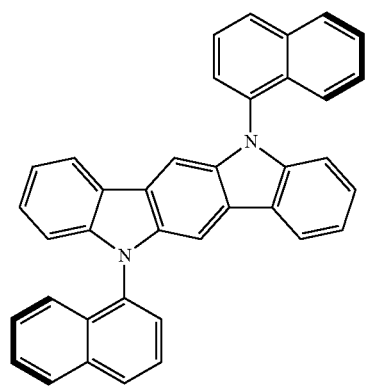
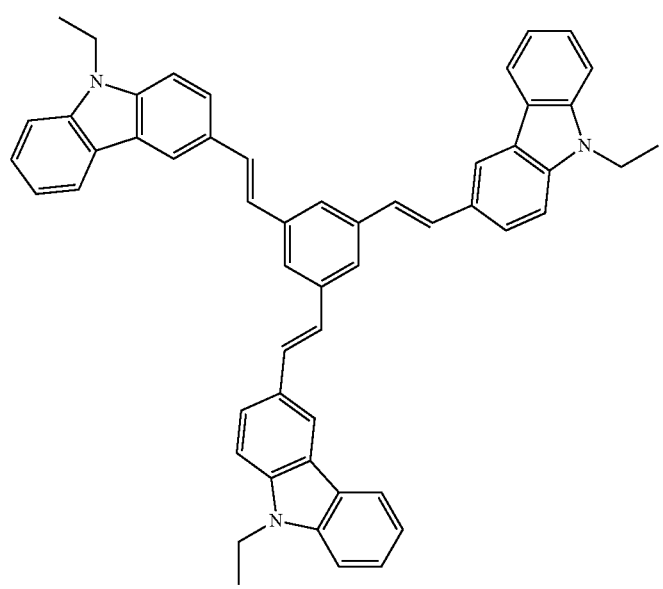

-continued
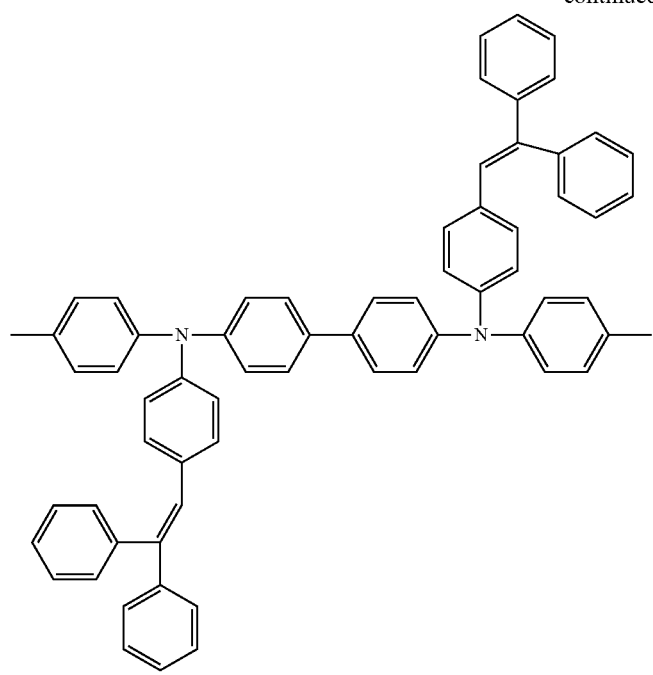
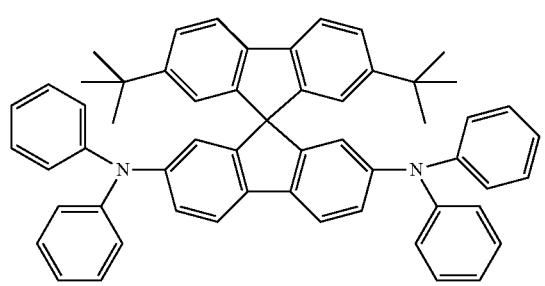
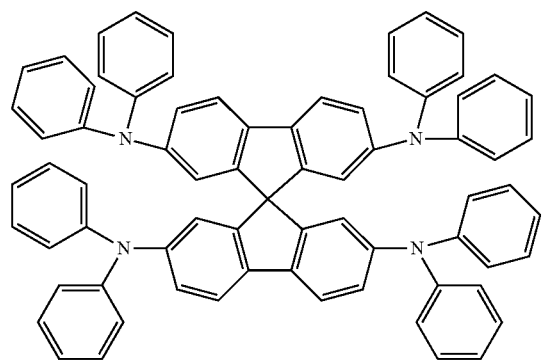
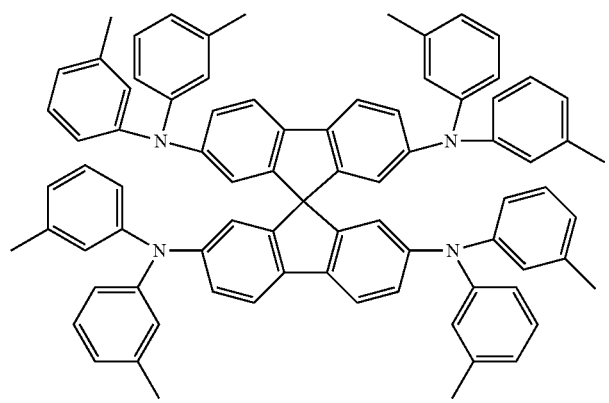
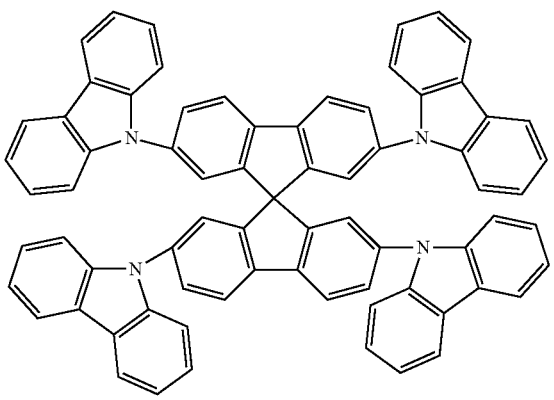
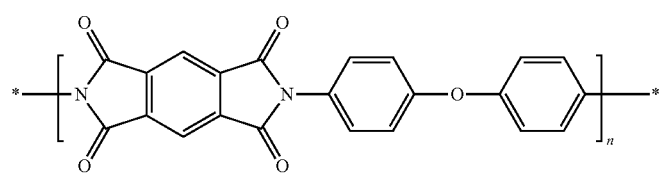

-continued
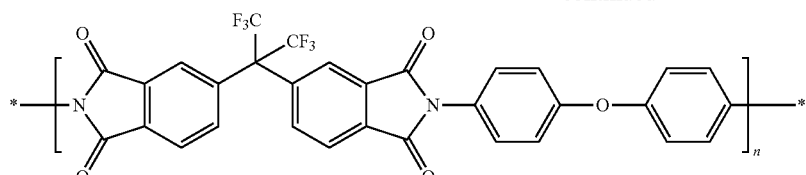
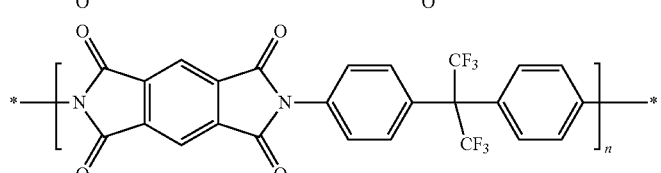
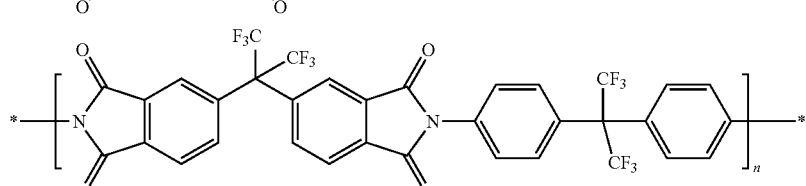
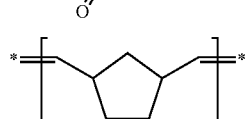
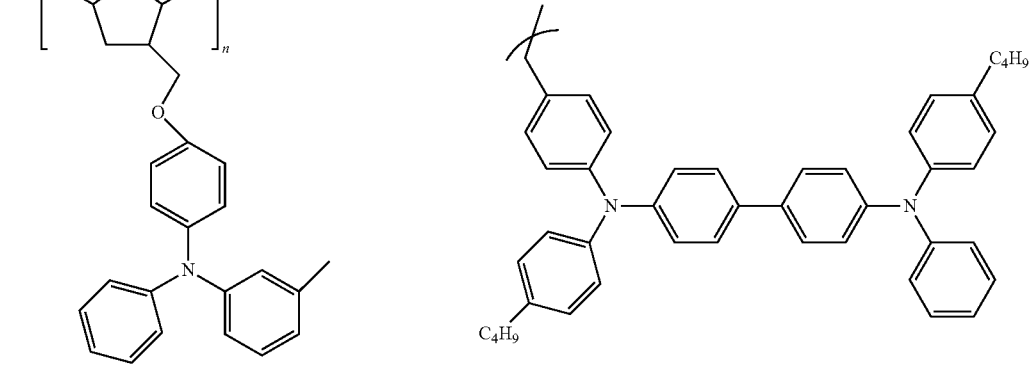
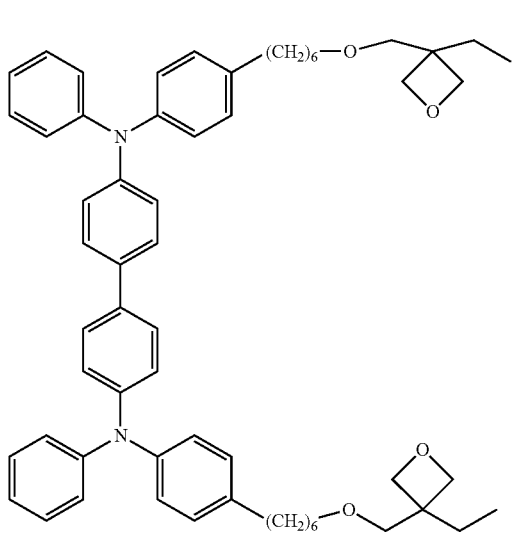
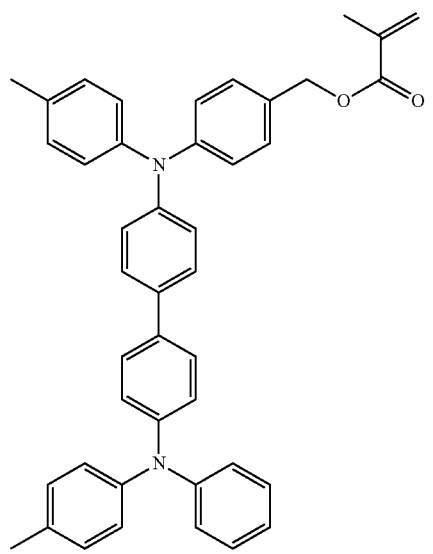

107
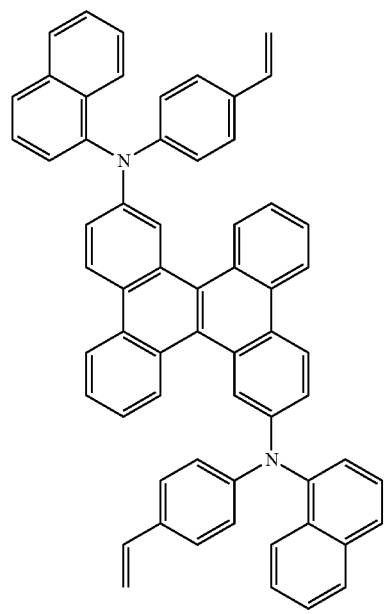
108
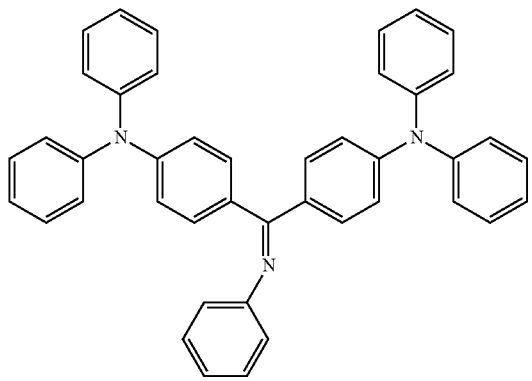
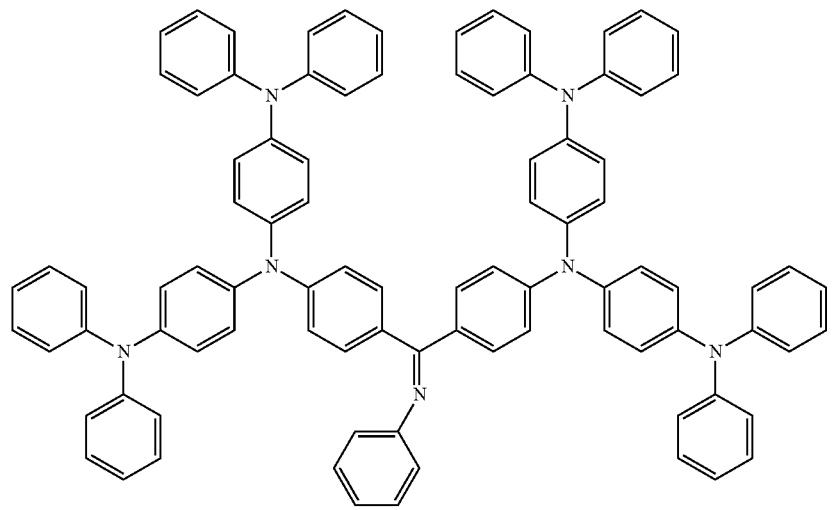

-continued
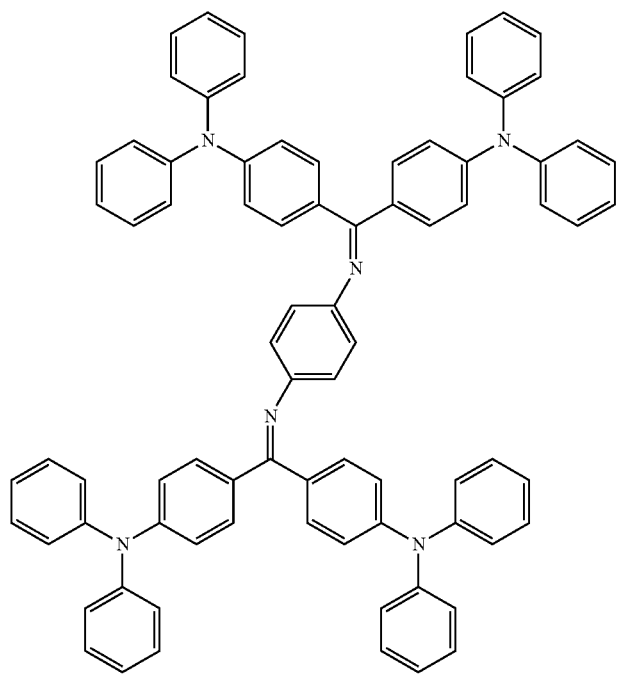
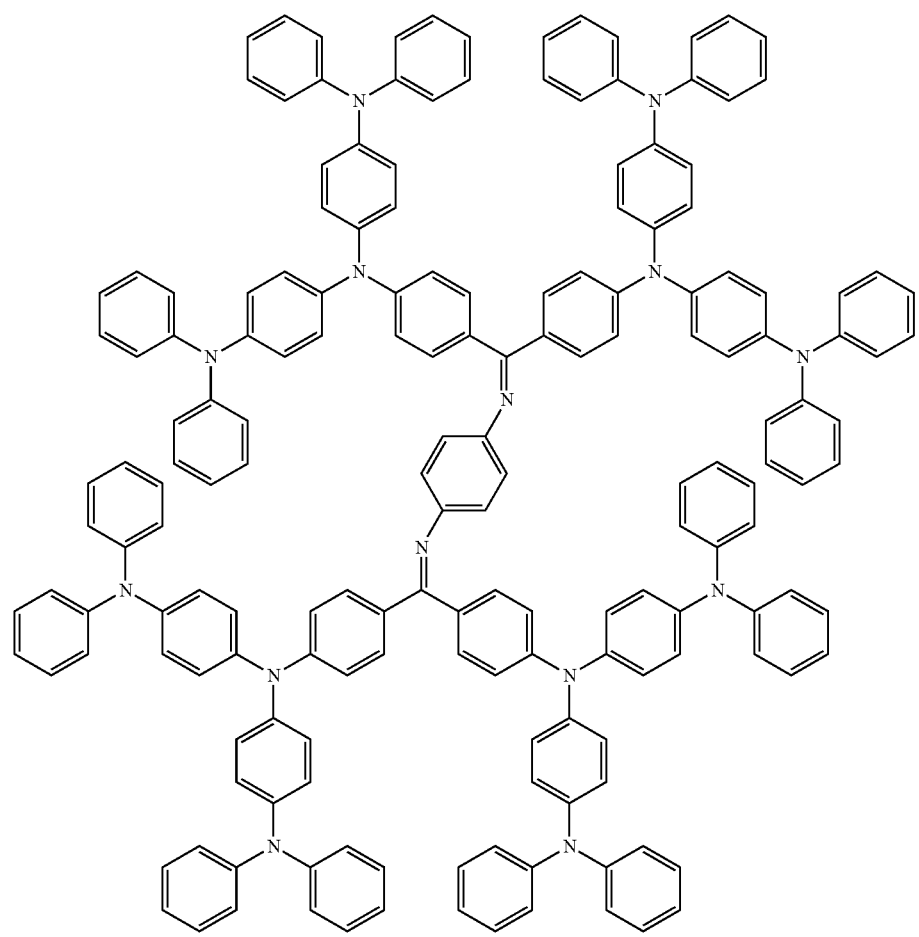

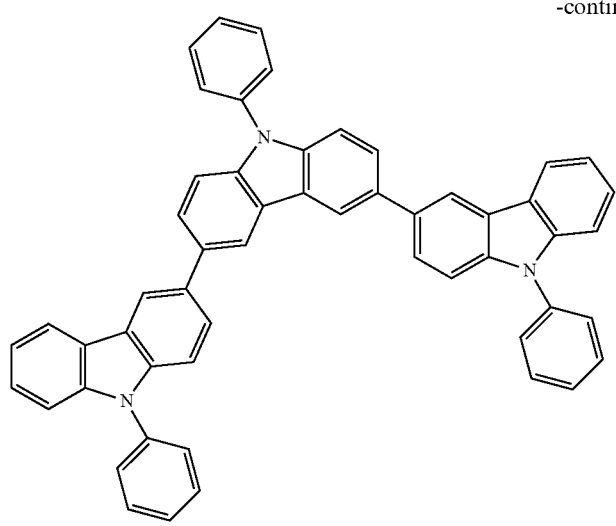
Preferred examples of a compound that may be used as the electron barrier material are shown below.
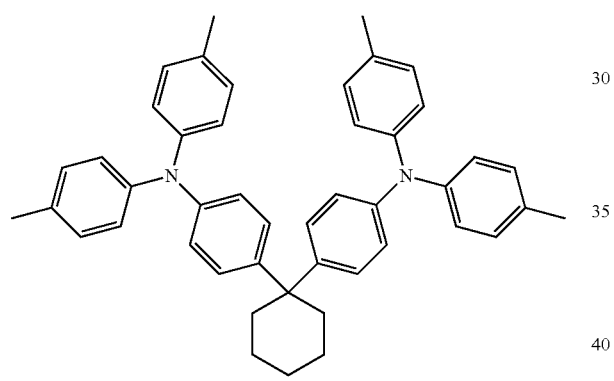
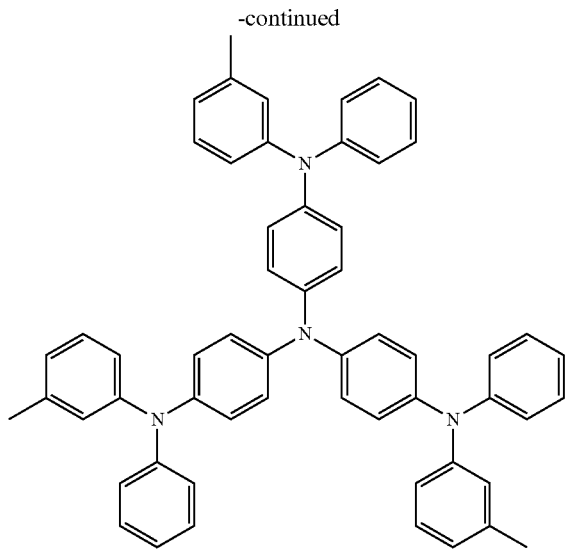
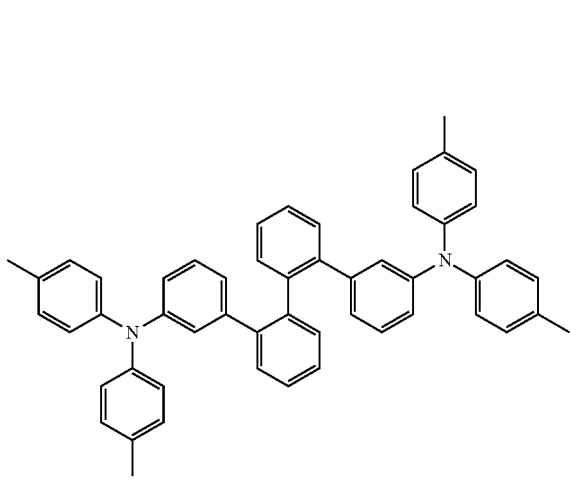
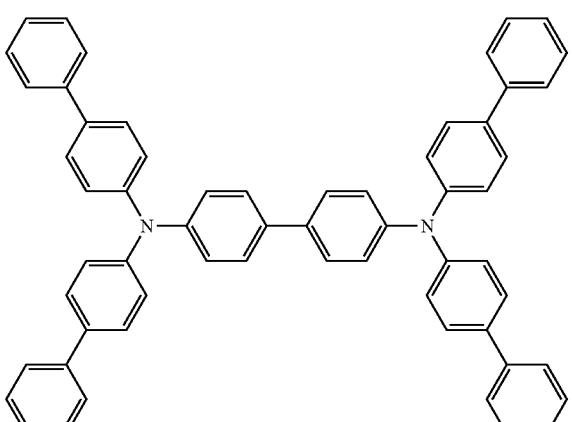
Preferred examples of a compound that may be used as the hole barrier material are shown below.

113
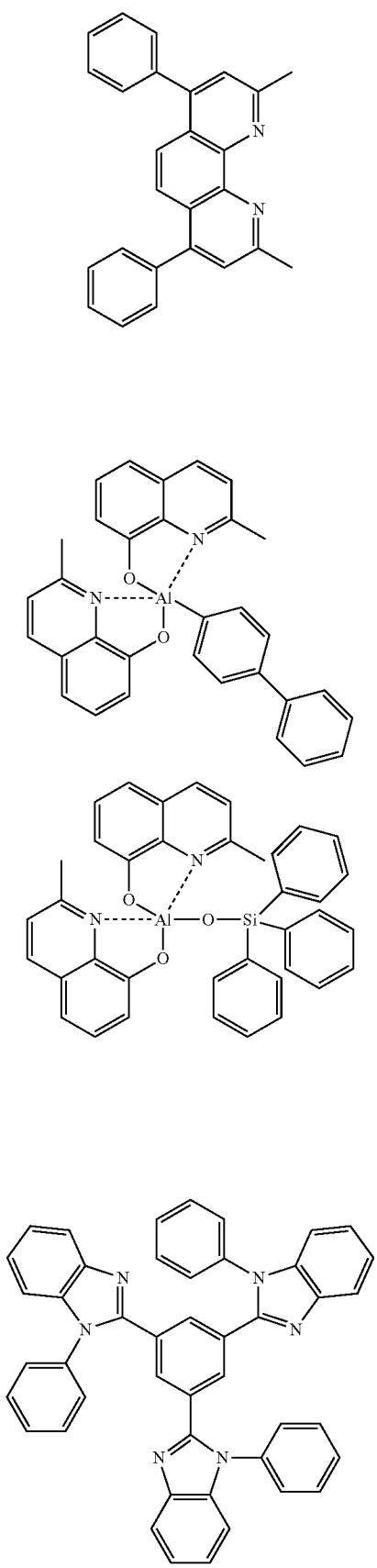
114
-continued
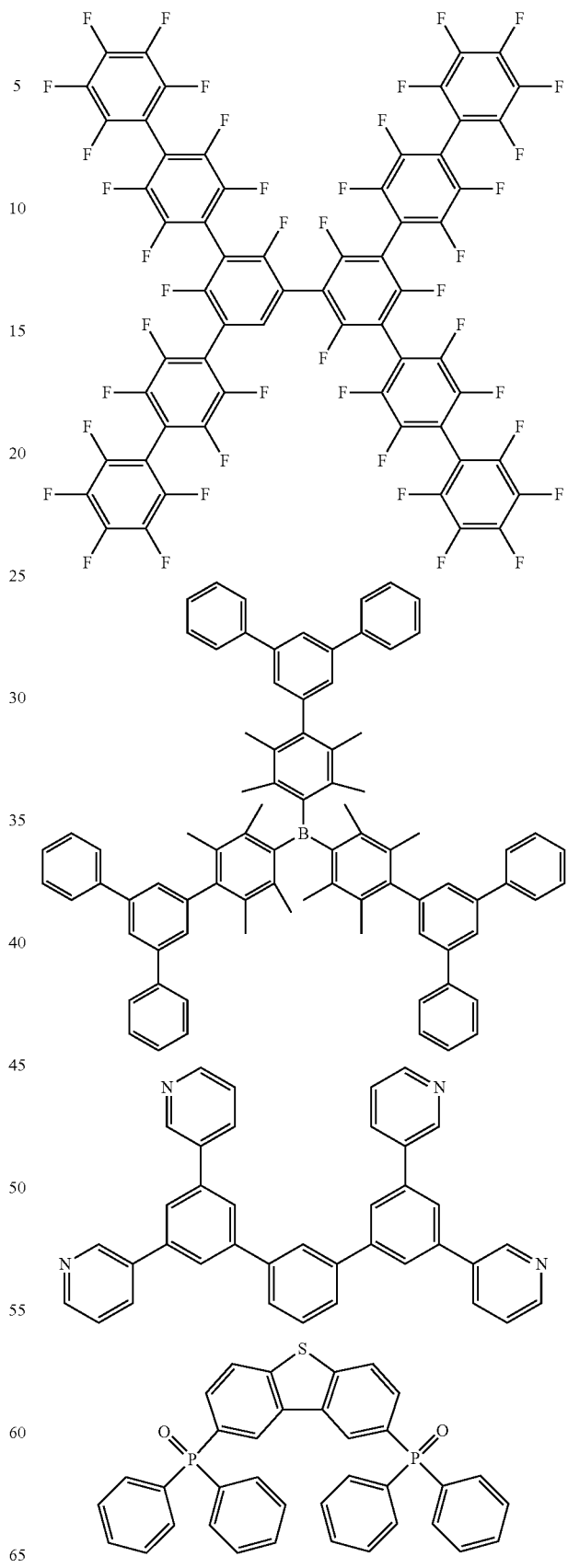

115
-continued
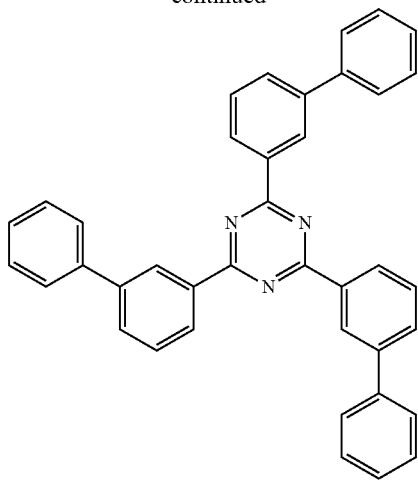
116
-continued
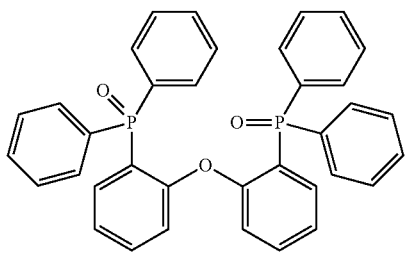
Preferred examples of a compound that may be used as the electron transporting material are shown below.
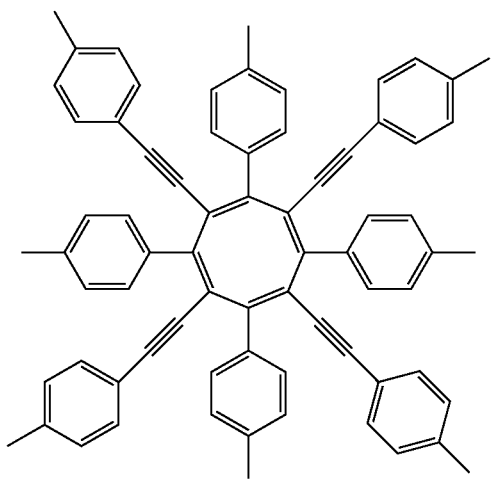
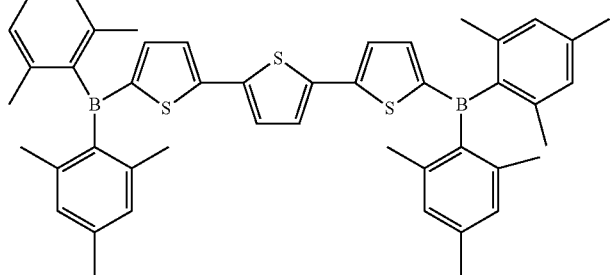
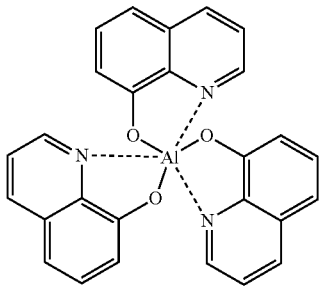
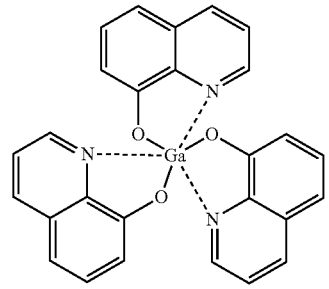
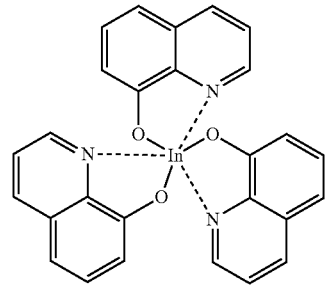
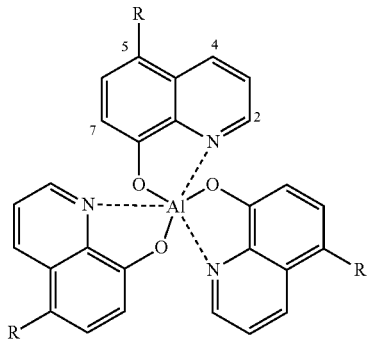
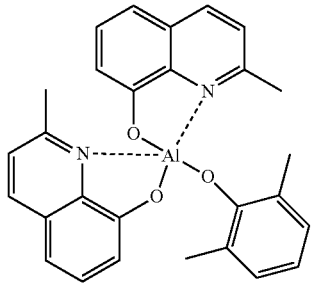
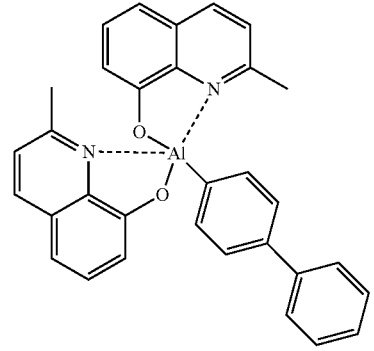

-continued
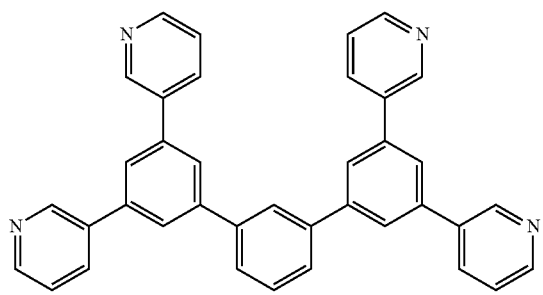
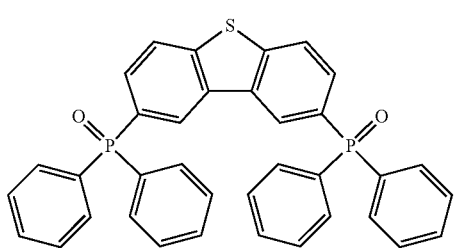
R = :
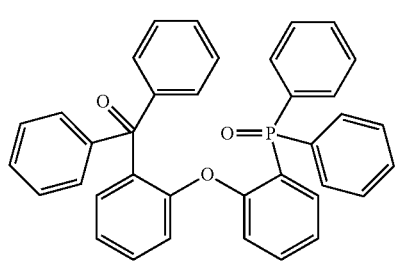
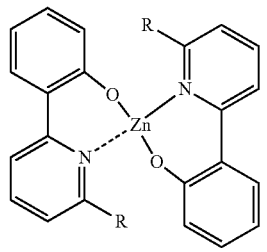
R=H
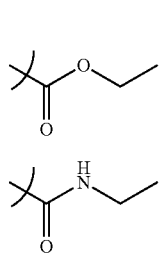
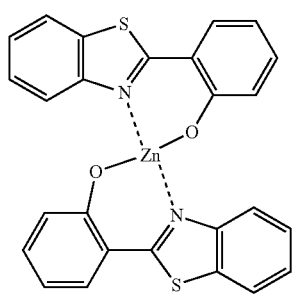
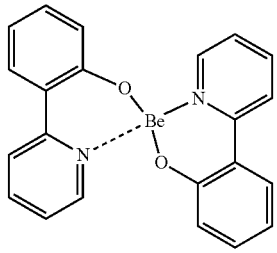
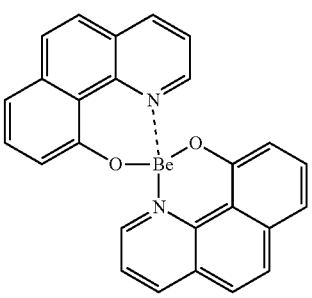
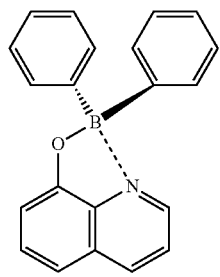
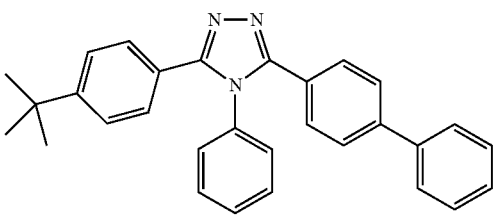
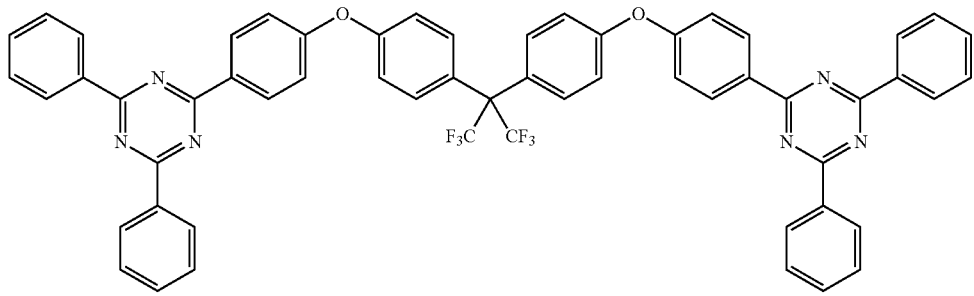

-continued
119
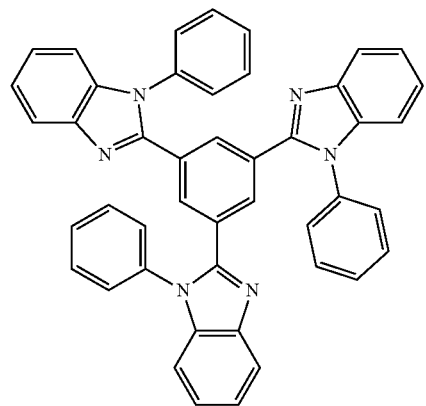
120
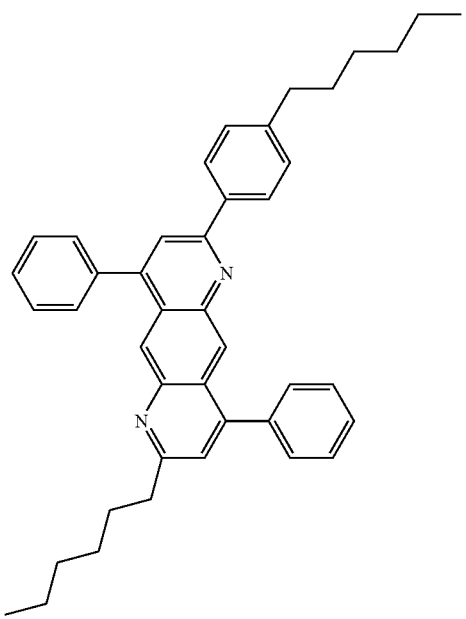
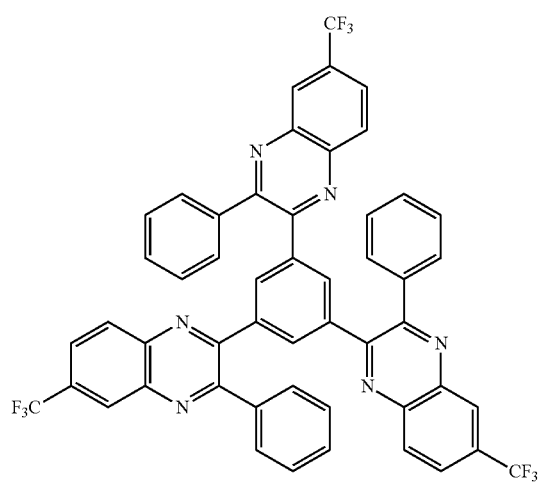
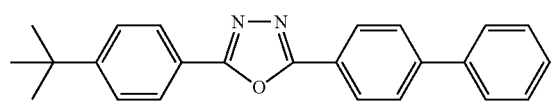

-continued
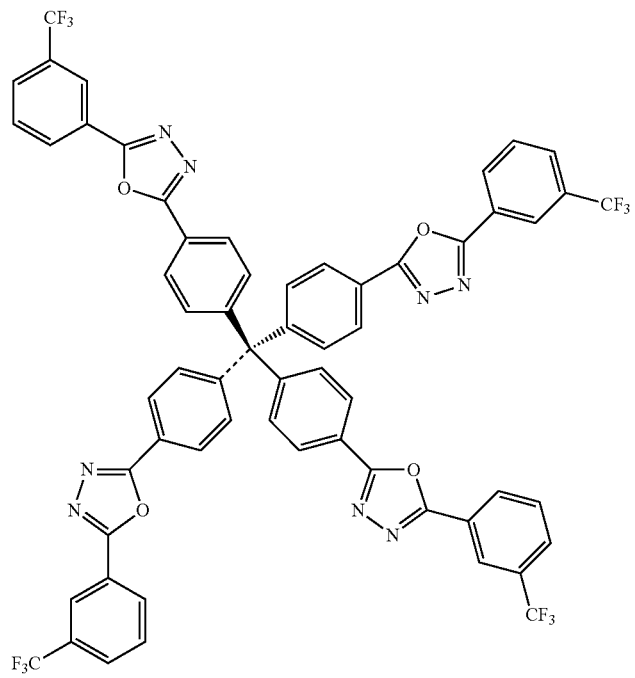
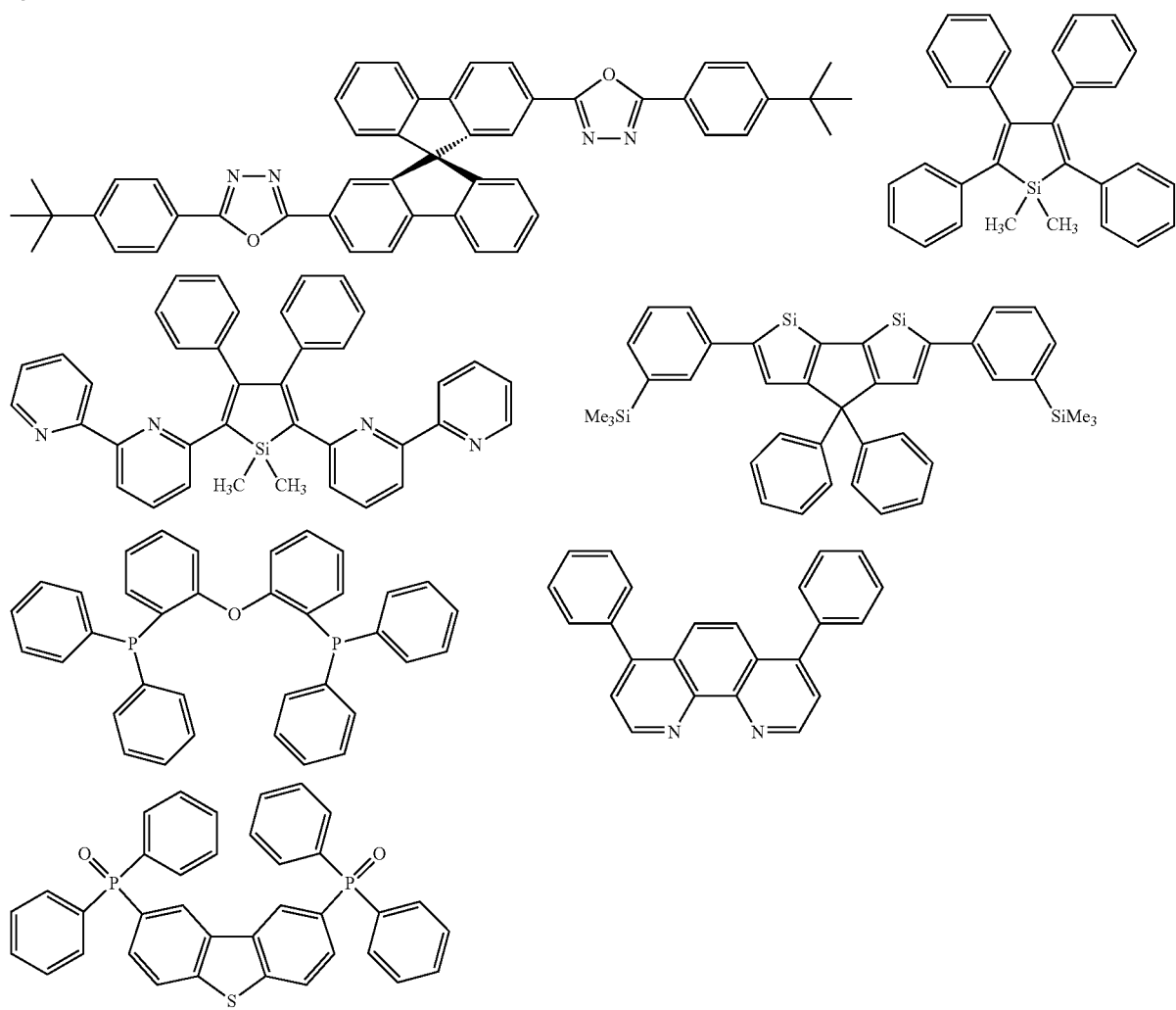

Preferred examples of a compound that may be used as the electron injection material are shown below.

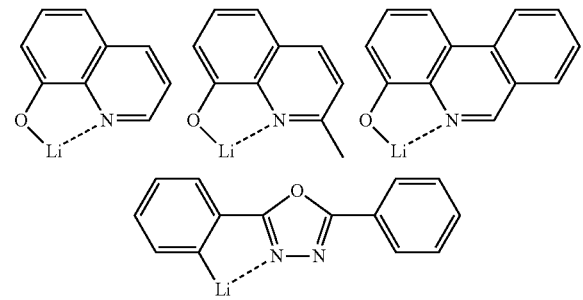

Preferred examples of a compound as a material that may be added are shown below. For example, the compound may be added as a stabilizing material.

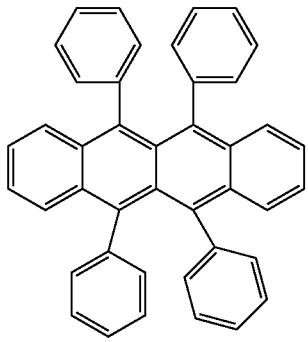

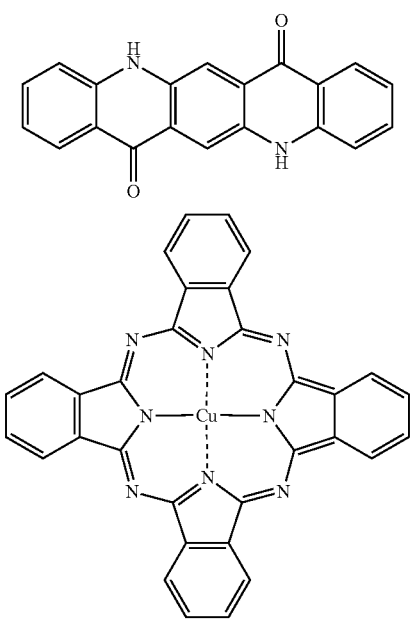

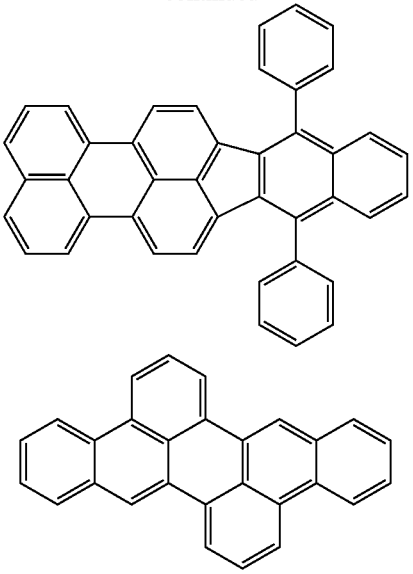

The organic electroluminescence device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescence device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescence device, of the invention may be applied to a further wide range of purposes. For example, an organic electroluminescent display apparatus may be produced with the organic electroluminescence device of the invention, and for the details thereof, reference may be made to S. Tokito, C. Adachi and H. Murata, "Yuki EL Display" (Organic EL Display) (Ohmsha, Ltd.). In particular, the organic electroluminescence device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

Synthesis Example 1

Synthesis of Compound 1

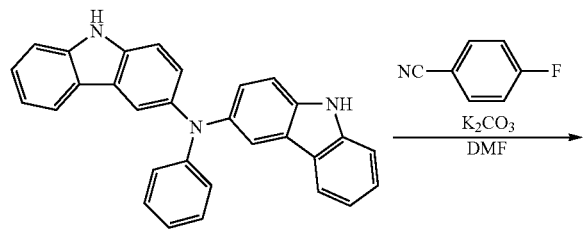

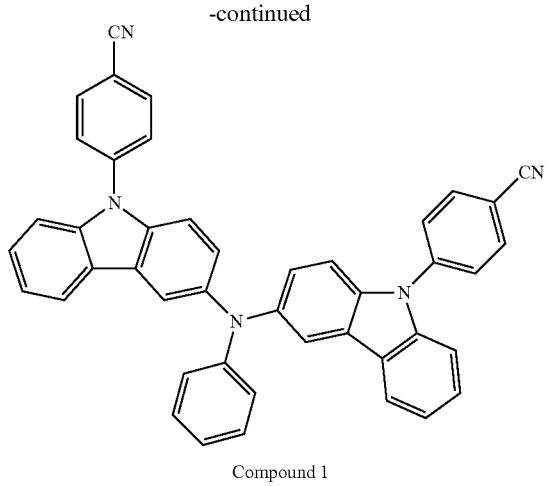

Compound 1

N,N-Bis(9H-carbazol-3-yl)aniline (0.68 g, 1.6 mmol) and potassium carbonate (0.96 g, 7.2 mmol) were placed in a 100 mL two-necked flask, which was then replaced with nitrogen. Thereafter, 4-fluorobenzonitrile (0.58 g, 4.8 mmol) and dimethylformamide (20 mL) were added thereto, and the mixture was agitated under heating to 100° C. for 24 hours. After naturally cooling to room temperature, water was added thereto, followed by agitating for 10 minutes, and a solid thus deposited was filtered. The solid was dissolved in dichloromethane, and hot filtered. The filtrate was reprecipitated from n-hexane, thereby providing 0.688 g (1.1 mmol, yield: 69%) of the compound 1 as white powder.

$^1$H NMR (500 MHz, CDCl$_3$): δ=7.97 (d, J=7.8 Hz, 2H; ArH), 7.93 (d, J=8.0 Hz, 2H; ArH), 7.90 (d, J=8.7 Hz, 4H; ArH), 7.76 (d, J=8.7 Hz, 4H; ArH), 7.46-7.38 (m, 6H; ArH), 7.31-7.21 (m, 6H; ArH), 7.10 (dd, J$_{ortho}$=8.7 Hz, J$_{meta}$=1.1 Hz, 2H; ArH), 6.95 (t, J=7.4 Hz, 1H; ArH)

Synthesis Example 2

Synthesis of Compound 2

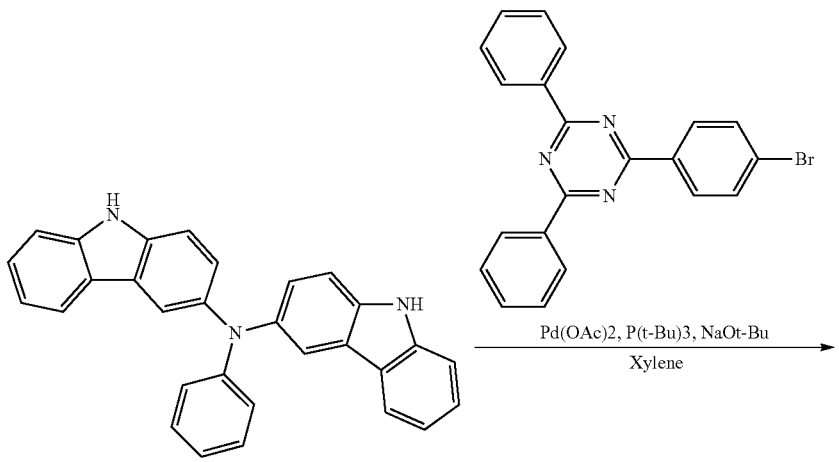

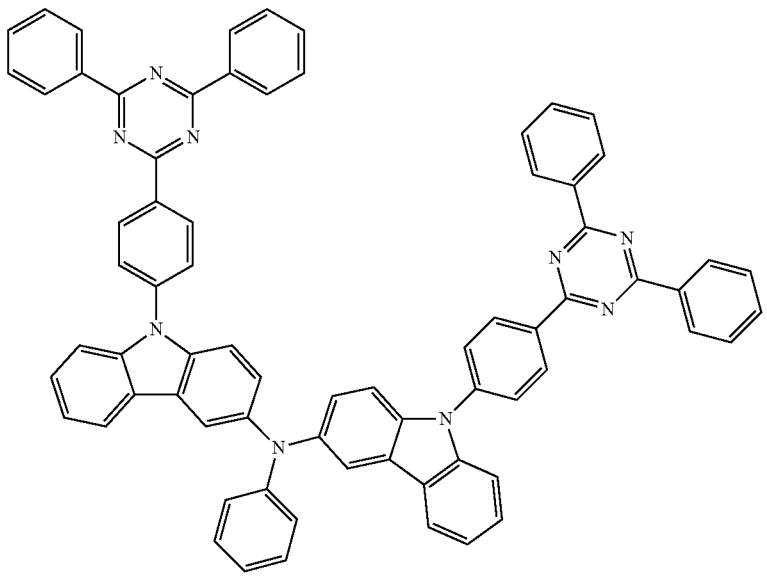

Compound 2

Sodium tert-butoxide (0.29 g, 3.0 mmol) was placed in a 100 mL three-necked flask, and dried in vacuum. Thereafter, after replacing with nitrogen, N,N-bis(9H-carbazol-3-yl)aniline (0.21 g, 0.50 mmol), 2-(4-bromophenyl)-4,6-diphenyl-1,3,5-triazine (0.427 g, 1.1 mmol), palladium(II) acetate (13 mg, 0.060 mmol), tri-tert-butylphosphine (0.03 mL, 0.060 mmol), and 20 mL of xylene were added thereto, and the mixture was agitated under heating to 110° C. for 72 hours. After naturally cooling to room temperature, a solid was obtained by filtration. The solid was rinsed with toluene, water, and methanol, and dried in vacuum, thereby providing 0.14 g (0.14 mmol, yield: 27%) of the compound 2 as yellow powder.

$^1$H NMR (500 MHz, Acetone $d_6$): d=9.14 (d, J=8.5 Hz, 4H; ArH), 8.88 (d, J=7.1 Hz, 8H; ArH), 8.13 (d, J=7.9 Hz, 2H; ArH), 8.12 (s, J=2.0 Hz, 2H; ArH), 7.99 (d, J=8.6 Hz, 4H; ArH), 7.74-7.63 (m, 16H; ArH), 7.49 (t, J=7.3 Hz, 2H; ArH), 7.39 (dd, $J_{ortho}$=8.8 Hz, $J_{meta}$=2.1 Hz 2H; ArH), 7.30-7.24 (m, 4H; ArH), 7.09 (d, J=7.8 Hz, 2H; ArH), 6.93 (t, J=7.3 Hz, 1H; ArH)

Synthesis Example 3

Synthesis of Compound 3

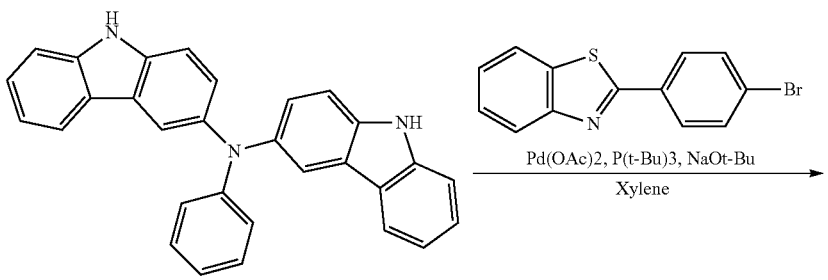

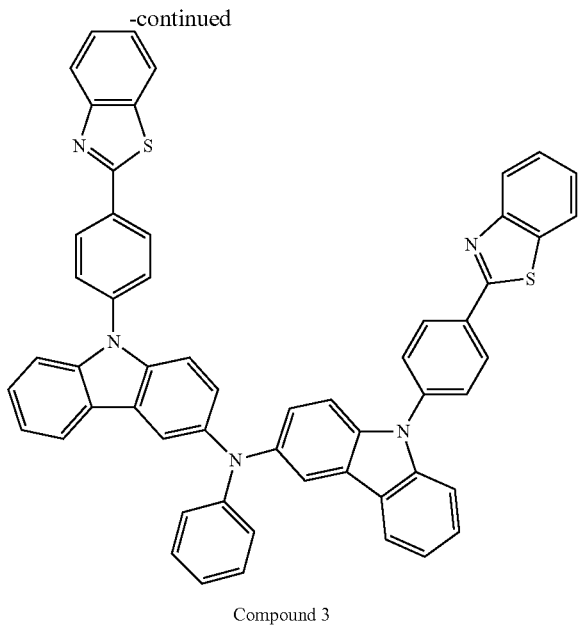

Compound 3

Sodium tert-butoxide (1.2 g, 12 mmol) was placed in a 300 mL three-necked flask, and dried in vacuum. Thereafter, after replacing with nitrogen, N,N-bis(9H-carbazol-3-yl)aniline (0.85 g, 2.0=01), 2-(4-bromophenyl)-benzothiazole (1.3 g, 4.4 mmol), palladium(II) acetate (54 mg, 0.24 mmol), tri-tert-butylphosphine (0.12 mL, 0.24 mmol), and xylene (20 mL) were added thereto, and the mixture was agitated under heating to 100° C. for 22 hours. After naturally cooling to room temperature, the reaction solution was concentrated with an evaporator, and separated with dichloromethane and water. The organic layer was dried over magnesium sulfate, and concentrated with an evaporator. The concentrated solution was purified by column chromatography (stationary phase: silica gel, developing solvent: toluene), and the resulting target compound was purified by sublimation purification, thereby providing 0.90 g (1.07 mmol, yield: 54%) of the compound 3 as a yellow glassy solid.

$^1$H NMR (500 MHz, CDCl$_3$): d=8.34 (d, J=8.5 Hz, 4H; ArH), 8.11 (d, J=8.0 Hz, 2H; ArH), 8.01-7.95 (m, 6H; ArH), 7.76 (d, J=8.5 Hz, 4H; ArH), 7.55-7.50 (m, 4H; ArH), 7.44-7.40 (m, 6H; ArH), 7.33 (d, J$_{ortho}$=9.9 Hz, J$_{meta}$=1.4 Hz, 2H; ArH), 7.25-7.22 (m, 4H; ArH), 7.11 (d, J=8.6 Hz, 2H; ArH), 6.92 (t, J=6.9, 1H; ArH)

Example 1

Production and Evaluation of Organic Photoluminescent Device Using Compound 1

A toluene solution of the compound 1 (concentration: 1×10$^{-5}$ mol/L) was prepared in a glove box under an Ar atmosphere.

A thin film of the compound 1 was formed to a thickness of 50 nm on a quartz substrate by a vacuum vapor deposition method under a condition of a vacuum degree of 5×10$^{-4}$ Pa or less, thereby providing an organic photoluminescent device.

Separately from the above, the compound 1 and DPEPO were vapor-deposited from separate vapor deposition sources on a quartz substrate under a condition of a vacuum degree of 5×10$^{-4}$ Pa or less, so as to form a thin film having a thickness of 100 nm and a concentration of the compound 1 of 6% by weight, thereby providing an organic photoluminescent device.

Figure 2:
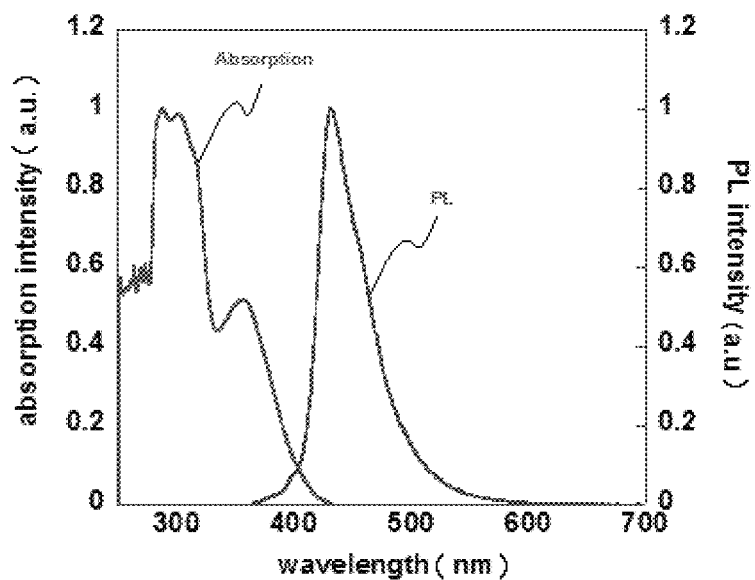
FIG. 2 shows the light emission and absorption spectra of the toluene solution of the compound 1 in Example 1.
Figure 3:
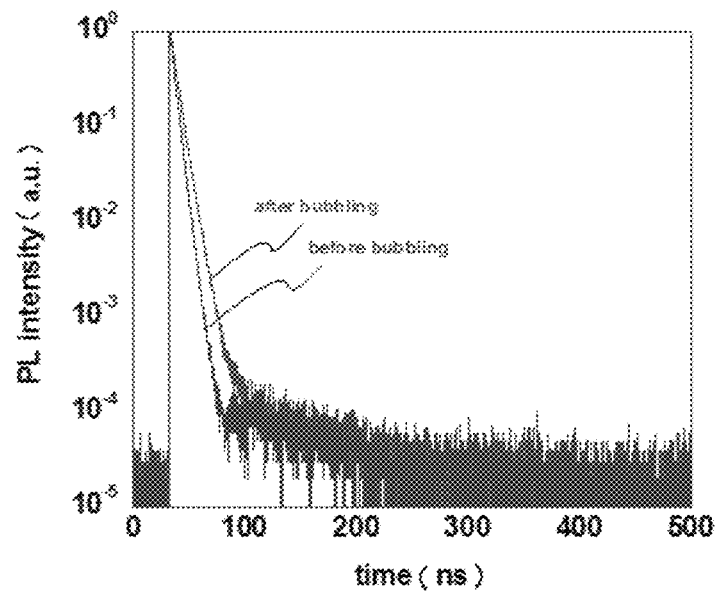
FIG. 3 shows the transient decay curves of the toluene solution of the compound 1 in Example 1.

The toluene solution of the compound 1 was measured for a light emission spectrum, a light absorption spectrum, and a transient decay curve, with excitation light of 300 nm and 355 nm. FIG. 2 shows the light emission and absorption spectra, and FIG. 3 shows the transient decay curves, with excitation light of 337 nm. The transient decay curve shows the measurement result of the light emission lifetime obtained by measuring the process where the light emission intensity is deactivated on irradiating the compound with excitation light. In ordinary one-component light emission (fluorescent light or phosphorescent light), the light emission intensity is decays monoexponentially. This means that the light emission intensity decays linearly on a graph with the semilogarithm as the ordinate. In a transient decay curve of the compound 1 shown in FIG. 3, while a linear component (fluorescent light) was observed in the initial stage of observation, a component that deviated from the linearity appeared after several microseconds. The later component is light emission of the delayed component, and the signal thereof added to the initial component appears as a long tail curve on the longer time side. Thus, the measurement of the light emission lifetime revealed that the compound 1 was a light-emitting material that contained a delayed component in addition to a fluorescent component. The photoluminescence quantum efficiency was 13.5% (excitation light of 355 nm) for the toluene solution without bubbling and 20.5% (excitation light of 355 nm) or 32.7% (excitation light of 300 nm) for the toluene solution with nitrogen bubbling. FIG. 3 confirmed delayed fluorescence.

Figure 4:
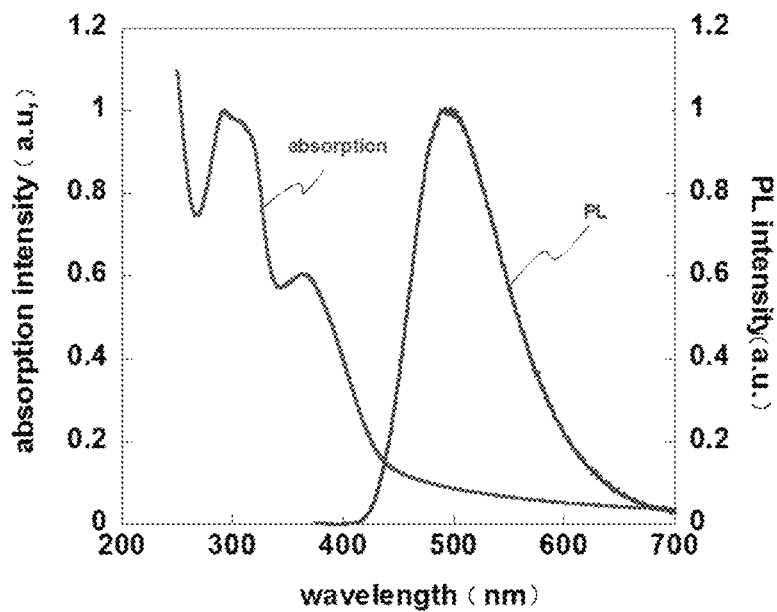
FIG. 4 shows the light emission and absorption spectra of the thin film organic photoluminescent device of the compound 1 in Example 1.
Figure 5:
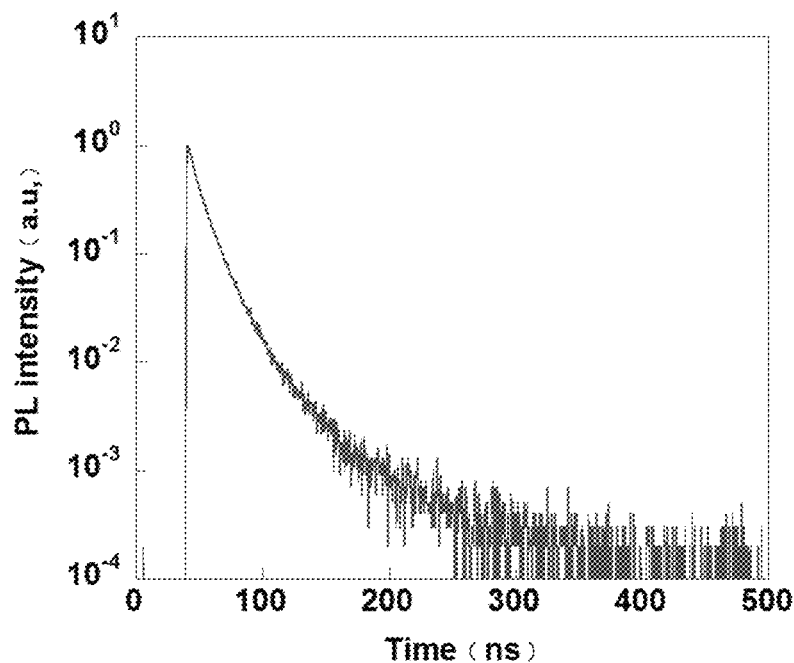
FIG. 5 shows the transient decay curve of the thin film organic photoluminescent device of the compound 1 in Example 1.
Figure 6:
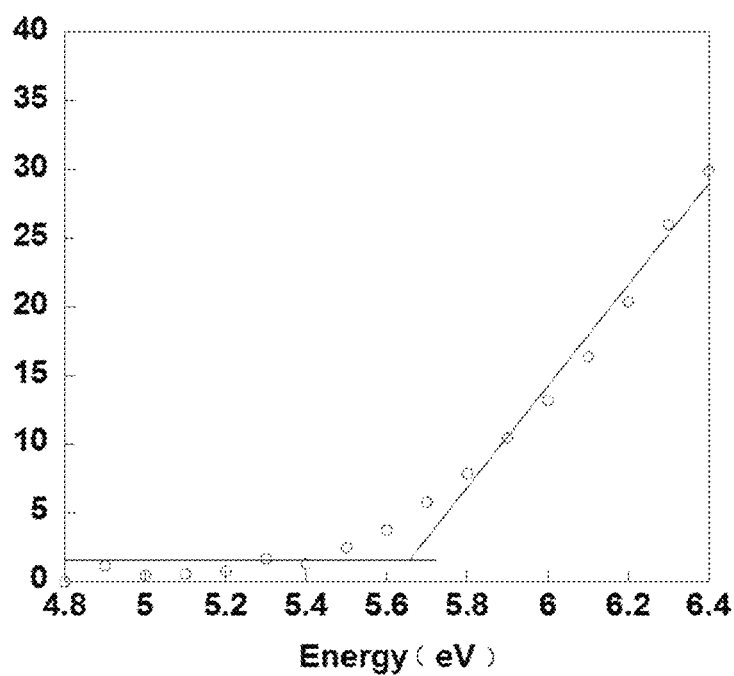
FIG. 6 shows the energy profile by a photoelectron analysis method of the thin film organic photoluminescent device of the compound 1 in Example 1.

FIG. 4 shows the result of the measurement of the light emission and absorption spectra of the organic photoluminescent device having the thin film containing only the compound 1 with excitation light of 365 nm, FIG. 5 shows the measurement result of the transient decay curve thereof, and FIG. 6 shows the energy profile by a photoelectron analysis method thereof. The photoluminescence quantum efficiency was 35.4%, and delayed fluorescence was confirmed from FIG. 5. It was further conformed from FIG. 6 that the energy level of HOMO was 5.63 eV, the energy level of LUMO was 2.85 eV, and the HOMO-LUMO gap was 2.78 eV, which revealed that HOMO and LUMO were appropriately separated.

Figure 7:
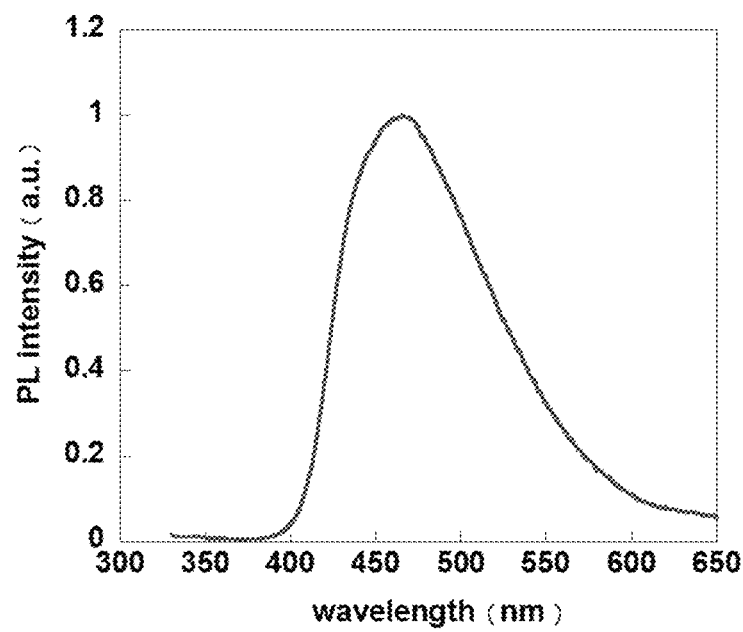
FIG. 7 shows the light emission spectrum of the thin film organic photoluminescent device of the compound 1 and DPEPO in Example 1.

The organic photoluminescent device having the thin film of the compound 1 and DPEPO was measured for light emission spectra with excitation light of 290 nm, 300 nm, and 310 nm. Among these, FIG. 7 shows the light emission spectrum with excitation light of 290 nm. The photoluminescence quantum efficiency was 52.3% for the excitation light of 290 nm, 44.2% for the excitation light of 300 nm, and 44.5% for the excitation light of 310 nm.

Figure 8:
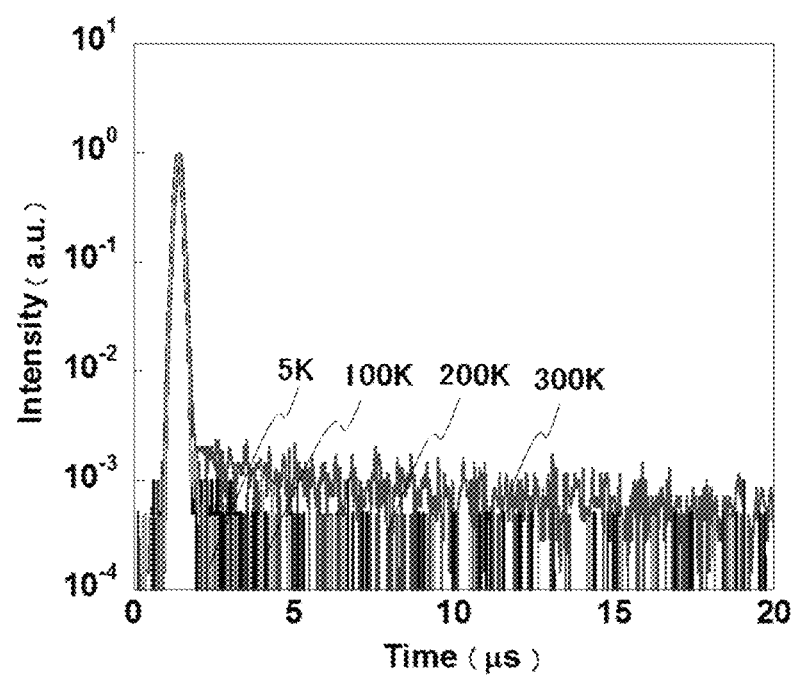
FIG. 8 shows the transient decay curves of the thin film organic photoluminescent device of the compound 1 and DPEPO in Example 1.
Figure 9:
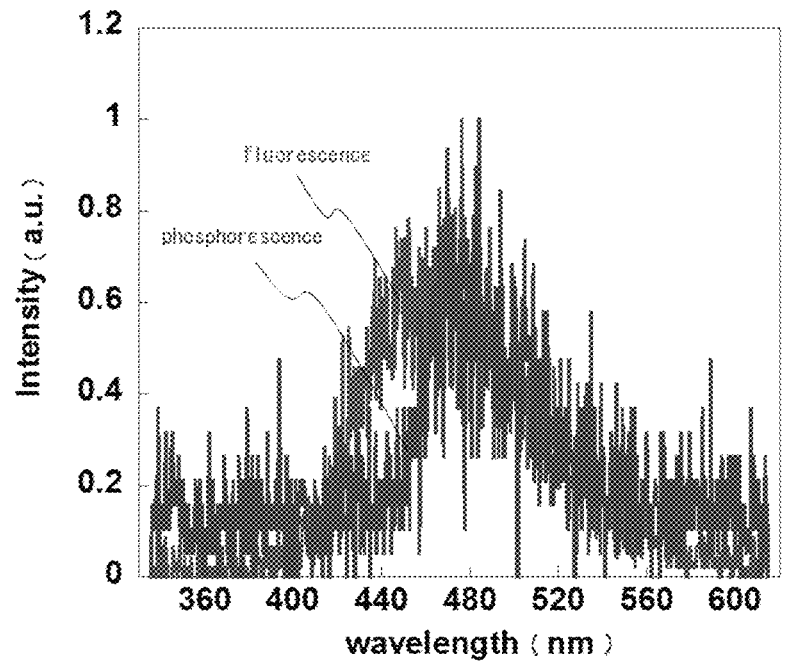
FIG. 9 shows the fluorescence spectrum and the phosphorescent spectrum of the thin film organic photoluminescent device of the compound 1 and DPEPO in Example 1.

FIG. 8 shows the measurement result of the transient decay curves of the organic photoluminescent device having the thin film of the compound 1 and DPEPO, and FIG. 9 shows the measurement result of the fluorescence spectrum and the phosphorescent spectrum thereof. FIG. 8 confirmed thermal activation type delayed fluorescence, in which the delayed fluorescent component was increased with the increase of the temperature. FIG. 9 revealed that the energy difference $\Delta E_{ST}$ between the singlet excited state and the triplet excited state was 0.21 eV.

Example 2

Production and Evaluation of Organic Photoluminescent Device Using Compound 2

A toluene solution of the compound 2 was prepared by changing the point that the compound 2 was used instead of the compound 1. An organic photoluminescent device having a thin film of the compound 2 and mCP and an organic photoluminescent device having a thin film of the compound 2 and CBP were produced by changing the point that the compound 2 was used instead of the compound 1, and mCP or CBP was used instead of DPEPO.

Figure 10:
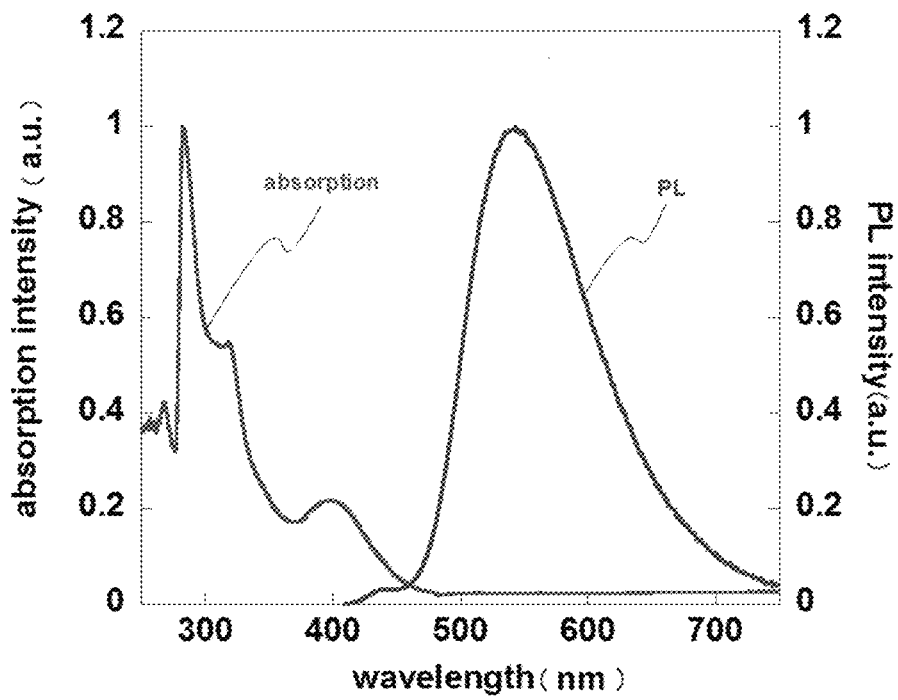
FIG. 10 shows the light emission and absorption spectra of the toluene solution of the compound 2 in Example 2.
Figure 11:
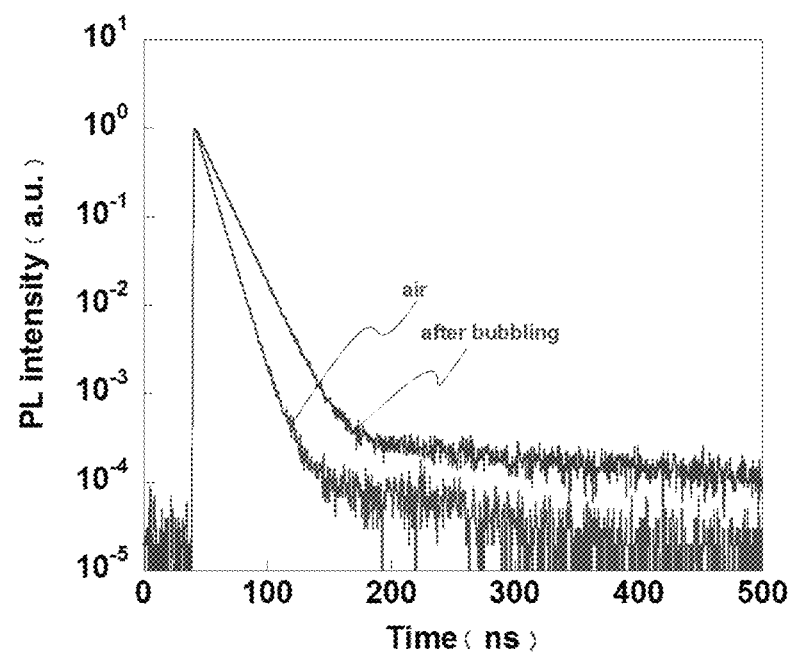
FIG. 11 shows the transient decay curves of the toluene solution of the compound 2 in Example 2.

FIG. 10 shows the measurement result of the light emission spectrum and the light absorption spectrum with excitation light of 399 nm of the toluene solution of the compound 2, and FIG. 11 shows the measurement result of the transient decay curves thereof. The photoluminescence quantum efficiency was 31.8% for the toluene solution without bubbling, and 49.5% for the toluene solution with nitrogen bubbling. FIG. 11 confirmed delayed fluorescence.

Figure 12:
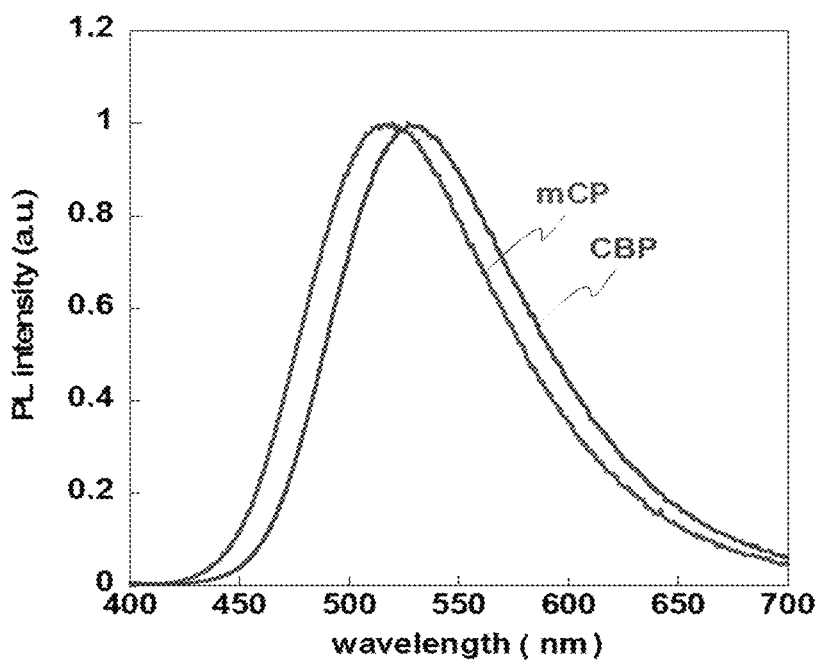
FIG. 12 shows the light emission spectra of the thin film organic photoluminescent device of the compound 2 and mCP and the film organic photoluminescent device of the compound 2 and CBP in Example 2.
Figure 13:
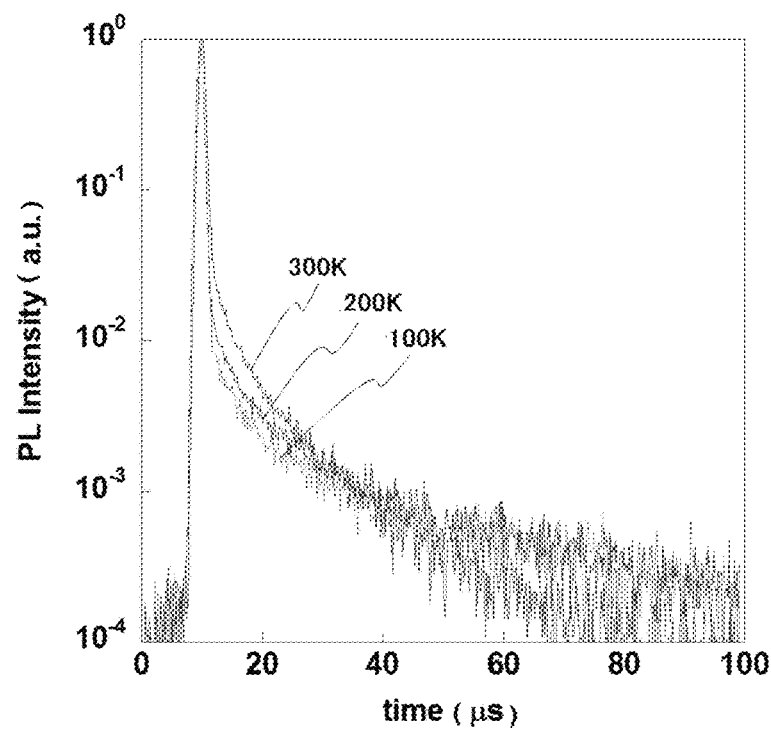
FIG. 13 shows the transient decay curves of the thin film organic photoluminescent device of the compound 2 and mCP in Example 2.
Figure 14:
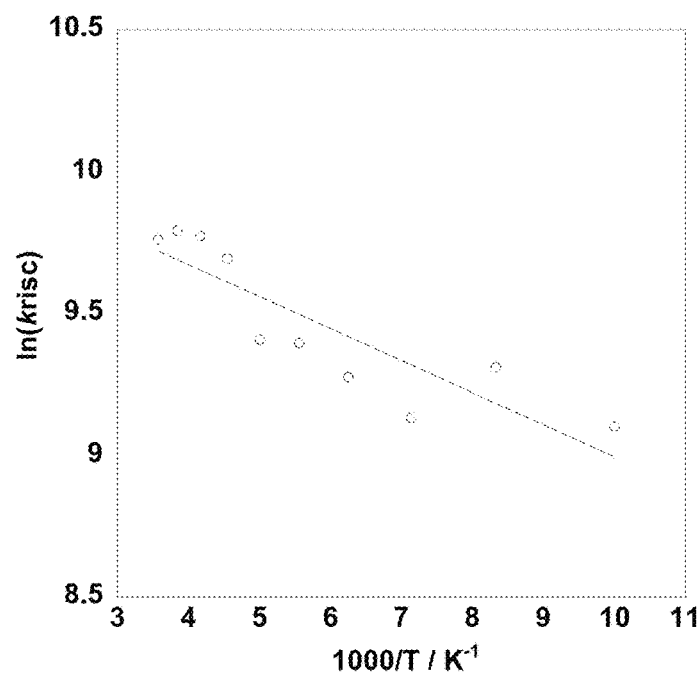
FIG. 14 shows the Arrhenius plot of the rate constant ($k_{RISC}$) of the thin film organic photoluminescent device of the compound 2 and mCP in Example 2.

FIG. 12 shows the result of the measurement of the light emission spectra with excitation light of 337 nm of the organic photoluminescent device having the thin film of the compound 2 and mCP and the organic photoluminescent device having the thin film of the compound 2 and CBP. FIG. 13 shows the transient decay curves measured at 100 K, 200 K, and 300 K of the organic photoluminescent device having the thin film of the compound 2 and mCP, and FIG. 14 shows the Arrhenius plot of the rate constant $k_{RISC}$ of the inverse intersystem crossing from the triplet excited state $T_1$ to the singlet excited state $S_1$. The photoluminescence quantum efficiency was 76% for the organic photoluminescent device having the thin film of the compound 2 and mCP, and 73% for the organic photoluminescent device having the thin film of the compound 2 and CBP, and FIG. 13 confirmed thermal activation type delayed fluorescence, in which the delayed fluorescent component was increased with the increase of the temperature. FIG. 14 revealed that the energy difference $\Delta E_{ST}$ between the singlet excited state and the triplet excited state was 0.025 eV.

Example 3

Production and Evaluation of Organic Photoluminescent Device Using Compound 3

A toluene solution of the compound 3 and an organic photoluminescent device having a thin film containing only the compound 3 were produced by changing the point that the compound 3 was used instead of the compound 1.

An organic photoluminescent device having a thin film of the compound 3 and mCP and an organic photoluminescent device having a thin film of the compound 3 and TPBi were produced by changing the point that the compound 3 was used instead of the compound 1, and mCP or TPBi was used instead of DPEPO.

Figure 15:
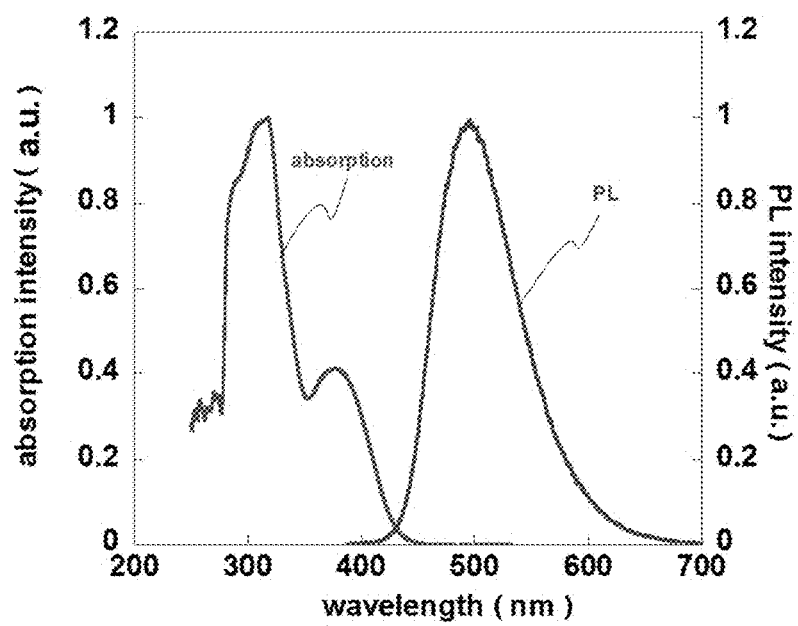
FIG. 15 shows the light emission and absorption spectra of the toluene solution of the compound 3 in Example 3.
Figure 16:
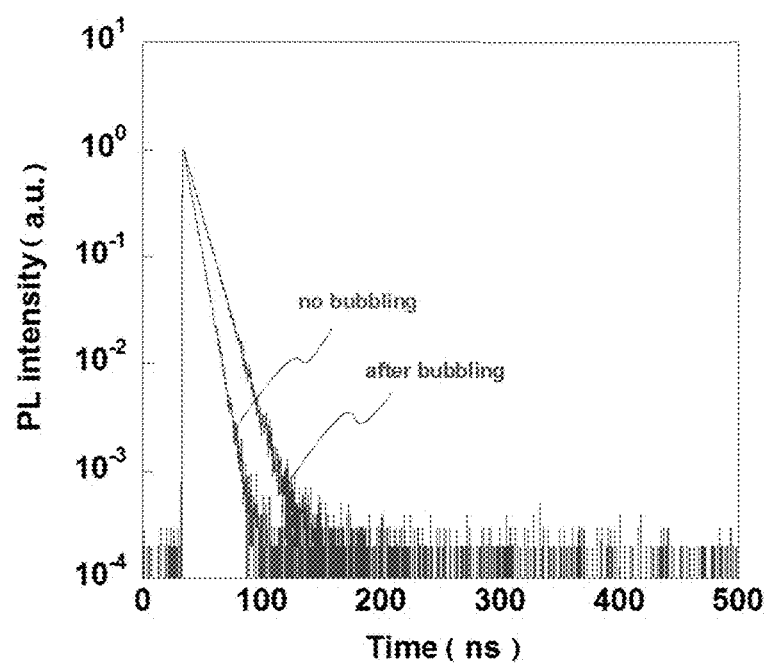
FIG. 16 shows the transient decay curves of the toluene solution of the compound 3 in Example 3.

FIG. 15 shows the measurement result of the light emission spectrum and the light absorption spectrum with excitation light of 377 nm of the toluene solution of the compound 3, and FIG. 16 shows the measurement result of the transient decay curves thereof. The photoluminescence quantum efficiency was 34.6% for the toluene solution without bubbling, and 56.1% for the toluene solution with nitrogen bubbling. FIG. 16 confirmed delayed fluorescence.

Figure 17:
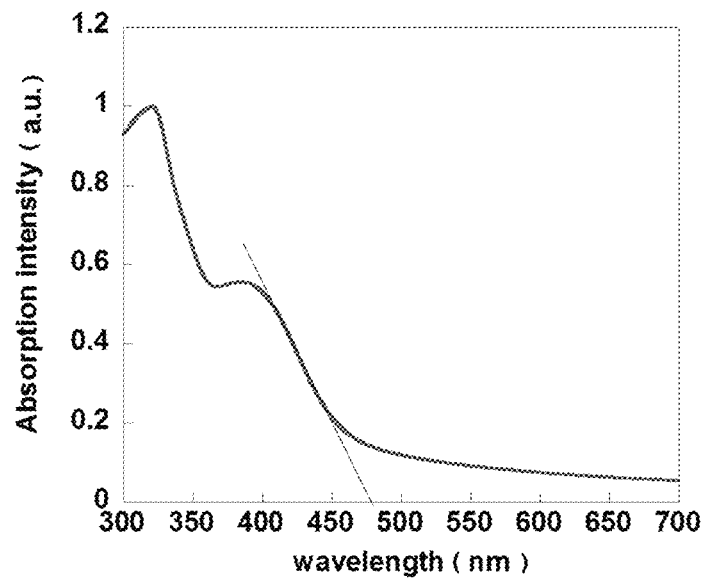
FIG. 17 shows the light absorption spectrum of the thin film organic photoluminescent device of the compound 3 in Example 3.
Figure 18:
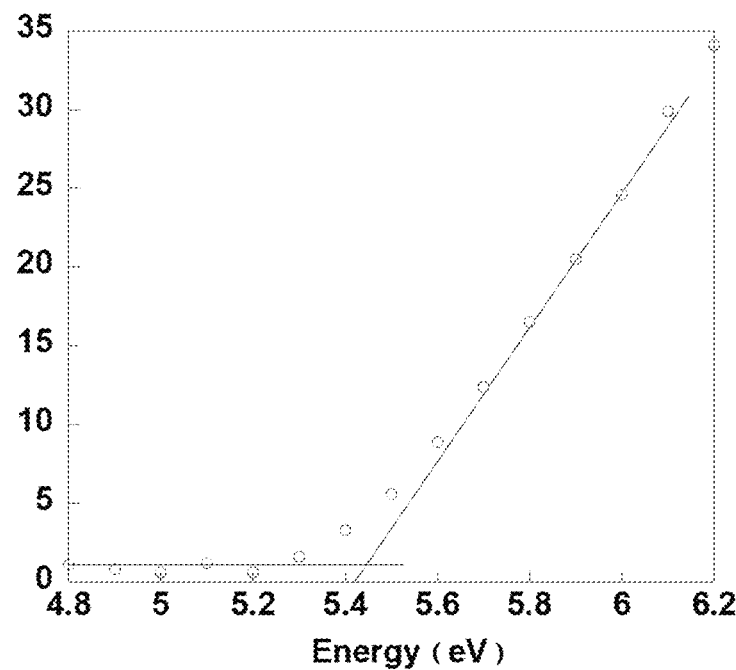
FIG. 18 shows the energy profile by a photoelectron analysis method of the thin film organic photoluminescent device of the compound 3 in Example 3.
Figure 19:
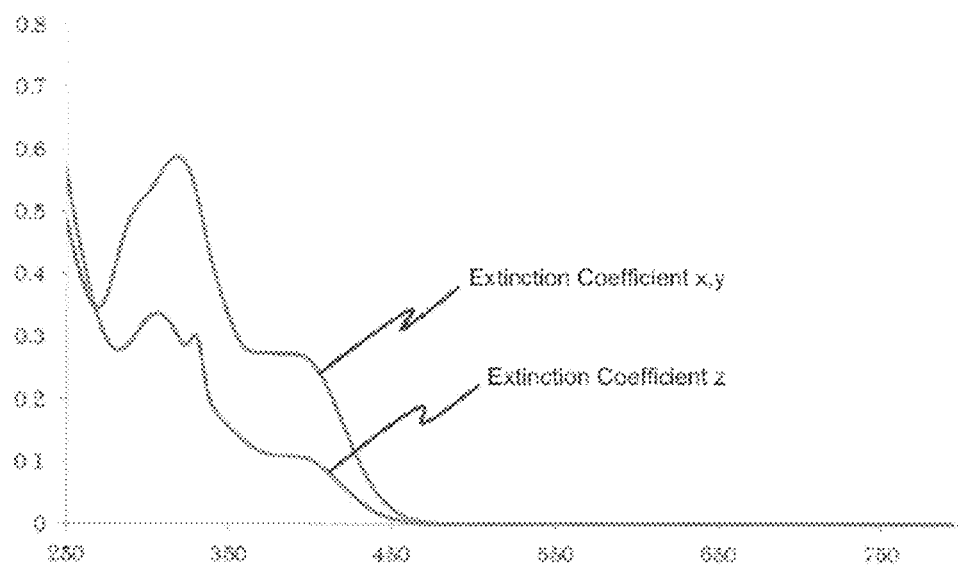
FIG. 19 shows the extinction coefficients in the directions of the plane (x,y) and the normal line (z) of the thin film obtained by an ellipsometric spectroscopy of the thin film organic photoluminescent device of the compound 3 in Example 3.

FIG. 17 shows the result of the measurement of the light absorption spectrum of the organic photoluminescent device having the thin film containing only the compound 3, and FIG. 18 shows the energy profile by a photoelectron analysis method thereof. FIG. 19 shows the extinction coefficients in the directions of the plane (x,y) and the normal line (z) of the thin film obtained by an ellipsometric spectroscopy thereof.

It was confirmed from FIG. 18 that the energy level of HOMO was 5.42 eV, the energy level of LUMO was 2.83 eV, and the HOMO-LUMO gap was 2.59 eV, which revealed that HOMO and LUMO were appropriately separated.

Figure 20:
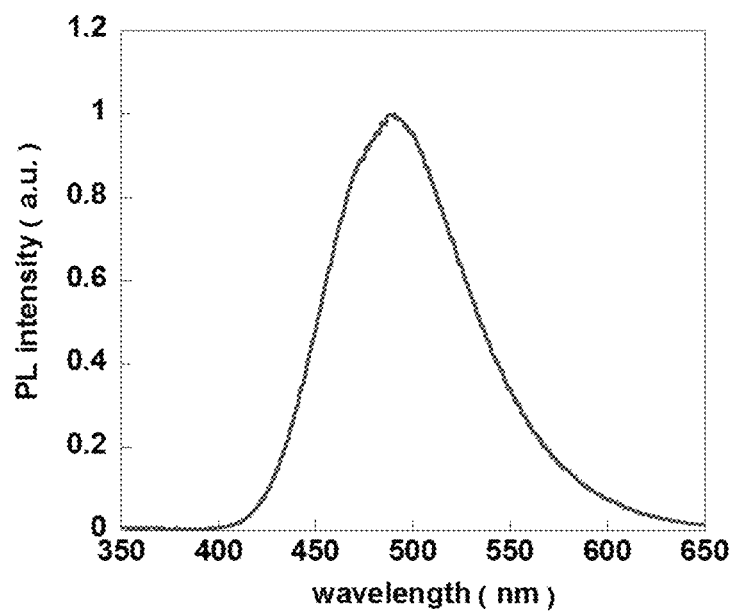
FIG. 20 shows the light emission spectrum of the thin film organic photoluminescent device of the compound 3 and mCP in Example 3.
Figure 21:
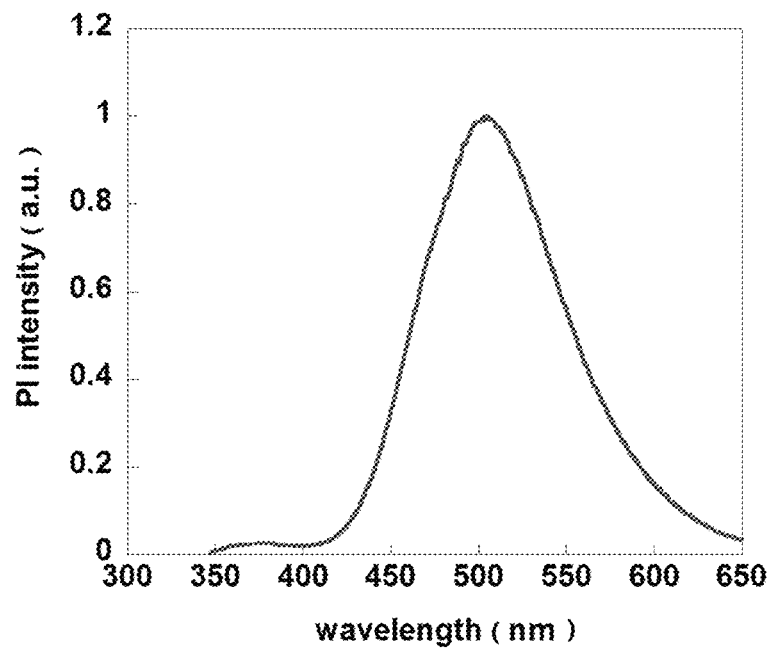
FIG. 21 shows the light emission spectrum of the thin film organic photoluminescent device of the compound 3 and TPBi in Example 3.
Figure 22:
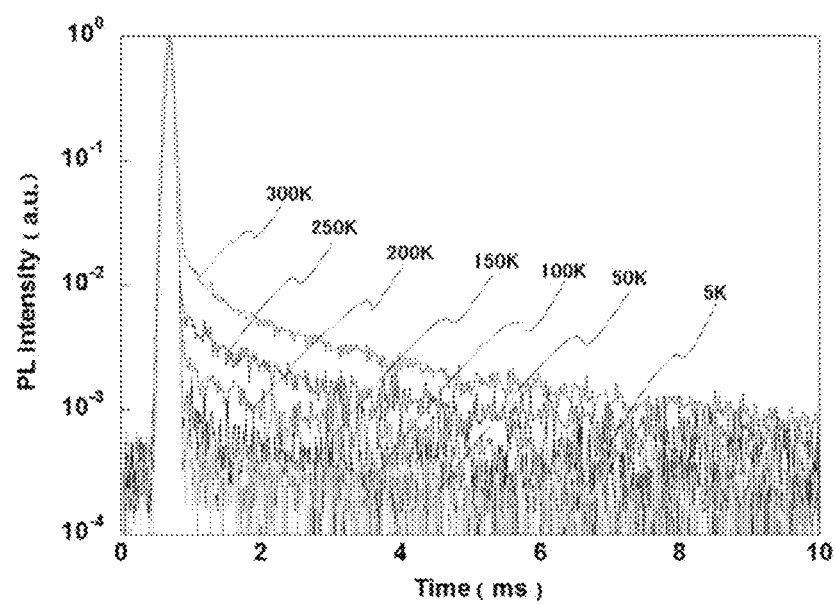
FIG. 22 shows the transient decay curves of the thin film organic photoluminescent device of the compound 3 and mCP in Example 3.
Figure 23:
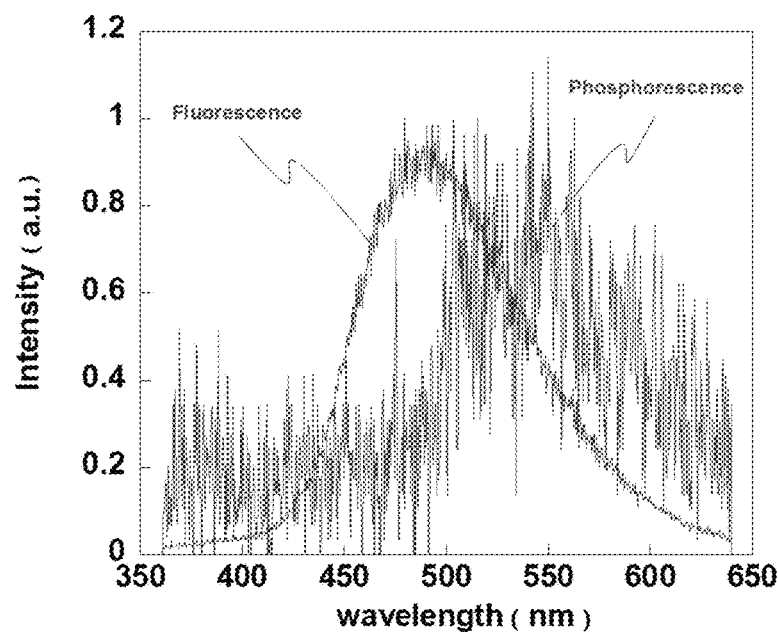
FIG. 23 shows the fluorescence spectrum and the phosphorescent spectrum of the thin film organic photoluminescent device of the compound 3 and mCP in Example 3.

FIG. 20 shows the result of the measurement of the light emission spectrum of the organic photoluminescent device having the thin film of the compound 3 and mCP, and FIG. 21 shows the result of the measurement of the light emission spectrum of the organic photoluminescent device having the thin film of the compound 3 and TPBi. The photoluminescence quantum efficiency was 59.7% for the organic photoluminescent device having the thin film of the compound 3 and mCP, and 54.7% for the organic photoluminescent device having the thin film of the compound 3 and TPBi. FIG. 22 shows the transient decay curves measured at temperatures within a range of from 5 to 300 K of the organic photoluminescent device having the thin film of the compound 3 and mCP, and FIG. 23 shows the fluorescence spectrum and the phosphorescent spectrum thereof. FIG. 22 confirmed thermal activation type delayed fluorescence, in which the delayed fluorescent component was increased with the increase of the temperature. FIG. 23 revealed that the energy difference $\Delta E_{ST}$ between the singlet excited state and the triplet excited state was 0.36 eV.

Example 4

Production and Evaluation of Organic Electroluminescence Device Using Compound 1

Thin films were laminated on a glass substrate having formed thereon an anode formed of indium tin oxide (ITO) having a thickness of 100 nm, by a vacuum vapor deposition method at a vacuum degree of $5 \times 10^{-4}$ Pa or less. Firstly, α-NPD was formed to a thickness of 35 nm on ITO, and mCBP was formed to a thickness of 10 nm. Subsequently, the compound 1 and DPEPO were co-deposited from separate vapor deposition sources to form a layer having a thickness of 15 nm, which was designated as a light-emitting layer. At this time, the concentration of the compound 1 was 6% by weight. TPBi was then formed to a thickness of 40 nm, further lithium fluoride (LiF) was vacuum vapor-deposited to a thickness of 0.5 nm, and then aluminum (Al) was vapor-deposited to a thickness of 100 nm to form a cathode, thereby completing an organic electroluminescence device.

Figure 24:
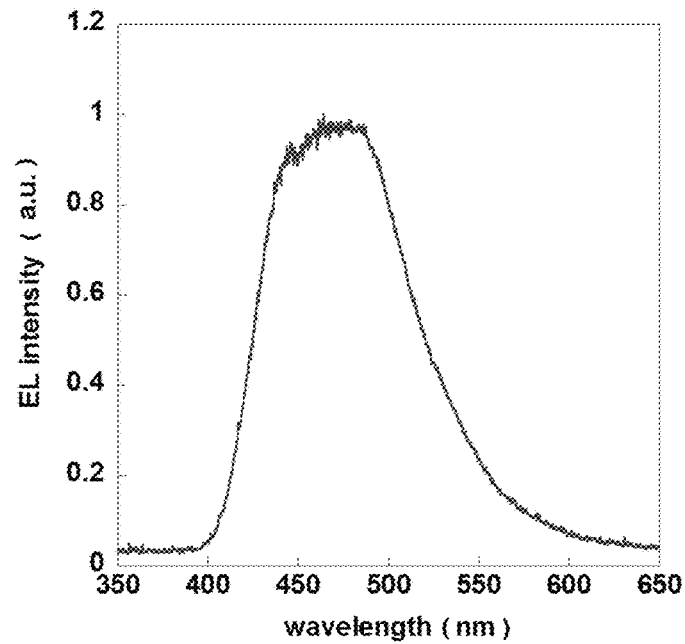
FIG. 24 shows the light emission spectrum of the organic electroluminescence device of the compound 1 in Example 4.
Figure 25:
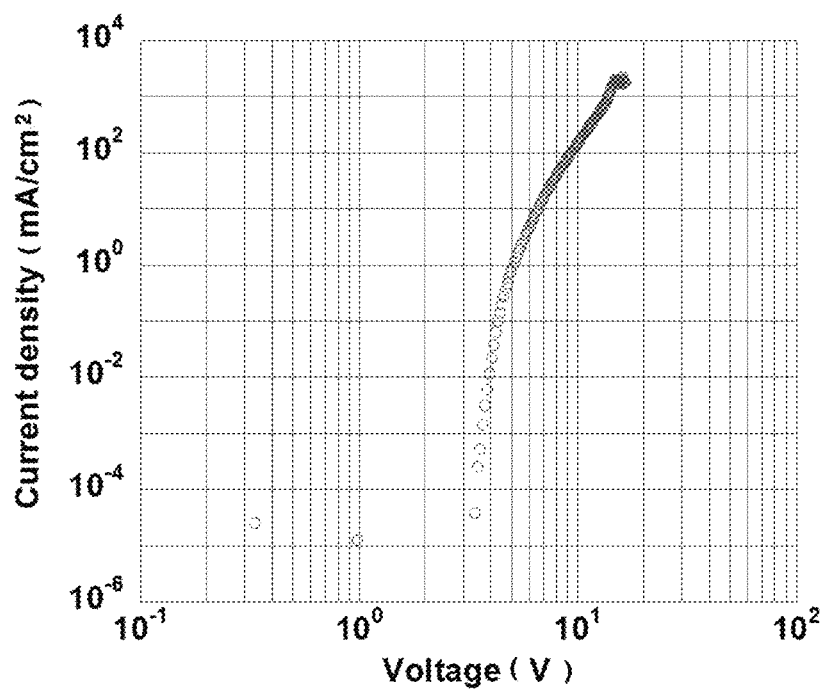
FIG. 25 shows a graph showing the voltage-current density characteristics of the organic electroluminescence device of the compound 1 in Example 4.
Figure 26:
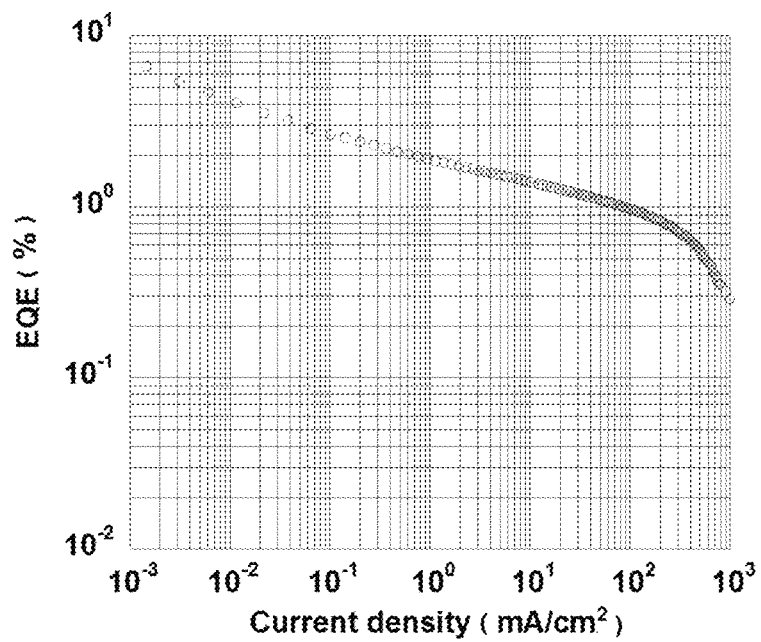
FIG. 26 shows a graph showing the current density-external quantum efficiency characteristics of the organic electroluminescence device of the compound 1 in Example 4.

FIG. 24 shows the light emission spectrum of the organic electroluminescence device thus produced, FIG. 25 shows the voltage-current density characteristics thereof, and FIG. 26 shows current density-external quantum efficiency characteristics thereof. The organic electroluminescence device using the compound 1 as a light-emitting material achieved a high external quantum efficiency of 6.64% under the condition of a voltage of 3.66 V and a current density of $1.451 \times 10^{-3}$ mA/cm$^2$.

Example 5

Production and Evaluation of Organic Electroluminescence Device Using Compound 3

Thin films were laminated on a glass substrate having formed thereon an anode formed of indium tin oxide (ITO) having a thickness of 100 nm, by a vacuum vapor deposition method at a vacuum degree of $5 \times 10^{-4}$ Pa or less. Firstly, α-NPD was formed to a thickness of 35 nm on ITO, and mCP was formed to a thickness of 10 nm. Subsequently, the compound 3 and mCP were co-deposited from separate vapor deposition sources to form a layer having a thickness of 10 nm, which was designated as a first light-emitting layer. At this time, the concentration of the compound 3 was 6% by weight. Subsequently, the compound 3 and TPBi were co-deposited from separate vapor deposition sources to form a layer having a thickness of 20 nm, which was designated as a second light-emitting layer. At this time, the concentration of the compound 3 was 6% by weight. TPBi was then formed to a thickness of 45 nm, further a mixture of magnesium and silver (Mg/Ag) was vacuum vapor-deposited to 100 nm, and then silver (Ag) was vapor-deposited to a thickness of 20 nm to form a cathode, thereby completing an organic electroluminescence device.

Figure 27:
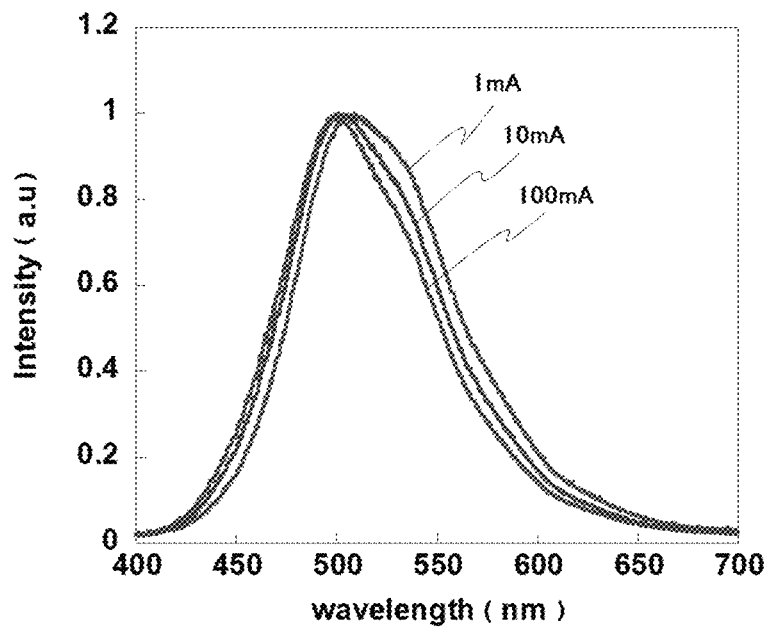
FIG. 27 shows the light emission spectra of the organic electroluminescence device of the compound 3 in Example 6.
Figure 28:
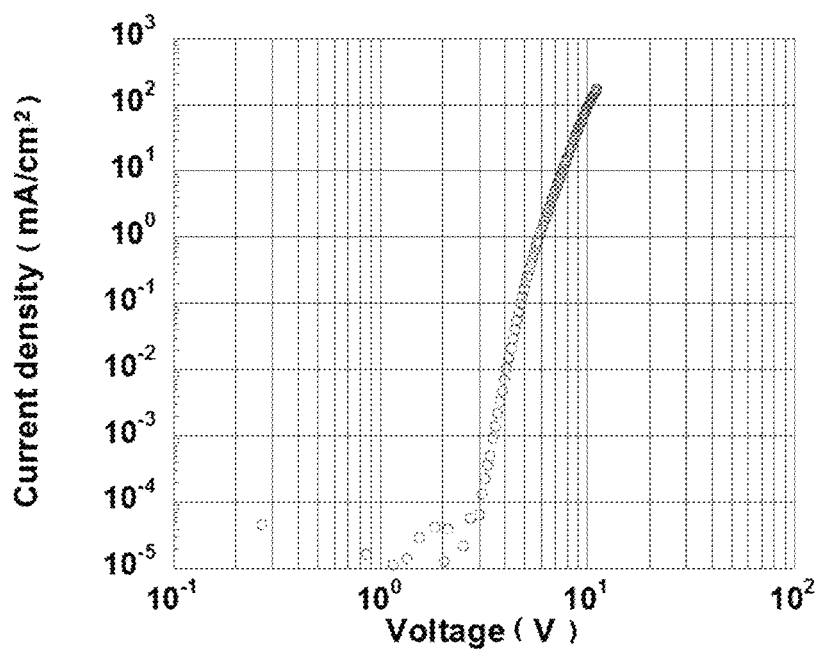
FIG. 28 shows a graph showing the voltage-current density characteristics of the organic electroluminescence device of the compound 3 in Example 6.
Figure 29:
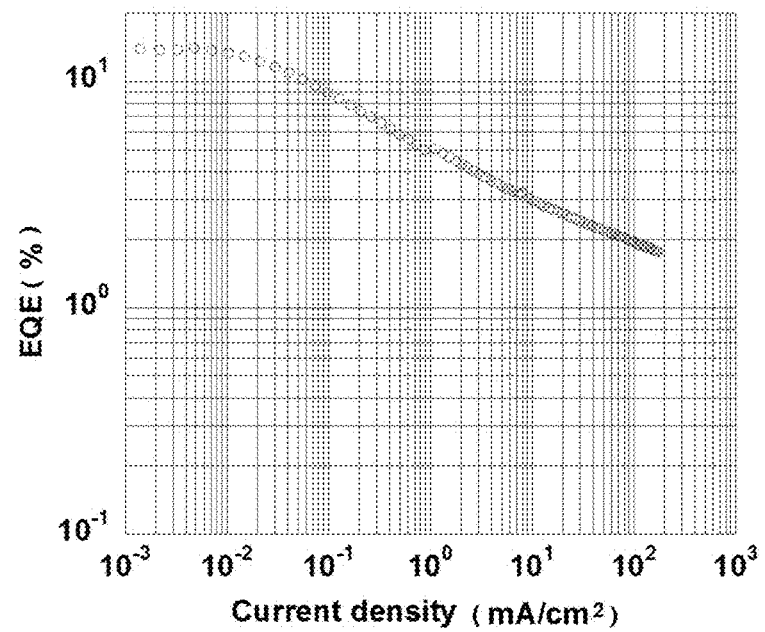
FIG. 29 shows a graph showing the current density-external quantum efficiency characteristics of the organic electroluminescence device of the compound 3 in Example 6.

FIG. 27 shows the light emission spectra measured under conditions of 1 mA, 10 mA, and 100 mA of the organic electroluminescence device thus produced, FIG. 28 shows the voltage-current density characteristics thereof, and FIG. 29 shows the current density-external quantum efficiency characteristics thereof. The organic electroluminescence device using the compound 3 as a light-emitting material achieved a high external quantum efficiency of 14.07% under the condition of a voltage of 3.88 V and a current density of 0.005 mA/cm$^2$.

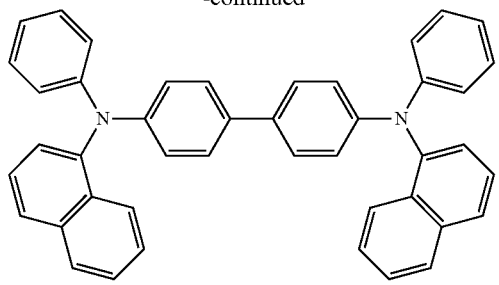

α-NPD

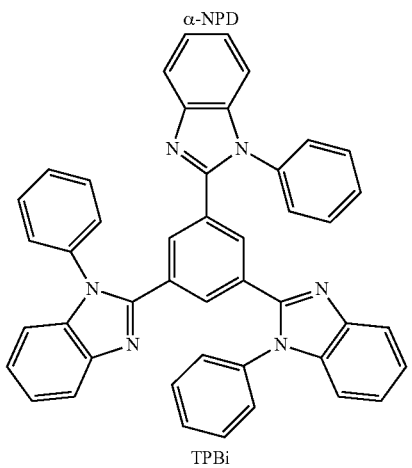

TPBi

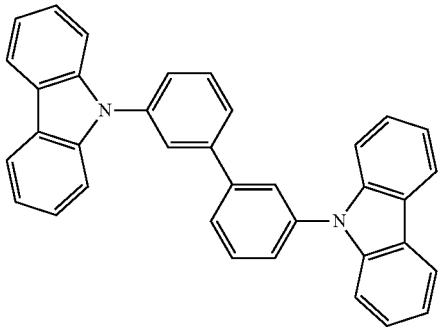

mCBP

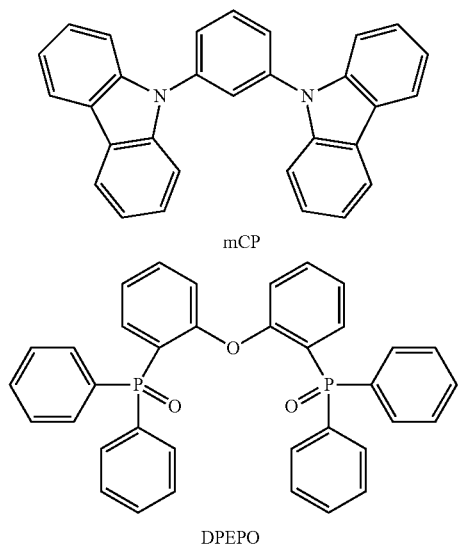

mCP

DPEPO

INDUSTRIAL APPLICABILITY

The compound of the invention is useful as a light-emitting material. Accordingly, the compound of the invention may be effectively used as a light-emitting material of an organic light-emitting device, such as an organic electroluminescence device. The compound of the invention includes a compound that emits delayed fluorescent light, and thus may be capable of providing an organic light-emitting device having a high light emission efficiency. Thus, the invention has high industrial applicability.

REFERENCE SIGNS LIST

1 substrate
2 anode
3 hole injection layer
4 hole transporting layer
5 light-emitting layer
6 electron transporting layer
7 cathode

The invention claimed is:
1. A compound represented by the following Formula (1):

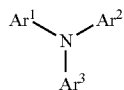

wherein $Ar^1$ to $Ar^3$ each independently represent a substituted or unsubstituted aryl group, provided that at least one of $Ar^1$ to $Ar^3$ each independently represent a carbazolyl group having an N-position substituted with a group containing an electron withdrawing group;
provided that the group containing an electron withdrawing group is not an aryl group having 6 to 30 carbon atoms substituted with at least one fluorine atom or a heteroaryl group having 4 to 30 carbon atoms substituted with at least one fluorine atom; and
provided that the Formula (1) does not include the following structure:

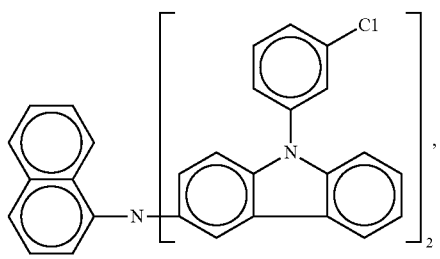

and
provided that the Formula (1) satisfies at least one of the following (A) to (C):
(A) the group containing an electron withdrawing group is a phenyl group substituted with at least one electron withdrawing group,
(B) two or three of $Ar^1$ to $Ar^3$ each represent a carbazolyl group having an N-position substituted with a group containing an electron withdrawing group,
(C) the carbazolyl group having an N-position substituted with a group containing an electron withdrawing group is represented by the following Formula (2):

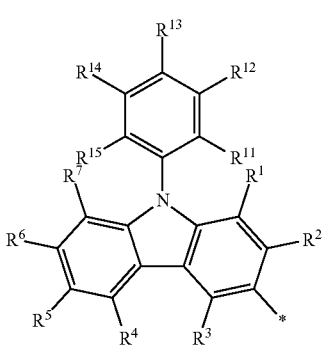

wherein * represents a position bonded to the nitrogen atom in Formula (1); and $R^1$ to $R^7$ and $R^{11}$ to $R^{15}$ each independently represent a hydrogen atom or a substituent, provided that at least one of $R^{11}$ to $R^{15}$ each independently represent an electron withdrawing group, $R^{11}$ to $R^{15}$ may be bonded to each other to form a cyclic structure, and $R^1$ and $R^2$, $R^4$ and $R^5$, $R^5$ and $R^6$, and $R^6$ and $R^7$ each may be bonded to each other to form a cyclic structure, and provided that the electron withdrawing group is not a fluorine atom or a chlorine atom.

2. The compound according to claim 1, wherein the group containing an electron withdrawing group is a phenyl group substituted with at least one electron withdrawing group.

3. The compound according to claim 2, wherein the phenyl group is substituted with the electron withdrawing group at 4-position of the phenyl group.

4. The compound according to claim 1, wherein the electron withdrawing group of (B) is a heterocyclic group containing a nitrogen atom, a cyano group, a group bonded through a carboxyl group, or a group bonded through an ester group.

5. The compound according to claim 1, wherein the electron withdrawing group of (B) is a heterocyclic group having a nitrogen atom as a constitutional atom of the ring, or a cyano group.

6. The compound according to claim 5, wherein the heterocyclic group having a nitrogen atom as a constitutional atom of the ring is a heterocyclic group represented by any one of the following formulae:

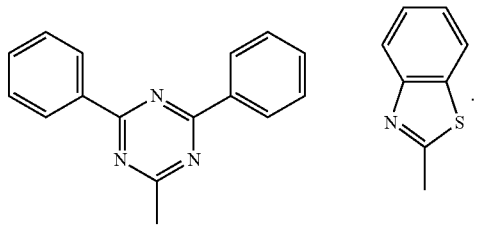

7. The compound according to claim 1, wherein two or three of $Ar^1$ to $Ar^3$ each represent a carbazolyl group having an N-position substituted with a group containing an electron withdrawing group.

8. The compound according to claim 7, wherein the carbazolyl groups having an N-position substituted with a group containing an electron withdrawing group have the same structure.

9. The compound according to claim 7, wherein two of $Ar^1$ to $Ar^3$ each represent the carbazolyl group having an N-position substituted with a group containing an electron withdrawing group, and the other one thereof represents a substituted or unsubstituted phenyl group.

10. The compound according to claim 1, wherein the carbazolyl group having an N-position substituted with a group containing an electron withdrawing group is represented by the following Formula (2):

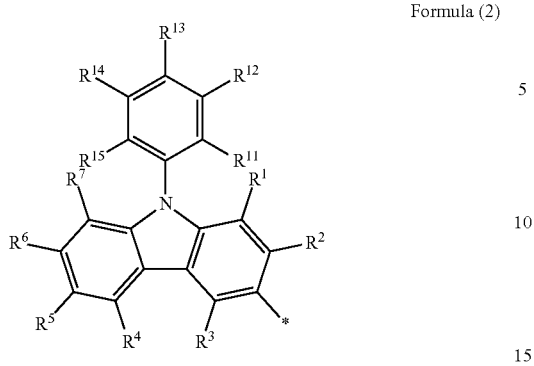

Formula (2)

wherein * represents a position bonded to the nitrogen atom in Formula (1); and $R^1$ to $R^7$ and $R^{11}$ to $R^{15}$ each independently represent a hydrogen atom or a substituent, provided that at least one of $R^{11}$ to $R^{15}$ each independently represent an electron withdrawing group, $R^{11}$ to $R^{15}$ may be bonded to each other to form a cyclic structure, and $R^1$ and $R^2$, $R^4$ and $R^5$, $R^5$ and $R^6$, and $R^6$ and $R^7$ each may be bonded to each other to form a cyclic structure, and provided that the electron withdrawing group is not a fluorine atom or a chlorine atom.

* * * * *